(12) United States Patent
Williams et al.

(10) Patent No.: US 9,006,347 B2
(45) Date of Patent: Apr. 14, 2015

(54) METHOD OF SYNTHESISING POLYCARBONATES IN THE PRESENCE OF A BIMETALLIC CATALYST AND A CHAIN TRANSFER AGENT

(71) Applicant: Imperial Innovations Limited, London (GB)

(72) Inventors: Charlotte K. Williams, London (GB); Michael Kember, London (GB); Antoine Buchard, London (GB); Fabian Jutz, London (GB)

(73) Assignee: Imperial Innovations Limited, London (GB)

( * ) Notice: Subject to any disclaimer, the term of this patent is extended or adjusted under 35 U.S.C. 154(b) by 0 days.

(21) Appl. No.: 14/201,299

(22) Filed: Mar. 7, 2014

(65) Prior Publication Data

US 2014/0249279 A1 Sep. 4, 2014

Related U.S. Application Data

(63) Continuation of application No. PCT/EP2012/067588, filed on Sep. 7, 2012.

(51) Int. Cl.
*C08F 283/00* (2006.01)
*C08G 64/18* (2006.01)
*B01J 31/22* (2006.01)
(Continued)

(52) U.S. Cl.
CPC .......... *C08G 64/18* (2013.01); *B01J 31/2243* (2013.01); *C08G 63/64* (2013.01); *C08G 64/0208* (2013.01); *C08G 64/34* (2013.01); *B01J 2231/14* (2013.01); *B01J 2531/0216* (2013.01); *B01J 2531/0241* (2013.01); *B01J 2531/22* (2013.01); *B01J 2531/23* (2013.01); *B01J 2531/26* (2013.01); *B01J 2531/31* (2013.01); *B01J 2531/46* (2013.01); *B01J 2531/56* (2013.01); *B01J 2531/62* (2013.01); *B01J 2531/72* (2013.01); *B01J 2531/842* (2013.01);
(Continued)

(58) Field of Classification Search
USPC ................. 502/150, 152.155; 528/196, 198
See application file for complete search history.

(56) References Cited

U.S. PATENT DOCUMENTS

| | | | |
|---|---|---|---|
| 2006/0223973 A1 | 10/2006 | Hinz et al. | |
| 2011/0118435 A1 | 5/2011 | Williams et al. | |

FOREIGN PATENT DOCUMENTS

| | | | |
|---|---|---|---|
| WO | WO 2009/130470 A1 | 10/2009 | |
| WO | WO 2009/137540 A1 | 11/2009 | |

(Continued)

OTHER PUBLICATIONS

Kember et al. 'Highly Active Di- and Trimetallic Cobalt Catalysts for the Copolymerization of CHO and CO2 at Atmospheric Pressure; Macromolecules articles 2010, 43 2291-2298.*

(Continued)

*Primary Examiner* — Terressa Boykin
(74) *Attorney, Agent, or Firm* — Wolf, Greenfield & Sacks, P.C.; C. Hunter Baker

(57) ABSTRACT

The invention provides a process for the synthesis of a polycarbonate, the process comprising the step of reacting carbon dioxide with at least one epoxide in the presence of a catalyst of formula (I) and a chain transfer agent. The invention also provides a polymerization system for the copolymerization of carbon dioxide and at least one epoxide comprising a catalyst of formula (I) and a chain transfer agent, polycarbonates produced by the inventive process, a block copolymer comprising a polycarbonate produced by the inventive process, and a method of producing the block copolymer. The invention also relates to novel catalysts of formula (III).

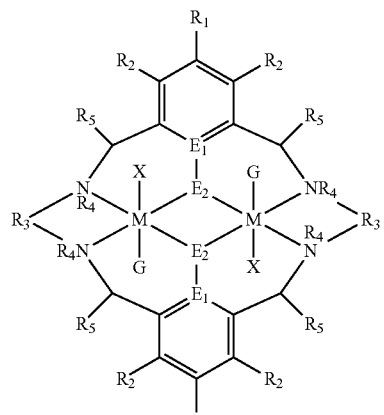

(I)

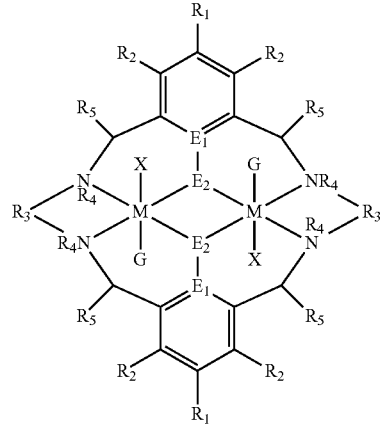

(III)

19 Claims, 15 Drawing Sheets

(51) Int. Cl.
| | |
|---|---|
| C08G 63/64 | (2006.01) |
| C08G 64/02 | (2006.01) |
| C08G 64/34 | (2006.01) |
| C07F 3/02 | (2006.01) |
| C07F 3/06 | (2006.01) |
| C08G 64/32 | (2006.01) |
| C08G 63/91 | (2006.01) |

(52) U.S. Cl.
CPC .............. B01J2531/845 (2013.01); *C07F 3/02* (2013.01); *C07F 3/06* (2013.01); *C08G 64/32* (2013.01)

(56) References Cited

FOREIGN PATENT DOCUMENTS

| | | |
|---|---|---|
| WO | WO 2010/028362 A1 | 3/2010 |
| WO | WO 2012/037282 A2 | 3/2012 |
| WO | WO 2013/034750 A2 | 3/2013 |

OTHER PUBLICATIONS

International Search Report and Written Opinion for PCT/GB2009/001043, mailed Jul. 7, 2009.
International Preliminary Report on Patentability for PCT/GB2009/001043, mailed Nov. 4, 2010.
International Search Report and Written Opinion for PCT/EP2012/067588, mailed Mar. 14, 2013.
International Preliminary Report on Patentability for PCT/EP2012/067588, mailed Mar. 20, 2014.
Allen et al., High-activity, single-site catalysts for the alternating copolymerization of CO2 and propylene oxide. J Am Chem Soc. Dec. 4, 2002;124(48):14284-5.
Bok et al., Bimetallic fluorine-substituted anilido-aldimine zinc complexes for CO2/(cyclohexene oxide) copolymerization. Inorg Chem. May 15, 2006;45(10):4228-37.
Cheng et al., Catalytic Reactions Involving C1 Feedstocks: New High-Activity Zn(II)-Based Catalysts for the Alternating Copolymerization of Carbon Dioxide and Epoxides. J Am Chem Soc. 1998;120:11018-19.
Coates et al., Discrete Metal-Based Catalyst for the Copolymerization of CO2 and Epoxides: Discovery, Reactivity, Optimization, and Mechanism. Angew Chem Int Ed. 2004;43:6618-39.
Darensbourg et al., *Bis* 2,6-difluorophenoxide Dimeric Complexes of Zinc and Cadmium and Their Phosphine Adducts :Lessons Learned Relative to Carbon Dioxide/Cyclohexene Oxide Alternating Copolymerization Processes by Zinc Phenoxides. J Am Chem Soc. 2000;122:12487-96.
Darensbourg et al., Catalytic Activity of a Series of ZN(II) Phenoxides for the Copolymerization of Epoxides and Carbon Dioxides. J Am Chem Soc. 1999;121:107-16.
Darensbourg et al., Mechanistic aspects of the copolymerization reaction of carbon dioxide and epoxides, using a chiral salen chromium chloride catalyst. J Am Chem Soc. Jun. 5, 2002;124(22):6335-42.
Darensbourg et al., Solution and solid-state structures of phosphine adducts of monomeric zinc bisphenoxide complexes. Importance of these derivatives in CO2/epoxide copolymerization processes. Inorg Chem. Apr. 3, 2000;39(7):1578-85.
Darensbourg, Making plastics from carbon dioxide: salen metal complexes as catalysts for the production of polycarbonates from epoxides and CO2. Chem Rev. Jun. 2007;107(6):2388-410. Epub Apr. 21, 2007.
Das et al., Iso- and mixed-valent phenoxy bridged binuclear macrocyclic complexes of cobalt, iron and manganese. Polyhedron. 1994;13(38):2639-45.
Dutta et al., Efficient proton-templated synthesis of 18- to 38-membered tetraimino(amino)diphenol macrocyclic ligands: structural features and spectroscopic properties. J Org Chem. Aug. 6, 2004;69(16):5419-27.
Dutta et al., Model Compounds for Iron Proteins. Structures and Magnetic, Spectroscopic, and Redox Properties of Fe(III)M(II) and [Co(III)Fe(III)](2)O Complexes with (µ-Carboxylato)bis(µ-phenoxo)dimetalate and (µ-Oxo)diiron(III) Cores. Inorg Chem. Apr. 10, 1996;35(8):2292-2300.
Eberhardt et al., The Ethylsulfinate Ligand: A Highly Efficient Initiating Group for the Zinc β- Diiminate Catalyzed Copolymerization of CO2 and Epoxides. Organometallics. 2003;22:211-14.
Inoue et al., Copolymerization of carbon dioxide and epoxide. Polymer Letts. 1969;7:287-92.
Kember et al., Di- and Tri-Zinc catalysts for the low-pressure copolymerization of CO2 and Cyclohexene Oxide. Inorg Chem. 2009;48:9535-42.
Kember et al., Highly active dizine catalyst for the copolymerization of carbon dioxide and cyclohexene oxide at one atmosphere pressure. Agnew Chem Int Ed. 2009;48:931-3.
Knight et al., Dinuclear zinc complexes using pentadentate phenolate ligands. Inorg Chem. Dec. 15, 2008;47(24):11711-9.
Koning et al., Synthesis and physical characterization of poly(cyclohexane carbonate), synthesized from CO2 and cyclohexene oxide. Polymer. 2001;42:3995-4004.
Lee et al., Bimetallic anilido-aldimine zinc complexes for epoxide/CO2 copolymerization. J Am Chem Soc. Mar. 9, 2005;127(9):3031-7.
Moore et al., Mechanism of the alternating copolymerization of epoxides and CO2 using beta-diiminate zinc catalysts: evidence for a bimetallic epoxide enchainment. J Am Chem Soc. Oct. 1, 2003;125(39):11911-24.
Nozaki et al., Asymmetric catalytic synthesis of polyketones and polycarbonates. Pure Appl Chem. 2004;76(3):541-46.
Paddock et al., Chemical CO(2) fixation: Cr(III) salen complexes as highly efficient catalysts for the coupling of CO(2) and epoxides. J Am Chem Soc. Nov. 21, 2001;123(46):11498-9.
Pilz et al., Dinuclear Zinc Complexes Based on Parallel β-Diiminato Binding Sites: Syntheses, Structures, and Properties as CO2/Epoxide Copolymerization Catalysts. Organometallics. 2007;26:3668-76.
Qin et al., Cobalt-Based Complexes for the Copolymerization of Propylene Oxide and CO2; Active and Selective Catalysts for Polycarbonate Synthesis. Angew Chem Int Ed. 2003;42:5484-87.
Rokicki et al., The Application of Carbon Dioxide as a Direct Material for Polymer Syntheses in Polymerization and Polycondensation Reactions. J Macromol Sci Rev Macomol Chem Phys 1981;C21(1):135-86.
Sugimoto et al., Alternating Copolymerization of Carbon Dioxide and Epoxide by Manganese Porphyrin: The First Example of Polycarbonate Synthesis from 1-atm Carbon Dioxide. J Polym Sci Polym Chem. 2003;41:3549-55.
Sugimoto et al., Copolymerization of Carbon Dioxide and Epoxide. J Polym Sci Polym Chem. 2004;42:5561-73.
Sugimoto et al., The Cobalt Porphyrin—Lewis Base System: A Highly Selective Catalyst for Alternating Copolymerization of CO2 and Epoxide under Mild Condition. Macromolecules. 2008;41:312-17.
Van Meerendonk et al., High-Throughput Automated Parallel Evaluation of Zinc-Based Catalysts for the Copolymerization of CHO and CO2 to Polycarbonates. Macromol Rapid Commun. 2004;25:382-86.
Van Meerendonk et al., Unexpected Side Reactions and Chain Transfer for Zinc-Catalyzed Copolymerization of Cyclohexene Oxide and Carbon Dioxide. Macromolecules. 2005;38:7306-13.
Williams et al., A highly active zinc catalyst for the controlled polymerization of lactide. J Am Chem Soc. Sep. 17, 2003;125(37):11350-9.
Williams et al., Metalloenzyme inspired dizinc catalyst for the polymerization of lactide. Chem Commun (Camb). Sep. 21, 2002;(18):2132-3.
Xiao et al., Copolymerization of cyclohexene oxide with CO2 by using intramolecular dinuclear zinc catalysts. Chemistry. Jun. 6, 2005;11(12):3668-78.

(56) References Cited

OTHER PUBLICATIONS

Xiao et al., Intramolecularly Dinuclear Magnesium Complex Catalyzed Copolymerization of Cyclohexene Oxide with CO2 under Ambient CO2 Pressure: Kinetics and Mechanism. Macromolecules. 2006;39:128-37.

Black et al., Compartmental Schiff-base ligands as selective double-loaded extractants for copper(II). Chem Commun (Camb). Feb. 21, 2002;(4):340-1.

Bradley et al., Homometallic Alkoxides. Alkoxo and Aryloxo Derivatives of Metals. Elsevier. 2001; 1:105-109.

Cheng et al., Single-site beta-diiminate zinc catalysts for the alternating copolymerization of CO2 and epoxides: catalyst synthesis and unprecedented polymerization activity. J Am Chem Soc. Sep. 12, 2001;123(36):8738-49.

Lu et al., Design of highly active binary catalyst systems for CO2/epoxide copolymerization: polymer selectivity, enantioselectivity, and stereochemistry control. J Am Chem Soc. Feb. 8, 2006;128(5):1664-74.

\* cited by examiner

METHOD OF SYNTHESISING POLYCARBONATES IN THE PRESENCE OF A BIMETALLIC CATALYST AND A CHAIN TRANSFER AGENT

RELATED APPLICATIONS

The present application claims priority under 35 U.S.C. §120 to and is a continuation of international PCT Application, PCT/EP2012/067588, filed Sep. 7, 2012, which claims priority to United Kingdom application number 1115565.2, filed Sep. 8, 2011, each of which is incorporated herein by reference.

FIELD

The present invention relates to a process for the synthesis of a polycarbonate from carbon dioxide and an epoxide, in the presence of a bimetallic catalyst and a chain transfer agent.

BACKGROUND

Environmental and economical concerns associated with depleting oil resources have triggered a growing interest in the chemical conversion of carbon dioxide ($CO_2$), so as to enable its use as a renewable carbon source. $CO_2$ is, despite its low reactivity, a highly attractive carbon feedstock, as it is inexpensive, virtually non-toxic, abundantly available in high purity and non-hazardous. Therefore, $CO_2$ could be a promising substitute for substances such as carbon monoxide or phosgene in many processes. One of the developing applications of $CO_2$ is the copolymerization with epoxides to yield aliphatic polycarbonates, a field pioneered by Inoue et al. more than 40 years ago (Inoue, S. et al, *J. Polym. Sci., Part B: Polym. Lett.* 1969, 7, pp 287).

In WO2009/130470, the contents of which are incorporated herein by reference in their entirety, the copolymerisation of an epoxide with $CO_2$ using a catalyst of a class represented by formula (I) was described:

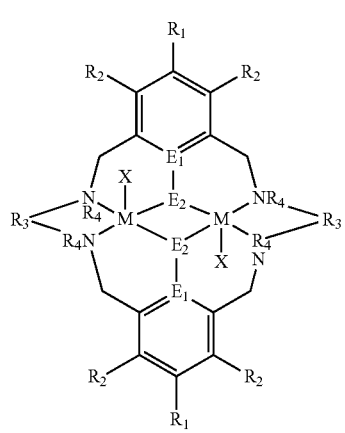

Among the epoxides employed in the copolymerization, cyclohexene oxide (CHO) has received special interest, as the product, poly(cyclohexene carbonate) (PCHC) shows a high glass transition temperature and reasonable tensile strength. Propylene oxide has also received interest as it produces a polymer (polypropylene carbonate, known as PPC) with elastomeric properties which are useful in film applications.

Kember et at (*Angew. Chem., Int. Ed.*, 2009, 48, pp 931 and *Inorg. Chem.*, 2009, 48, pp 9535) recently reported an air-stable di-zinc acetate complex, coordinated by a macrocyclic ligand, falling within formula (I) above, which shows high catalytic activity, even at ambient $CO_2$ pressure. The catalyst exhibits excellent copolymerization selectivity, giving high proportions of carbonate repeat units and low yields of cyclic cyclohexene carbonate (CHC) by-product. The di-zinc acetate complex is a rare example of a catalyst that is capable of high activity at ambient pressure (1 bar) of $CO_2$, yielding PCHC of moderate molecular weight, with narrow polydispersity index (PDI), and reaching remarkably high turnover numbers (TON).

Polycarbonates such as PCHC or PPC, are useful building blocks in the preparation of various copolymeric materials. Polycarbonates produced by copolymerisation of an epoxide with carbon dioxide using a catalyst of the class represented by formula (I) are generally terminated at one end with at least one hydroxyl group and at the other end by a group corresponding to ligand X. To use these polycarbonates as building blocks in the formation of, for example, block copolymers, it is desirable for all termination to be by hydroxyl groups. In a linear polycarbonate, for example, this would allow direct coupling of further polymer blocks to the ends of the polycarbonate, or growth of further polymer from the ends, i.e. by ring opening polymerisation, initiated by the terminal hydroxyl groups. Thus, further purification/work-up steps may be needed to replace terminal X groups with hydroxyl groups. A method for producing polycarbonates which are terminated with hydroxyl groups, avoiding the need for purification/work-up steps is desirable and it has been determined that this can be achieved by use of a chain transfer agent (CTA) during the polymerisation of $CO_2$ with an epoxide.

SUMMARY

There is provided by the first aspect of the invention a process for the synthesis of a polycarbonate, the process comprising the step of reacting carbon dioxide with at least one epoxide in the presence of a catalyst of formula (I):

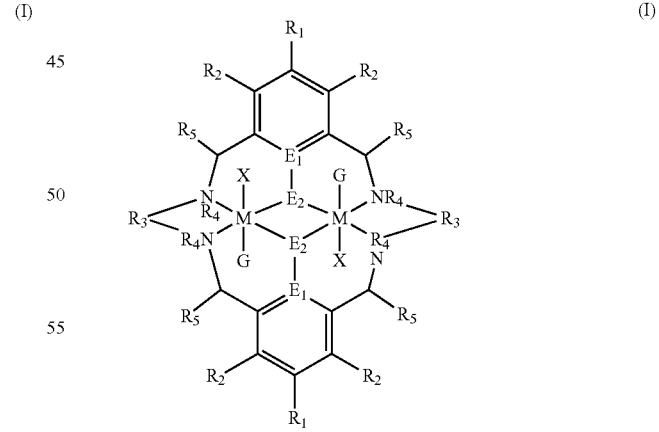

wherein $R_1$ and $R_2$ are independently hydrogen, halide, a nitro group, a nitrile group, an imine, an amine, an ether group, a silyl ether group, or an acetylide group or an optionally substituted alkyl, alkenyl, alkynyl, haloalkyl, aryl, heteroaryl, alicyclic or heteroalicyclic;

$R_3$ is optionally substituted alkylene, alkenylene, alkynylene, heteroalkylene, heteroalkenylene, heteroalkynylene, arylene, heteroarylene or cycloalkylene, wherein alkylene, alkenylene, alkynylene, heteroalkylene, heteroalkenylene and heteroalkynylene may optionally be interrupted by aryl, heteroaryl, alicyclic or heteroalicyclic;

$R_4$ is H, or optionally substituted aliphatic, heteroaliphatic, alicyclic, heteroalicyclic, aryl, heteroaryl, alkylheteroaryl or alkylaryl;

$R_5$ is H, or optionally substituted aliphatic, heteroaliphatic, alicyclic, heteroalicyclic, aryl, heteroaryl, alkylheteroaryl or alkylaryl;

$E_1$ is C, $E_2$ is O, S or NH or $E_1$ is N and $E_2$ is O;

X is $OC(O)R^x$, $OSO_2R^x$, $OSO(R^x)_2$, $OS(O)R^x$, $OR^x$, phosphinate, halide, nitrate, hydroxyl, carbonate, amido or optionally substituted aliphatic, heteroaliphatic, alicyclic, heteroalicyclic, aryl or heteroaryl;

$R_x$ is independently hydrogen, or optionally substituted aliphatic, haloaliphatic, heteroaliphatic, alicyclic, heteroalicyclic, aryl, arylalkyl or heteroaryl;

each G is independently absent or a neutral or anionic donor ligand which is a Lewis base;

M is Zn(II), Cr(II), Co(II), Mn(II), Mg(II), Fe(II), Ti(II), Cr(III)-X, Co(III)-X, Mn (III)-X, Fe(III)-X, Ca(II), Ge(II), Al(III)-X, Ti(III)-X, V(III)-X, Ge(IV)-$(X)_2$ or Ti(IV)-$(X)_2$;

and a chain transfer agent selected from water or a compound of formula (II):

$$Z\text{-}(W)_n \quad (II)$$

wherein

Z is an optionally substituted moiety selected from the group consisting of aliphatic, heteroaliphatic, alicyclic, heteroalicyclic, aryl, heteroaryl, polyolefin, polyester, polyether, polycarbonate or combinations thereof, each W is independently selected from a hydroxyl, amine, thiol or carboxylate group, and n is an integer which is at least 1.

The second aspect of the invention provides a polymerisation system for the copolymerisation of carbon dioxide and at least one epoxide comprising a catalyst as defined in the first aspect, and a chain transfer agent as defined in the first aspect.

The third aspect of the invention provides a polycarbonate as produced by of the process of the first aspect of the invention.

The fourth aspect of the invention provides a block copolymer of formula B-$(A)_n$, wherein B is a polycarbonate produced by the process of the first aspect of the invention and A is a polymeric unit differing in structure from B.

The fifth aspect of the invention provides a method of producing the block copolymer of the fourth aspect, comprising the steps of synthesising a polycarbonate according to the process of the first aspect and either reacting the polycarbonate with at least one further monomer, or reacting the polycarbonate with at least one further polymeric unit.

In a sixth aspect of the invention, a catalyst of formula (III) is provided:

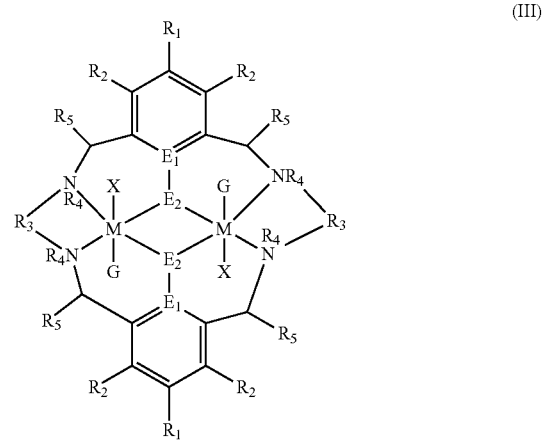

(III)

wherein $R_1$ and $R_2$ are independently hydrogen, halide, a nitro group, a nitrile group, an imine an amine, an ether group, a silyl ether group or an acetylide group or optionally substituted alkyl, alkenyl, alkynyl, haloalkyl, aryl, heteroaryl, alicyclic or heteroalicyclic;

$R_3$ is optionally substituted alkylene, alkenylene, alkynylene, heteroalkylene, heteroalkenylene, heteroalkynylene, arylene, heteroarylene or cycloalkylene, wherein alkylene, alkenylene, alkynylene, heteroalkylene, heteroalkenylene and heteroalkynylene may optionally be interrupted by aryl, heteroaryl, alicyclic or heteroalicyclic;

$R_4$ is H, or optionally substituted aliphatic, heteroaliphatic, alicyclic, heteroalicyclic, aryl, heteroaryl, alkylheteroaryl or alkylaryl;

$R_5$ is H, or optionally substituted aliphatic, heteroaliphatic, alicyclic, heteroalicyclic, aryl, heteroaryl, alkylheteroaryl or alkylaryl;

$E_1$ is C, $E_2$ is O, S or NH or $E_1$ is N and $E_2$ is O;

each G is independently absent or a neutral or anionic donor ligand which is a Lewis base;

M is Zn(II), Co(II), Mn(II), Mg (II), Fe(II), Cr(II), Ti(II), Cr (III)-X, Co(III)-X, Mn(III)-X, Fe(III)-X, Ca(II), Ge(II), Al(III)-X, Ti(III)-X, V(III)-X, Ge(IV)-$(X)_2$ or Ti(IV)-$(X)_2$;

wherein when both instances of G are absent and all instances of $R_5$ are hydrogen, X is $OC(O)R^Z$, $OSO(R^Z)_2$, $OSO_2R^Y$, $OS(O)R^T$, $OR^V$, phosphinate, hydroxyl, carbonate, nitrate or optionally substituted aryl, heteroaryl, alicyclic or heteroalicyclic;

$R^Z$ is independently hydrogen or optionally substituted $C_{2-20}$ aliphatic, $C_{2-20}$ haloaliphatic, heteroaliphatic, alicyclic, heteroalicyclic, aryl, alkylaryl or heteroaryl;

$R^Y$ is hydrogen or optionally substituted aliphatic, heteroaliphatic, alicyclic, heteroalicyclic, aryl, heteroaryl or alkylaryl with the proviso that $R^Y$ is not $C_7H_7$; and $R^V$ is optionally substituted aryl, haloaryl, heteroaryl, heteroaliphatic, alicyclic, alkylaryl or heteroaliyclic;

$R^T$ is hydrogen, or optionally substituted aliphatic, haloaliphatic, heteroaliphatic, alicyclic, heteroalicyclic, aryl, alkylaryl or heteroaryl; and wherein when either one or both instances of G are not absent, or one or more $R_5$ is not hydrogen, X is $OC(O)R^x$, $OSO_2R^x$, $OSO(R^x)_2$, $OS(O)R^x$, $OR^x$, phosphinate, halide, nitrate, hydroxyl, carbonate, amido or optionally substituted aliphatic, heteroaliphatic, alicyclic, heteroalicyclic, aryl or heteroaryl; and $R_x$ is independently hydrogen, or optionally substituted aliphatic, haloaliphatic, heteroaliphatic, alicyclic, heteroalicyclic, aryl, alkylaryl or heteroaryl.

BRIEF DESCRIPTION OF THE DRAWINGS

Embodiments of the invention are described below by way of example and with reference to the accompanying drawings in which.

DEFINITIONS

Figure 1:
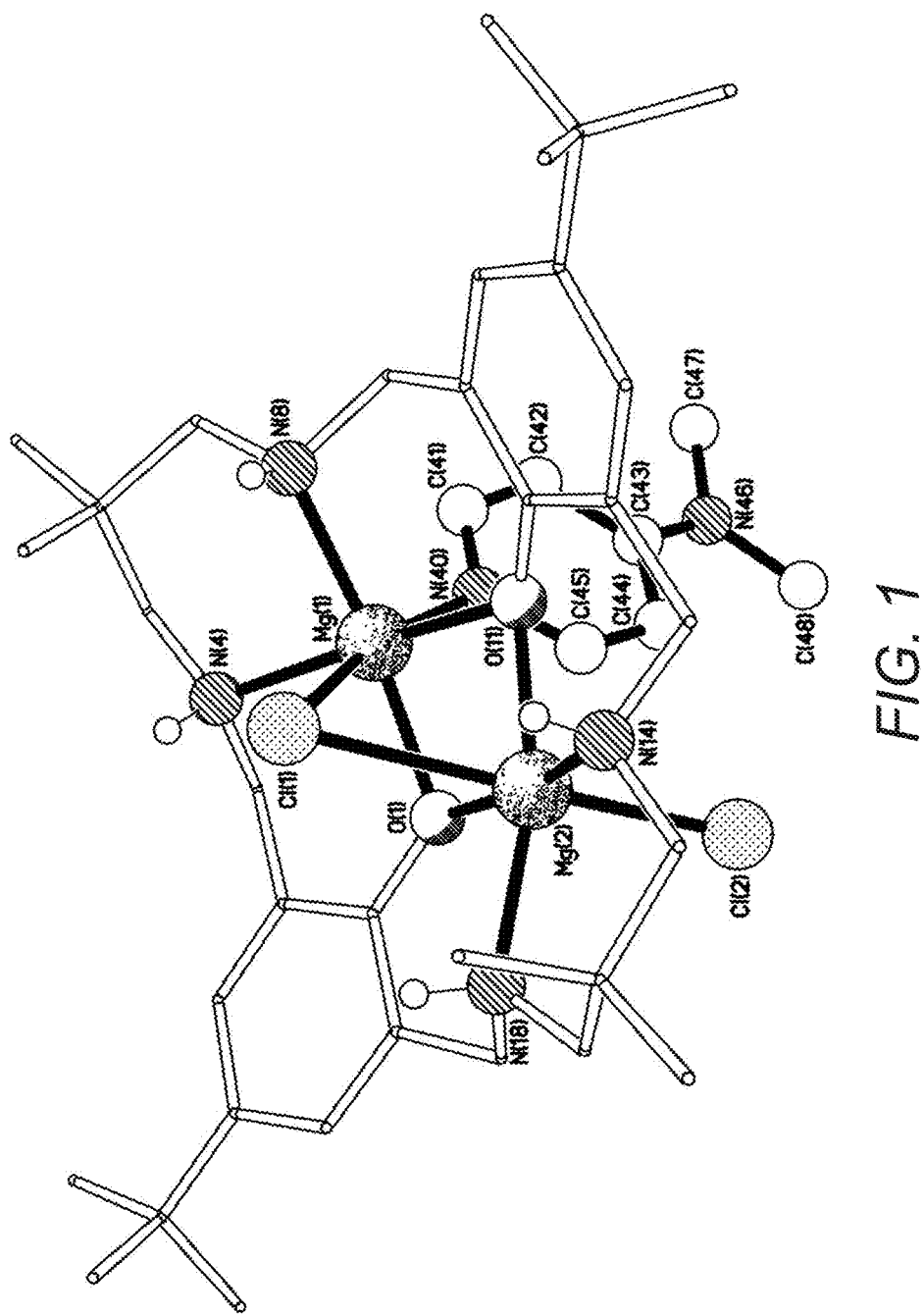
FIG. 1 shows the molecular structure of $[L^1Mg_2Cl_2(dimethylaminopyridine)]$

For the purpose of the present invention, an aliphatic group is a hydrocarbon moiety that may be straight chain or branched and may be completely saturated, or contain one or more units of unsaturation, but which is not aromatic. The term "unsaturated" means a moiety that has one or more double and/or triple bonds. The term "aliphatic" is therefore intended to encompass alkyl, alkenyl or alkynyl groups, and combinations thereof. An aliphatic group is preferably a $C_{1-20}$aliphatic group, that is an aliphatic group with 1, 2, 3, 4, 5, 6, 7, 8, 9, 10, 11, 12, 13, 14, 15, 16, 17, 18, 19 or 20 carbon atoms. Preferably, an aliphatic group is a $C_{1-15}$-aliphatic, more preferably a $C_{1-12}$aliphatic, more preferably a $C_{1-10}$aliphatic, even more preferably a $C_{1-8}$aliphatic, such as a $C_{1-6}$aliphatic group.

An alkyl group is preferably a "$C_{1-20}$ alkyl group", that is an alkyl group that is a straight or branched chain with 1 to 20 carbons. The alkyl group therefore has 1, 2, 3, 4, 5, 6, 7, 8, 9, 10, 11, 12, 13, 14, 15, 16, 17, 18, 19 or 20 carbon atoms. Preferably, an alkyl group is a $C_{1-15}$-alkyl, preferably a $C_{1-12}$alkyl, more preferably a $C_{1-10}$alkyl, even more preferably a $C_{1-8}$alkyl, even more preferably a $C_{1-6}$alkyl group. In certain embodiments, an alkyl group is a "$C_{1-6}$ alkyl group", that is an alkyl group that is a straight or branched chain with 1 to 6 carbons. The alkyl group therefore has 1, 2, 3, 4, 5 or 6 carbon atoms. Specifically, examples of "$C_{1-20}$ alkyl group" include methyl group, ethyl group, n-propyl group, iso-propyl group, n-butyl group, iso-butyl group, sec-butyl group, tert-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, n-nonadecyl group, n-eicosyl group, 1,1-dimethylpropyl group, 1,2-dimethylpropyl group, 2,2-dimethylpropyl group, 1-ethylpropyl group, n-hexyl group, 1-ethyl-2-methylpropyl group, 1,1,2-trimethylpropyl group, 1-ethylbutyl group, 1-methylbutyl group, 2-methylbutyl group, 1,1-dimethylbutyl group, 1,2-dimethylbutyl group, 2,2-dimethylbutyl group, 1,3-dimethylbutyl group, 2,3-dimethylbutyl group, 2-ethylbutyl group, 2-methylpentyl group, 3-methylpentyl group and the like. Alkenyl and alkynyl groups are preferably "$C_{2-20}$alkenyl" and "$C_{2-20}$alkynyl", more preferably "$C_{2-15}$alkenyl" and "$C_{2-15}$alkynyl", even more preferably "$C_{2-12}$alkenyl" and "$C_{2-12}$alkynyl", even more preferably "$C_{2-10}$alkenyl" and "$C_{2-10}$alkynyl", even more preferably "$C_{2-8}$alkenyl" and "$C_{2-8}$alkynyl", most preferably "$C_{2-6}$alkenyl" and "$C_{2-6}$alkynyl" groups respectively.

A heteroaliphatic group is an aliphatic group as described above, which additionally contains one or more heteroatoms. Heteroaliphatic groups therefore preferably contain from 2 to 21 atoms, preferably from 2 to 16 atoms, more preferably from 2 to 13 atoms, more preferably from 2 to 11 atoms, more preferably from 2 to 9 atoms, even more preferably from 2 to 7 atoms, wherein at least one atom is a carbon atom. Particularly preferred heteroatoms are selected from O, S, N, P and Si. When heteroaliphatic groups have two or more heteroatoms, the heteroatoms may be the same or different.

An alicyclic group is a saturated or partially unsaturated cyclic aliphatic monocyclic or polycyclic (including fused, bridging and spiro-fused) ring system which has from 3 to 20 carbon atoms, that is an alicyclic group with 3, 4, 5, 6, 7, 8, 9, 10, 11, 12, 13, 14, 15, 16, 17, 18, 19 or 20 carbon atoms. Preferably, an alicyclic group has from 3 to 15, more preferably from 3 to 12, even more preferably from 3 to 10, even more preferably from 3 to 8 carbon atoms. The term "alicyclic" encompasses cycloalkyl, cycloalkenyl and cycloalkynyl groups. It will be appreciated that the alicyclic group may comprise an alicyclic ring bearing one or more linking or non-linking alkyl substitutents, such as —$CH_2$-cyclohexyl.

Cycloalkyl, cycloalkenyl and cycloalkynyl groups have from 3 to 20 carbon atoms. The cycloalkyl, cycloalkenyl and cycloalkynyl groups therefore have 3, 4, 5, 6, 7, 8, 9, 10, 11, 12, 13, 14, 15, 16, 17, 18, 19 or 20 carbon atoms. Cycloalkyl, cycloalkenyl and cycloalkynyl groups preferably have from 3 to 15, more preferably from 3 to 12, even more preferably from 3 to 10, even more preferably from 3 to 8 carbon atoms.

When an alicyclic group has from 3 to 8 carbon atoms, this means that the alicyclic group has 3, 4, 5, 6, 7 or 8 carbon atoms. Specifically, examples of the $C_{3-20}$ cycloalkyl group include cyclopropyl, cyclobutyl, cyclopentyl, cyclohexyl, cycloheptyl, adamantyl and cyclooctyl.

A heteroalicyclic group is an alicyclic group as defined above which has, in addition to carbon atoms, one or more ring heteroatoms, which are preferably selected from O, S, N, P and Si. Heteroalicyclic groups preferably contain from one to four heteroatoms, which may be the same or different. Heterocyclic groups preferably contain from 5 to 20 atoms, more preferably from 5 to 14 atoms, even more preferably from 5 to 12 atoms.

An aryl group is a monocyclic or polycyclic ring system having from 5 to 20 carbon atoms. An aryl group is preferably a "$C_{6-12}$ aryl group" and is an aryl group constituted by 6, 7, 8, 9, 10, 11 or 12 carbon atoms and includes condensed ring groups such as monocyclic ring group, or bicyclic ring group and the like. Specifically, examples of "$C_{6-10}$ aryl group" include phenyl group, biphenyl group, indenyl group, naphthyl group or azulenyl group and the like. It should be noted that condensed rings such as indan and tetrahydro naphthalene are also included in the aryl group.

A heteroaryl group is an aryl group having, in addition to carbon atoms, from one to four ring heteroatoms which are preferably selected from O, S, N, P and Si. A heteroaryl group preferably has from 5 to 20, more preferably from 5 to 14 ring atoms. Specifically, examples of a heteroaryl group includes pyridine, imidazole, N-methylimidazole and 4-dimethylaminopyridine.

Examples of alicyclic, heteroalicyclic, aryl and heteroaryl groups include but are not limited to cyclohexyl, phenyl, acridine, benzimidazole, benzofuran, benzothiophene, benzoxazole, benzothiazole, carbazole, cinnoline, dioxin, dioxane, dioxolane, dithiane, dithiazine, dithiazole, dithiolane, furan, imidazole, imidazoline, imidazolidine, indole, indoline, indolizine, indazole, isoindole, isoquinoline, isoxazole, isothiazole, morpholine, napthyridine, oxazole, oxadiazole, oxathiazole, oxathiazolidine, oxazine, oxadiazine, phenazine, phenothiazine, phenoxazine, phthalazine, piperazine, piperidine, pteridine, purine, pyran, pyrazine, pyrazole, pyrazoline, pyrazolidine, pyridazine, pyridine, pyrimidine, pyrrole, pyrrolidine, pyrroline, quinoline, quinoxaline, quinazoline, quinolizine, tetrahydrofuran, tetrazine, tetrazole, thiophene, thiadiazine, thiadiazole, thiatriazole, thiazine, thiazole, thiomorpholine, thianaphthalene, thiopyran, triazine, triazole, and trithiane.

The term "halide" or "halogen" are used interchangeably and, as used herein mean a fluorine atom, a chlorine atom, a bromine atom, an iodine atom and the like, preferably a fluorine atom, a bromine atom or a chlorine atom, and more preferably a fluorine atom or a bromine atom.

A haloalkyl group is preferably a "$C_{1-20}$ haloalkyl group", more preferably a "$C_{1-15}$ haloalkyl group", more preferably a "$C_{1-12}$ haloalkyl group", more preferably a "$C_{1-10}$ haloalkyl group", even more preferably a "$C_{1-8}$ haloalkyl group", even more preferably a "$C_{1-6}$ haloalkyl group" and is a $C_{1-20}$ alkyl, a $C_{1-5}$ alkyl, a $C_{1-12}$ alkyl, a $C_{1-10}$ alkyl, a $C_{1-8}$ alkyl, or a $C_{1-6}$ alkyl group, respectively, as described above substituted with at least one halogen atom, preferably 1, 2 or 3 halogen atom(s). Specifically, examples of "$C_{1-20}$ haloalkyl group" include fluoromethyl group, difluoromethyl group, trifluoromethyl group, fluoro ethyl group, difluro ethyl group, trifluoroethyl group, chloromethyl group, bromomethyl group, iodomethyl group and the like.

An alkoxy group is preferably a "$C_{1-20}$ alkoxy group", more preferably a "$C_{1-15}$ alkoxy group", more preferably a "$C_{1-12}$ alkoxy group", more preferably a "$C_{1-10}$ alkoxy group", even more preferably a "$C_{1-8}$ alkoxy group", even more preferably a "$C_{1-6}$ alkoxy group" and is an oxy group that is bonded to the previously defined $C_{1-20}$ alkyl, $C_{1-5}$ alkyl, $C_{1-12}$ alkyl, $C_{1-10}$ alkyl, $C_{1-8}$ alkyl, or $C_{1-6}$ alkyl group respectively. Specifically, examples of "$C_{1-20}$ alkoxy group" include methoxy group, ethoxy group, n-propoxy group, iso-propoxy group, n-butoxy group, iso-butoxy group, sec-butoxy group, tert-butoxy group, n-pentyloxy group, iso-pentyloxy group, sec-pentyloxy group, n-hexyloxy group, iso-hexyloxy group, n-hexyloxy group, n-heptyloxy group, n-octyloxy group, n-nonyloxy group, n-decyloxy group, n-undecyloxy group, n-dodecyloxy group, n-tridecyloxy group, n-tetradecyloxy group, n-pentadecyloxy group, n-hexadecyloxy group, n-heptadecyloxy group, n-octadecyloxy group, n-nonadecyloxy group, n-eicosyloxy group, 1,1-dimethylpropoxy group, 1,2-dimethylpropoxy group, 2,2-dimethylpropoxy group, 2-methylbutoxy group, 1-ethyl-2-methylpropoxy group, 1,1,2-trimethylpropoxy group, 1,1-dimethylbutoxy group, 1,2-dimethylbutoxy group, 2,2-dimethylbutoxy group, 2,3-dimethylbutoxy group, 1,3-dimethylbutoxy group, 2-ethylbutoxy group, 2-methylpentyloxy group, 3-methylpentyloxy group and the like.

An alkylthio group is preferably a "$C_{1-20}$ alkylthio group", more preferably a "$C_{1-15}$ alkylthio group", more preferably a "$C_{1-12}$ alkylthio group", more preferably a "$C_{1-10}$ alkylthio group", even more preferably a "$C_{1-8}$ alkylthio group", even more preferably a "$C_{1-6}$ alkylthio group" and is a thio (—S—) group that is bonded to the previously defined $C_{1-20}$ alkyl, $C_{1-15}$ alkyl, $C_{1-12}$ alkyl, $C_{1-10}$ alkyl, $C_{1-8}$ alkyl, or $C_{1-6}$ alkyl group respectively.

An alkylaryl group is preferably a "$C_{6-12}$ aryl $C_{1-20}$ alkyl group", more preferably a preferably a "$C_{6-12}$ aryl $C_{1-16}$ alkyl group", even more preferably a "$C_{6-12}$ aryl $C_{1-6}$ alkyl group" and is an aryl group as defined above bonded at any position to an alkyl group as defined above. The point of attachment of the alkylaryl group to a molecule may be via the alkyl portion and thus, preferably, the alkylaryl group is —$CH_2$-Ph or —$CH_2CH_2$-Ph. An alkylaryl group can also be referred to as "aralkyl".

An ether group is preferably a group $OR_5$ wherein $R_5$ can be an aliphatic, heteroaliphatic, alicyclic, heteroalicyclic, aryl or heteroaryl group as defined above. In certain embodiments, $R_5$ can be an unsubstituted aliphatic, alicyclic or aryl. Preferably, $R_5$ is an alkyl group selected from methyl, ethyl or propyl. A thioether group is preferably a group $SR_5$ wherein $R_5$ is as defined above.

A silyl group is preferably a group —$Si(R_6)_3$, wherein each $R_6$ can be independently an aliphatic, heteroaliphatic, alicyclic, heteroalicyclic, aryl or heteroaryl group as defined above. In certain embodiments, each $R_6$ is independently an unsubstituted aliphatic, alicyclic or aryl. Preferably, each $R_6$ is an alkyl group selected from methyl, ethyl or propyl.

A silyl ether group is preferably a group $OSi(R_6)_3$ wherein each $R_6$ can be independently an aliphatic, heteroaliphatic, alicyclic, heteroalicyclic, aryl or heteroaryl group as defined above. In certain embodiments, each $R_6$ can be independently an unsubstituted aliphatic, alicyclic or aryl. Preferably, each $R_6$ is an alkyl group selected from methyl, ethyl or propyl.

A nitrile group is a group CN.

An imine group is a group —CRNR, preferably a group —$CHNR_7$ wherein $R_7$ is an aliphatic, heteroaliphatic, alicyclic, heteroalicyclic, aryl or heteroaryl group as defined above. In certain embodiments, $R_7$ is unsubstituted aliphatic, alicyclic or aryl. Preferably $R_7$ is an alkyl group selected from methyl, ethyl or propyl.

An acetylide group contains a triple bond —C≡C—$R_9$, preferably wherein $R_9$ can be an aliphatic, heteroaliphatic, alicyclic, heteroalicyclic, aryl or heteroaryl group as defined above. For the purposes of the invention when $R_9$ is alkyl, the triple bond can be present at any position along the alkyl chain. In certain embodiments, $R_9$ is unsubstituted aliphatic, alicyclic or aryl. Preferably $R_9$ is methyl, ethyl, propyl or phenyl.

An amino group is preferably —$NH_2$, —$NHR_{10}$ or —$N(R_{10})_2$ wherein $R_{10}$ can be an aliphatic, heteroaliphatic, alicyclic, heteroalicyclic, a silylalkyl, aryl or heteroaryl group as defined above. It will be appreciated that when the amino group is $N(R_{10})_2$, each $R_{10}$ group can be independently selected from an aliphatic, heteroaliphatic, alicyclic, heteroalicyclic a silylalkyl group, heteroaryl or an aryl group as defined above. In certain embodiments, each $R_{10}$ is independently an unsubstituted aliphatic, alicyclic or aryl. Preferably $R_{10}$ is methyl, ethyl, propyl, $SiMe_3$ or phenyl. Where W of the chain transfer agent is amine, the amine is preferably $NH_2$ or $NHR_{10}$.

An alkylamino group may be a group —$NHR_{10}$ or —$N(R_{10})_2$ as defined above.

An amido group is preferably —$NR_{11}C(O)$— or $C(O)$—$NR_{11}$— wherein $R_{11}$ can be hydrogen, an aliphatic, heteroaliphatic, alicyclic, heteroalicyclic, aryl or heteroaryl group as defined above. In certain embodiments, $R_{11}$ is unsubstituted aliphatic, alicyclic or aryl. Preferably $R_{11}$ is hydrogen, methyl, ethyl, propyl or phenyl.

An ester group is preferably —$OC(O)R_{12}$— or —$C(O)OR_{12}$— wherein $R_{12}$ can be hydrogen, an aliphatic, heteroaliphatic, alicyclic, heteroalicyclic, aryl or heteroaryl group as defined above. In certain embodiments, $R_{12}$ is unsubstituted aliphatic, alicyclic or aryl. Preferably $R_{12}$ is hydrogen, methyl, ethyl, propyl or phenyl.

A sulfoxide or sulfonate group is preferably —$SOR_{13}$ or —$OS(O)_2R_{13}$— wherein $R_{13}$ can be hydrogen, an aliphatic, heteroaliphatic, alicyclic, heteroalicyclic, aryl or heteroaryl group as defined above. In certain embodiments, $R_{13}$ is unsubstituted aliphatic, alicyclic or aryl. Preferably $R_{13}$ is hydrogen, methyl, ethyl, propyl or phenyl.

A carboxylate group is preferably $OC(O)R_{14}$, wherein $R_{14}$ can be hydrogen, an aliphatic, heteroaliphatic, alicyclic, heteroalicyclic, aryl or heteroaryl group as defined above. In certain embodiments, $R_{14}$ is unsubstituted aliphatic, alicyclic or aryl. Preferably $R_{14}$ is hydrogen, methyl, ethyl, propyl, butyl (for example n-butyl, isobutyl or tert-butyl), phenyl, pentafluorophenyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, trifluoromethyl or adamantyl.

An acetamide is preferably $MeC(O)N(R_{15})_2$ wherein $R_{15}$ can be hydrogen, an aliphatic, heteroaliphatic, alicyclic, heteroalicyclic, aryl or heteroaryl group as defined above. In certain embodiments, $R_{15}$ is unsubstituted aliphatic, alicyclic or aryl. Preferably $R_{15}$ is hydrogen, methyl, ethyl, propyl or phenyl.

A phosphinate group is preferably a group —$OP(O)(R_{16})_2$ wherein each $R_{16}$ is independently selected from hydrogen, or an aliphatic, heteroaliphatic, alicyclic, heteroalicyclic, aryl or heteroaryl group as defined above. In certain embodiments, $R_{16}$ is aliphatic, alicyclic or aryl, which are optionally substituted by aliphatic, alicyclic, aryl or $C_{1-6}$alkoxy. Preferably $R_{16}$ is optionally substituted aryl or $C_{1-20}$ alkyl, more preferably phenyl optionally substituted by $C_{1-6}$ alkoxy (preferably methoxy) or unsubstituted $C_{1-20}$alkyl (such as hexyl, octyl, decyl, dodecyl, tetradecyl, hexadecyl, stearyl).

A sulfinate group is preferably —$OSOR_{17}$ wherein $R_{17}$ can be hydrogen, an aliphatic, heteroaliphatic, haloaliphatic, alicyclic, heteroalicyclic, aryl or heteroaryl group as defined above. In certain embodiments, $R_{17}$ is unsubstituted aliphatic, alicyclic or aryl. Preferably $R_{17}$ is hydrogen, methyl, ethyl, propyl or phenyl.

It will be appreciated that where any of the above groups are present in a Lewis base G, one or more additional R groups may be present, as appropriate, to complete the valency. For example, in the context of an ether an additional R group may be present to give $ROR_5$, wherein R is hydrogen, an optionally substituted aliphatic, heteroaliphatic, alicyclic, heteroalicyclic, aryl or heteroaryl group as defined above. Preferably, R is hydrogen or aliphatic, alicyclic or aryl.

Any of the aliphatic, heteroaliphatic, alicyclic, heteroalicyclic, aryl, heteroaryl, haloalkyl, alkoxy, alkylthio, alkylaryl, ether, ester, sulfoxide, sulfonate, carboxylate, silyl ether, imine, acetylide, amino, alkylamino or amido groups wherever mentioned in the definitions above, may optionally be substituted by halogen, hydroxyl, nitro, carbonate, alkoxy, aryloxy, heteroaryloxy, amino, alkylamino, imine, nitrile, acetylide, or optionally substituted aliphatic, heteroaliphatic, alicyclic, heteroalicyclic, aryl or heteroaryl groups (for example, optionally substituted by halogen, hydroxyl, nitro, carbonate, alkoxy, amino, alkylamino, imine, nitrile or acetylide).

Exemplary diols or polyols include diols (for example, 1,2-ethanediol, 1-2-propanediol, 1,3-propanediol, 1,2-butanediol, 1-3-butanediol, 1,4-butanediol, 1,5-pentanediol, 1,6-hexanediol, 1,2-diphenol, 1,3-diphenol, 1,4-diphenol, catechol and cyclohexenediol), triols (for example glycerol, benzenetriol, cyclohexanetriol, tris(methylalcohol)propane, tris(methylalcohol)ethane, tris(methylalcohol)nitropropane), tetraols (for example, calix[4]arene, 2,2-bis(methylalcohol)-1,3-1,3-propanediol) and polyols (for example poly (ethylene glycol), D-(+)-glucose and D-sorbitol).

It will be appreciated that although in formulae (I) and (III), the groups X and G are illustrated as being associated with a single M metal centre, one or more X and G groups may form a bridge between the two M metal centres.

For the purposes of the present invention, the epoxide substrate is not limited. The term epoxide therefore relates to any compound comprising an epoxide moiety. Preferred examples of epoxides for the purposes of the present invention include cyclohexene oxide, styrene oxide, propylene oxide, substituted cyclohexene oxides (such as limonene oxide, $C_{10}H_{16}O$ or 2-(3,4-epoxycyclohexyl)ethyltrimethoxysilane, $C_{11}H_{22}O$), alkylene oxides (such as ethylene oxide and substituted ethylene oxides) or substituted oxiranes (such as epichlorohydrin, 1,2-epoxybutane, glycidyl ethers). The epoxide preferably has a purity of at least 98%, more preferably >99%.

DETAILED DESCRIPTION

In the first aspect of the invention, there is provided a process for the synthesis of a polycarbonate, the process comprising the step of reacting carbon dioxide with at least one epoxide in the presence of a catalyst of formula (I):

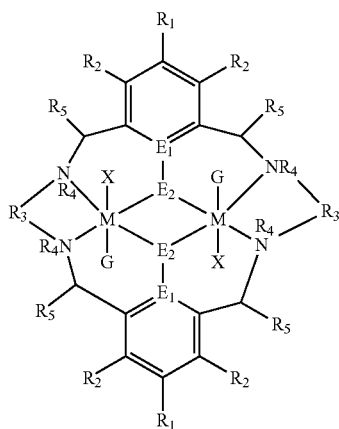

(I)

wherein R₁ and R₂ are independently hydrogen, halide, a nitro group, a nitrile group, an imine, an amine, an ether group, a silyl ether group, or an acetylide group or an optionally substituted alkyl, alkenyl, alkynyl, haloalkyl, aryl, heteroaryl, alicyclic or heteroalicyclic;

R₃ is optionally substituted alkylene, alkenylene, alkynylene, heteroalkylene, heteroalkenylene, heteroalkynylene, arylene, heteroarylene or cycloalkylene, wherein alkylene, alkenylene, alkynylene, heteroalkylene, heteroalkenylene or heteroalkynylene may optionally be interrupted by aryl, heteroaryl, alicyclic or heteroalicyclic;

R₄ is hydrogen, or optionally substituted aliphatic, heteroaliphatic, alicyclic, heteroalicyclic, aryl, heteroaryl, alkylheteroaryl or alkylaryl;

R₅ is H, or optionally substituted aliphatic, heteroaliphatic, alicyclic, heteroalicyclic, aryl, heteroaryl, alkylheteroaryl or alkylaryl;

E₁ is C, E₂ is O, S or NH or E₁ is N and E₂ is O;

X is OC(O)R$^x$, OSO₂R$^x$, OSO(R$^x$)₂, OS(O)R$^x$, OR$^x$, phosphinate, halide, nitrate, hydroxyl, carbonate, amido or optionally substituted aliphatic, heteroaliphatic, alicyclic, heteroalicyclic, aryl or heteroaryl;

R$_x$ is independently hydrogen, or optionally substituted aliphatic, haloaliphatic, heteroaliphatic, alicyclic, heteroalicyclic, aryl, alkylaryl or heteroaryl;

each G is independently absent or a neutral or anionic donor ligand which is a Lewis base;

M is Zn(II), Cr(II), Co(II), Mn(II), Mg(II), Fe(II), Ti(II), Cr(III)-X, Co(III)-X, Mn(III)-X, Fe(III)-X, Ca(II), Ge(II), Al(III)-X, Ti(III)-X, V(III)-X, Ge(IV)-(X)₂ or Ti(IV)-(X)₂;

and a chain transfer agent selected from water or a compound of formula (II):

$$Z{-\!\!\!\!-}(W)_n \qquad (II)$$

wherein

Z is an optionally substituted moiety selected from the group consisting of aliphatic, heteroaliphatic, alicyclic, heteroalicyclic, aryl, heteroaryl, polyolefin, polyester, polyether, polycarbonate or combinations thereof, each W is independently selected from a hydroxyl, amine, thiol or carboxylate group, and n is an integer which is at least 1.

It will be appreciated that for the catalysts useful in the first aspect of the invention, the groups R₁ and R₂ may be the same or different. R₁ and R₂ are preferably independently selected from hydrogen, tBu, Me, CF₃, phenyl, F, Cl, Br, I, NMe₂, NEt₂, NO₂, OMe, OSiEt₃, CNMe, CN or CCPh, more preferably hydrogen, OMe, Me, NO₂, halogen or tBu (e.g. hydrogen or tBu). In certain embodiments, R₂ is hydrogen and R₁ is any one of the groups defined above, preferably NO₂, halogen, tBu, OMe or Me, more preferably tBu, OMe or Me.

It will be appreciated that the group R₃ is a disubstituted alkyl, alkenyl, alkynyl, heteroalkyl, heteroalkenyl or heteroalkynyl group which may optionally be interrupted by an aryl, heteroaryl, alicyclic or heteroalicyclic group, or may be a disubstituted aryl or cycloalkyl group which acts as a bridging group between two nitrogen centres in the catalyst of formula (I). Thus, where R₃ is a alkylene group, such as dimethylpropylene, the R₃ group has the structure —CH₂—C(CH₃)₂—CH₂—. The definitions of the alkyl, aryl, cycloalkyl etc groups set out above therefore also relate respectively to the alkylene, arylene, cycloalkylene etc groups set out for R₃. Preferably R₃ is ethylene, 2,2-dimethylpropylene, propylene, butylene, phenylene, cyclohexylene or biphenylene, more preferably 2,2-dimethylpropylene. When R₃ is cyclohexylene, it can be the racemic, RR- or SS-forms.

Preferably R₄ is independently selected from hydrogen, or optionally substituted alkyl, alkenyl, alkynyl, aryl, heteroalkyl, heteroalkenyl, heteroalkynyl, heteroaryl or alkylheteroaryl. More preferably, R₄ is independently selected from hydrogen, or optionally substituted alkyl, alkenyl, alkynyl, aryl, heteroalkyl, heteroalkenyl, heteroalkynyl or heteroaryl. Exemplary options for R₄ include H, Me, Et, Bn, iPr, tBu or Ph. A further exemplary option is —CH₂-(2-pyridine). R₄ is preferably hydrogen.

Preferably R₅ is independently selected from hydrogen, or optionally substituted aliphatic or aryl. More preferably, R₅ is selected from hydrogen, alkyl or aryl. Exemplary R₅ groups include hydrogen, methyl, ethyl, phenyl and trifluoromethyl, preferably hydrogen, methyl or trifluoromethyl. In particularly preferred embodiments, R₅ is hydrogen.

It will be appreciated that X acts as the initiating species for the process of the first aspect. Each X is independently selected from OC(O)R$^x$, OSO₂R$^x$, OS(O)R$^x$, OSO(R$^x$)₂, OR$^x$, phosphinate, halide, nitrate, hydroxyl, carbonate, amido or optionally substituted aliphatic, heteroaliphatic (for example silyl), alicyclic, heteroalicyclic, aryl or heteroaryl. In certain embodiments, each X is independently OC(O)R$^x$, OSO₂R$^x$, OSO(R$^x$)₂, OR$^x$, halide, nitrate, hydroxyl, carbonate, amido or optionally substituted aliphatic, heteroaliphatic (for example silyl), alicyclic, heteroalicyclic, aryl or heteroaryl. R$_x$ is independently hydrogen, or optionally substituted aliphatic, haloaliphatic, heteroaliphatic, alicyclic, heteroalicyclic, aryl, alkylaryl or heteroaryl. Preferably, X is OC(O)R$^x$ or OR$^x$. Preferably, R$_x$ is independently hydrogen, optionally substituted aliphatic, haloaliphatic, aryl, heteroaryl, silyl, or alkylaryl. Exemplary options for X include OCOCH₃, OCOCF₃, OSO₂C₇H₇, OSO(CH₃)₂, Et, Me, PhOEt, OMe, OiPr, OtBu, Cl, Br, I, F, N(iPr)₂, N(SiMe₃)₂, hexanoate, octanoate, decanoate, dodecanoate, stearate, pivalate, adamantyl carboxylate, benzoate, pentafluorobenzoate, dioctyl phosphinate, diphenyl phosphinate and bis(4-methoxy)phenylphosphinate. Preferred exemplary options for X include OCOCH₃, OCOCF₃, OSO₂C₇H₇, OSO(CH₃)₂, Et, Me, PhOEt, OMe, OiPr, OtBu, Cl, Br, I, F, N(iPr)₂ or N(SiMe₃)₂.

When G is not absent, it is a group which is capable of donating a lone pair of electrons (i.e. a Lewis base). In certain embodiments, G is a nitrogen containing Lewis base. Each G may be neutral or negatively charged. If G is negatively charged, then one or more positive counterions will be required to balance out the charge of the complex. Suitable positive counterions include group 1 metal ions (Na⁺, K⁺, etc), group 2 metal ions ($Mg^{2+}$, $Ca^{2+}$, etc), imidazolium ions, a positively charged optionally substituted heteroaryl, heteroaliphatic or heteroalicyclic group, ammonium ions (i.e. $N(R^{12})_4^+$), iminium ions (i.e. $(R^{12})_2C=N(R^{12})_2^+$, such as bis(triphenylphosphine)iminium ions) or phosphonium ions ($P(R^{12})_4^+$), wherein each $R^{12}$ is independently selected from hydrogen or optionally substituted aliphatic, heteroaliphatic, alicyclic, heteroalicyclic, aryl or heteroaryl. Exemplary counterions include $[H—B]^+$ wherein B is selected from triethylamine, 1,8-diazabicyclo[5.4.0]undec-7-ene and 7-methyl-1,5,7-triazabicyclo[4.4.0]dec-5-ene.

G is preferably independently selected from an optionally substituted heteroaliphatic group, an optionally substituted heteroalicyclic group, an optionally substituted heteroaryl group, a halide, hydroxide, hydride, a carboxylate and water. More preferably, G is independently selected from water, an alcohol, a substituted or unsubstituted heteroaryl (imidazole, methyl imidazole (for example, N-methyl imidazole), pyridine, 4-dimethylaminopyridine, pyrrole, pyrazole, etc), an ether (dimethyl ether, diethylether, cyclic ethers, etc), a thioether, carbene, a phosphine, a phosphine oxide, a substituted or unsubstituted heteroalicyclic (morpholine, piperidine, tetrahydrofuran, tetrahydrothiophene, etc), an amine, an alkyl amine trimethylamine, triethylamine, etc), acetonitrile, an ester (ethyl acetate, etc), an acetamide (dimethylacetamide, etc), a sulfoxide (dimethylsulfoxide, etc), a carboxylate, a hydroxide, hydride, a halide, a nitrate, a sulfonate, etc. In some embodiments, one or both instances of G is independently selected from optionally substituted heteroaryl, optionally substituted heteroaliphatic, optionally substituted heteroalicyclic, halide, hydroxide, hydride, an ether, a thioether, carbene, a phosphine, a phosphine oxide, an amine, an alkyl amine, acetonitrile, an ester, an acetamide, a sulfoxide, a carboxylate, a nitrate or a sulfonate. In certain embodiments, G may be a halide; hydroxide; hydride; water; a heteroaryl, heteroalicyclic or carboxylate group which are optionally substituted by alkyl, alkenyl, alkynyl, alkoxy, halogen, hydroxyl, nitro or nitrile. In preferred embodiments, G is independently selected from halide; water; a heteroaryl optionally substituted by alkyl (e.g. methyl, ethyl etc), alkenyl, alkynyl, alkoxy (preferably methoxy), halogen, hydroxyl, nitro or nitrile. In some embodiments, one or both instances of G is negatively charged (for example, halide). In further embodiments, one or both instances of G is an optionally substituted heteroaryl. Exemplary G groups include chloride, bromide, pyridine, methylimidazole (for example N-methyl imidazole) and dimethylaminopyridine (for example, 4-methylaminopyridine).

It will be appreciated that when a G group is present, the G group may be associated with a single M metal centre as shown in formula (I), or the G group may be associated with both metal centres and form a bridge between the two metal centres, as shown below in formula (Ia):

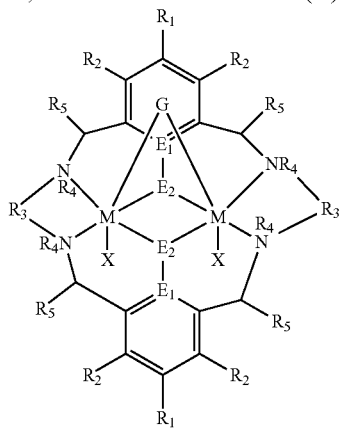

(Ia)

Wherein $R_1$, $R_2$, $R_3$, $R_4$, $R_5$, M, G, X, $E_1$ and $E_2$ are as defined for formula (I).

Preferably M is Zn(II), Cr(III), Cr(II), Co(III), Co(II), Mn(III), Mn(II), Mg (II), Ti(II), Fe(II), Fe(III), Ca(II), Ge(II), Al(III), Ti(III), V(III), Ge(IV) or Ti(IV), more preferably Zn(II), Cr(III), Co(II), Mn(II), Mg(II), Fe(II) or Fe(III), and most preferably Zn(II) or Mg(II). It will be appreciated that when M is Cr(III), Co(III), Mn(III) or Fe(III), the catalyst of formula (I) will contain an additional X group co-ordinated to the metal centre, wherein X is as defined above. It will also be appreciated that when M is Ge(IV) or Ti(IV), the catalyst of formula (I) will contain two additional X group co-ordinated to the metal centre, wherein X is as defined above. In certain embodiments, when M is Ge(IV) or Ti(IV), both G may be absent.

The skilled person will also appreciate that each M may be the same (for example, both M may be Mg, Zn, Fe or Co) or each M may be different and can be present in any combination (for example, Fe and Zn, Co and Zn, Mg and Fe, Co and Fe, Mg and Co, Cr and Mg, Cr and Zn, Mn and Mg, Mn and Zn, Mn and Fe, Cr and Fe, Cr and Co, Al and Mg, Al and Zn etc). When M is the same metal, it will be appreciated that each M may be in the same oxidation state (for example both M may be Co(II), Fe(II) or Fe(III)), or in a different oxidation state (for example, one M may be Co(II) and the other M may be Co(III), one M may be Fe(II) and the other M may be Fe(III), or one M may be Cr(II) and the other M may be Cr(III)).

In certain embodiments of the first aspect, the catalyst is selected from:

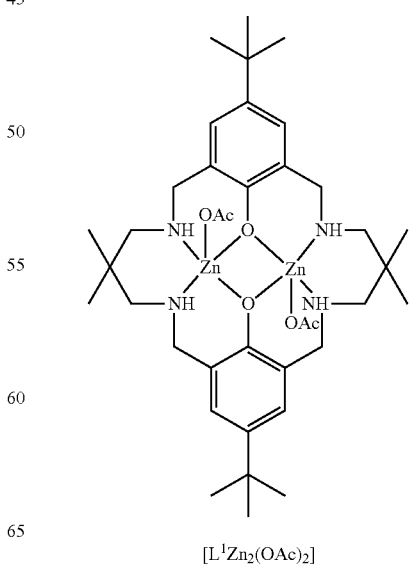

[$L^1Zn_2(OAc)_2$]

-continued

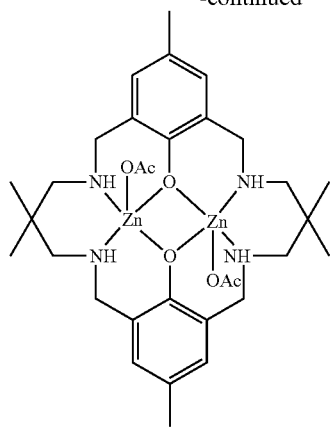

[L²Zn₂(OAc)₂]

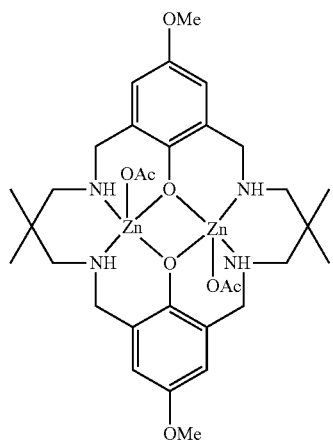

[L³Zn₂(OAc)₂]

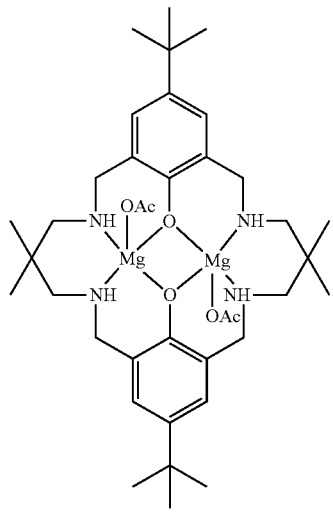

L¹Mg₂(OAc)₂]

-continued

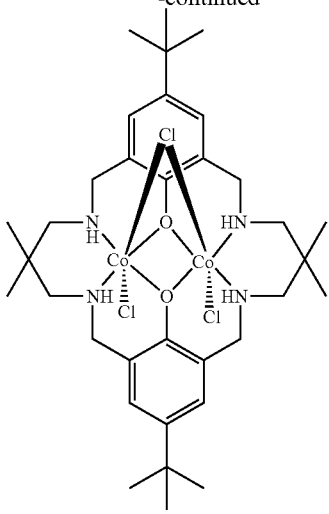

[L¹Co₂Cl₃]⁻[B-H]⁺

[B-H]⁺ represents any counterion, for example,
B may be NEt₃, 1,8-diazabicyclo[5.4.0]undec-7-ene (DBU),
7-methyl-1,5,7-triazabicyclo[4.4.0]dec-5-ene (MTBD), etc

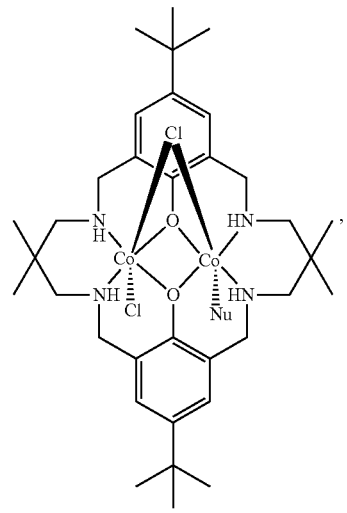

[L¹Co₂Cl₂Nu]

Nu = N-methylimidazole
= pyridine
= dimethylaminopyridine

[L¹Mg₂Cl₂(methylimidazole)],
[L₁Mg₂Cl₂(dimethylaminopyridine)],
[L¹Mg₂Br₂(dimethylaminopyridine)],
[L¹Zn₂(F₃CCOO)₂],
[L¹Zn₂(OOCC(CH₃)₃)₂],
[L¹Zn₂(OC₆H₅)₂],
[L¹Fe₂Cl₄],
[L¹Co₂(OAc)₃],
[L⁴Mg₂(OAc)₂],
[L¹Zn₂(adamantyl carbonate)₂],
[L¹Zn₂(pentafluorobenzoate)₂],
[L¹Zn₂(diphenylphosphinate)₂],
[L¹Zn₂(bis(4-methoxy)phenyl phosphinate)₂],
[L¹Zn₂(hexanoate)₂],
[L¹Zn₂(octanoate)₂],

[L¹Zn₂(dodecanoate)₂],
[L¹Mg₂(F₃CCOO)₂], and
[L¹Mg₂Br₂].

In other embodiments of the first aspect, the catalyst is selected from:
[L¹Zn₂(OAc)₂]
[L²Zn₂(OAc)₂]
[L³Zn₂(OAc)₂]
[L¹Mg₂(OAc)₂]
[L¹Mg₂Cl₂(methylimidazole)],
[L₁Mg₂Cl₂(dimethylaminopyridine)],
[L₁Mg₂Br₂(dimethylaminopyridine)],
[L¹Zn₂(F₃CCOO)₂],
[L¹Zn₂(OOCC(CH₃)₃)₂],
[L¹Zn₂(OC₆H₅)₂],

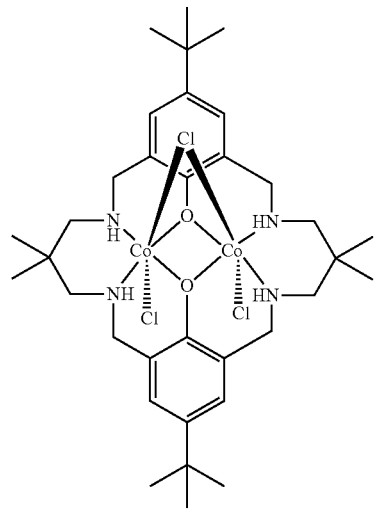

[L¹Co₂Cl₃]⁻ [B—H]⁺

[B—H]⁺ represents any counterion, for example,
B may be NEt₃, 1,8-diazabicyclo[5.4.0]undec-7-ene (DBU),
7-methyl-1,5,7-triazabicyclo[4.4.0]dec-5-ene (MTBD), etc and

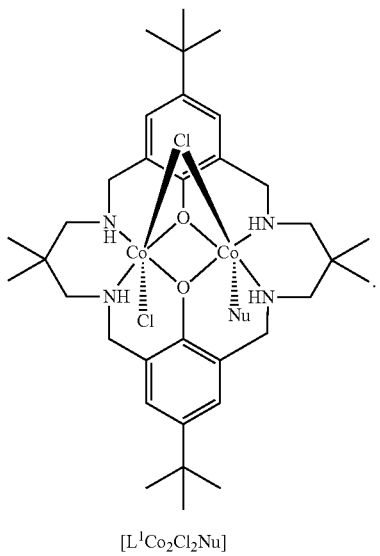

[L¹Co₂Cl₂Nu]

Nu = N-methylimidazole
  = pyridine
  = dimethylaminopyridine

In certain embodiments, the catalyst (I) is a catalyst of formula (III) as defined in respect of the sixth aspect of the invention.

The chain transfer agent (CTA) may be water or a compound which has one or more, for example, two or more groups independently selected from hydroxyl (—OH), amine (—NHR$^W$), thiol (—SH) or carboxylate (—C(O)OH), wherein R$^W$ is hydrogen, optionally substituted aliphatic, heteroaliphatic, alicyclic, heteroalicyclic, aryl or heteroaryl, or combinations thereof (i.e. aliphaticaryl, aliphaticheteroaryl, heteroaliphaticaryl, etc). It will be appreciated that water, which does not have two distinct "—OH" groups, displays similar chain transfer properties to molecules which do have two distinct "—OH" groups.

The chain transfer agent useful in the process of the first aspect is either water or a compound which can be represented by the following formula:

$$Z\text{-}(W)_n \qquad (II).$$

Each W is independently selected from hydroxyl (—OH), amine (—NHR$^W$), thiol (—SH) or carboxylic acid (—C(O)OH).

Z is the core of the chain transfer agent any may be any group which can have one or more, preferably two or more "W" groups attached to it. In preferred embodiments, Z is an optionally substituted moiety selected from the group consisting of aliphatic, heteroaliphatic, alicyclic, heteroalicyclic, aryl, heteroaryl, polyolefin, polyester, polyether, polycarbonate or combinations thereof. For example, Z may be an optionally substituted araliphatic, heteroaraliphatic, aliphaticalicyclic etc. group. Preferably Z is selected from alkyl, heteroalkyl, alkenyl, heteroalkenyl, alkynyl, heteroalkynyl, cycloalkyl, heterocycloalkyl, aryl, heteroaryl and polyether.

When Z is a polymer (i.e. when Z comprises a polyolefin, polyester, polyether or polycarbonate group), the molecular weight ($M_n$) of such polymers are preferably less than 10,000 g/mol. Preferred polymers include poly(ethylene glycol) (PEG) and poly(lactic acid) (PLA).

The chain transfer agent, in particular the group Z, may optionally be substituted. In certain embodiments, Z is optionally substituted by halogen, nitrile, imine, nitro, aliphatic, acetyl, amido, heteroaliphatic, alicyclic, heteroalicyclic, aryl or heteroaryl.

n is an integer which is at least 1. In preferred embodiments, n is an integer selected from 1 to 10 inclusive (i.e. n can be 1, 2, 3, 4, 5, 6, 7, 8, 9 or 10), preferably from 2 to 10 inclusive. More preferably, n is an integer selected from 1 to 6 inclusive, even more preferably from 2 to 6 inclusive.

In certain embodiments, each occurrence of W may be the same or different. In other embodiments, each occurrence of W is hydroxyl (i.e. the chain transfer agent is an alcohol, which is intended to cover a chain transfer agent with one OH group, or a chain transfer agent with two or more OH groups, in other words, a polyol, for example a diol, a triol, a tetraol etc.). In other embodiments, each occurrence of W is amine (i.e. the chain transfer agent is an amine which is intended to cover chain transfer agents with one amine group, or chain transfer agents with two or more amine groups, in other words a polyamine, for example a diamine, a triamine, a tetraamine etc.). In other embodiments, each occurrence of W is carboxylic acid (i.e. the chain transfer agent may comprise one carboxylic acid group, or two or more carboxylic acid groups, in other words, the chain transfer agent may be a polycarboxylic acid, for example a diacid, a triacid, a tetraacid etc.). In other embodiments, each occurrence of W is thiol (i.e. the chain transfer agent may comprise one thiol group, or two or more thiol groups, in other words, the chain transfer agent may be a polythiol, for example a dithol, a trithiol, a tetrathiol etc.). In other embodiments, the chain transfer agent is water.

In certain embodiments of the first aspect, when the chain transfer agent is water, X is not $OCOCH_3$, $OCOCF_3$, $OSO_2C_7H_7$, $OSO(CH_3)_2$, or halide. In certain other embodiments of the first aspect, when the chain transfer agent is water, X is not $OCOCH_3$, $OCOCF_3$, $OSO_2C_7H_7$, $OSO(CH_3)_2$, halide, alkyl, alkoxy or amido. In certain other embodiments of the first aspect, when the chain transfer agent is water, the catalyst of formula (I) is a catalyst of formula (III) as described below in respect of the sixth aspect of the invention.

In certain embodiments of the first aspect, a single chain transfer agent is used. In other embodiments, a mixture of chain transfer agents is used.

Examples of chain transfer agents useful in the present invention include water, mono-alcohols (i.e. alcohols with one OH group, for example, diphenylphosphinic acid, 4-ethylbenzenesulfonic acid, methanol, ethanol, propanol, butanol, pentanol, hexanol, phenol, cyclohexanol), diols (for example, 1,2-ethanediol, 1-2-propanediol, 1,3-propanediol, 1,2-butanediol, 1-3-butanediol, 1,4-butanediol, 1,5-pentanediol, 1,6-hexanediol, 1,2-diphenol, 1,3-diphenol, 1,4-diphenol, catechol and cyclohexenediol), triols (glycerol, benzenetriol, 1,2,4-butanetriol, tris(methylalcohol)propane, tris(methylalcohol)ethane, tris(methylalcohol)nitropropane, preferably glycerol or benzenetriol), tetraols (for example, calix [4] arene, 2,2-bis(methylalcohol)-1,3-propanediol, preferably calix[4]arene), polyols (for example, D-(+)-glucose or D-sorbitol), dihydroxy terminated polyesters (for example polylactic acid), dihydroxy terminated polyethers (for example poly(ethylene glycol)), starch, lignin, mono-amines (i.e. amines with one $NHR^W$ group, for example, methylamine, dimethylamine, ethylamine, diethylamine, propylamine, dipropylamine, butylamine, dibutylamine, pentylamine, dipentylamine, hexylamine, dihexylamine), diamines (for example 1,4-butanediamine), triamines, diamine terminated polyethers, diamine terminated polyesters, mono-carboxylic acids (for example, 3,5-di-tert-butyl-benzoic acid), dicarboxylic acids (for example, maleic acid, malonic acid, succinic acid, glutaric acid or terephthalic acid, preferably maleic acid, malonic acid, succinic acid, glutaric acid), tricarboxylic acids (for example, citric acid, 1,3,5-benzenetricarboxylic acid or 1,3,5-cyclohexanetricarboxylic acid, preferably citric acid), mono-thiols, dithoils, trithiols, and compounds having a mixture of hydroxyl, amine, carboxylic acid and thiol groups, for example lactic acid, glycolic acid, 3-hydroxypropionic acid, natural amino acids, unnatural amino acids, monosaccharides, disaccharides, oligosaccharides and polysaccharides (including pyranose and furanose forms). In certain embodiments, the chain transfer agent is selected from cyclohexene diol, 1,2,4-butanetriol, tris(methylalcohol)propane, tris(methylalcohol)nitropropane, tris(methylalcohol)ethane, 2,2-bis(methylalcohol)-1, 3-propanediol, 1,3,5-benzenetricarboxylic acid, diphenylphosphinic acid, 1,3,5-cyclohexanetricarboxylic acid, 1,4-butanediamine, 1,6-hexanediol, D-sorbitol, 1-butylamine, terephthalic acid, D-(+)-glucose, 3,5-di-tert-butyl-benzoic acid, 4-ethylbenzenesulfonic acid and water.

In one embodiment of the first aspect, the chain transfer agent is not water. In an alternative embodiment of the first aspect, the chain transfer agent is water. It was found that both the metal centres and the ligand set of the catalysts used in the process of the first aspect are hydrolytically stable (i.e. do not degrade in the presence of water). Water functions extremely well as a chain transfer agent for the process of the first aspect and is cheap and readily available. Furthermore, it is not necessary to ensure that all reagents, such as monomers (including the carbon dioxide) and solvents are entirely free of water before beginning the reaction. This avoids lengthy and costly purification steps of reagents such as carbon dioxide, which are frequently contaminated with water (particularly carbon dioxide captured from industrial sources). In fact, as mentioned above, water impurities in the monomers, solvents etc can provide the entire amount of chain transfer agent necessary to convert all of the end groups of the polycarbonates produced by the first aspect to hydroxyl groups. When the chain transfer agent is water, it may be present in a molar ratio of less than 1:1 relative to the metal complex (for example, as an impurity in the reagents which will be used during the polymerisation process), in a molar ratio of about 1:1 relative to the metal complex, or in a molar ratio of greater than 1:1 (such as at least 2:1, at least 4:1 or at least 8:1) relative to the metal complex (i.e. in excess of the metal complex). In certain embodiments, the water will be present in a molar ratio from about 1:1 to about 128:1, from about 2:1 to about 64:1, from about 4:1 to about 32:1, or from about 8:1 to about 16:1 relative to the metal complex.

In certain embodiments, the catalyst is selected from $[L^1Zn_2(OAc)_2]$, $[L^1Zn_2(OC(O)CF_3)_2]$, $[L^1Mg_2(OAc)_2]$ and $[L^1Mg_2(OC(O)CF_3)_2]$ (preferably $[L^1Zn_2(OAc)_2]$, $[L^1Zn_2(OC(O)CF_3)_2]$ and $[L^1Mg_2(OC(O)CF_3)_2]$), the chain transfer agent is water and is present in a molar ratio of at least 1:1 relative to the metal complex. For example, water may be present in a molar ratio from about 1:1 to 128:1, such as from about 2:1 to 64:1, for example from about 4:1 to 32:1, e.g. from about 8:1 to 16:1 relative to the metal complex.

In certain embodiments with any one of the chain transfer agents mentioned above, the chain transfer agent is present in a molar ratio of at least 1:1 relative to the metal complex (catalyst (I)). For example, the chain transfer agent is present in a molar ratio of at least 2:1, at least 4:1, at least 8:1, at least 16:1 or at least 32:1 relative to the metal complex. In certain embodiments, the chain transfer agent will be present in a molar ratio from about 1:1 to about 128:1, from about 1:1 to about 100:1 (for example from about 10:1 to about 30:1), from about 2:1 to about 64:1, from about 4:1 to about 32:1, or from about 8:1 to about 16:1 relative to the metal complex. In certain embodiments, the chain transfer agent is present in a molar ratio from 1:1 to 9:1. Preferably, the chain transfer agent is present in a molar ratio of at least 2:1 relative to the metal complex.

A halogenated X group reduces the amount of chain transfer agent required to produce polycarbonate chains which are terminated at both ends with hydroxyl groups. In fact, water impurities which are present either in the carbon dioxide or left over from the production of the catalyst (for example, if hydrated metal acetates are used to produce the catalysts useful in the first aspect), can act as a sufficient amount of chain transfer agent (where the chain transfer agent is water) to ensure that all polycarbonate chains are terminated in hydroxyl groups. An excess of chain transfer agent is not therefore required. Therefore in certain embodiments, X is a halogenated group and the chain transfer agent:metal complex molar ratio is at least 0.1:1, preferably at least 1:1, more preferably 0.1:1 to 9:1, even more preferably 0.1:1 to 1:1. Preferably X is $OC(O)R^x$, $OSO_2R^x$, $OSO(R^x)_2$, $OR^x$, $OSOR^x$, halophosphinate, haloaryl, haloheteroaryl, halohet-eroaliphatic, haloalicyclic, haloheteroalicyclic or haloaliphatic (more preferably $OC(O)R^x$, $OSO_2R^x$, $OSO(R^x)_2$, $OR^x$ or haloaliphatic), wherein one or both $R^x$ groups are haloaliphatic, haloaryl or haloalicyclic more preferably haloaliphatic (such as fluoroaliphatic).

The process of the first aspect may be carried out in the presence of a solvent. Examples of solvents useful in the first aspect include toluene, diethyl carbonate, dimethyl carbonate, dioxane, dichlorobenzene, methylene chloride, propylene carbonate, ethylene carbonate, etc.

The chain transfer agent may be used to control the molecular weight ($M_n$) of the polymers produced by the process of the first aspect. Preferably, the molecular weight ($M_n$) of the polymers produced by the process of the first aspect is from about 1,000 g/mol to about 100,000 g/mol. The molecular weight of the polymers produced by the first aspect can be measured by Gel Permeation Chromatography (GPC) using, for example, a GPC-60 manufactured by Polymer Labs, using THF as the eluent at a flow rate of 1 ml/min on Mixed B columns, manufactured by Polymer Labs. Narrow molecular weight polystyrene standards can be used to calibrate the instrument.

The process of the first aspect may be carried out using any compound comprising an epoxide moiety. In certain embodiments of the first aspect, the epoxide may be purified (for example by distillation, such as over calcium hydride) prior to reaction with carbon dioxide. For example, the epoxide may be distilled prior to being added to the reaction mixture comprising the catalyst and chain transfer agent.

In certain embodiments of the process of the first aspect, the process comprises the intermediate steps of (i) providing a catalyst of formula (I) and an epoxide, (ii) adding a chain transfer agent of formula (II) thereto, and (iii) exposing the catalyst, epoxide and chain transfer agent to carbon dioxide.

The process of the first aspect of the invention may be carried out at a pressure of 1 to 100 atmospheres, preferably at 1 to 10 atmospheres, more preferably at 1 or 2 atmospheres. The catalysts used in the process of the first aspect allow the reaction of carbon dioxide with an epoxide to be carried out at low pressures.

The process of the first aspect of the invention may be carried out at a temperature of about 0° C. to about 120° C., preferably from about 50° C. to about 100° C. The duration of the process may be up to 168 hours preferably 1 to 24 hours.

The process of the first aspect of the invention may be carried out at low catalytic loading, for example, the catalytic loading for the process is preferably in the range of 1:1,000-100,000 catalyst:epoxide, more preferably in the region of 1:1,000-50,000 catalyst:epoxide, even more preferably in the region of 1:1,1000-10,000, and most preferably in the region of 1:10,000 catalyst:epoxide.

It should be noted that the catalysts which are used in the process of the first aspect may operate at remarkably low pressure, e.g. 1 atm of $CO_2$, but they are also active at much higher pressures, e.g., 40 atm $CO_2$.

It will be appreciated that the various features described above for the process of the first aspect may be present in combination mutatis mutandis.

In a second aspect of the invention is provided a polymerisation system for the copolymerisation of carbon dioxide and at least one epoxide comprising a catalyst as defined in the first aspect, and a chain transfer agent as defined in the first aspect. All preferred features of the chain transfer agent and the catalyst as defined in first aspect of the invention apply equally to the second aspect of the invention.

The third aspect of the invention provides a product of the process of the first aspect of the invention. All preferred features of the first aspect of the invention apply to the third aspect of the invention mutatis mutandis.

The fourth aspect of the invention provides a copolymer of formula B-(A)$_n$, wherein B is a polycarbonate, for example, as produced by the process of the first aspect of the invention, A is a further polymeric unit which may differ in structure from B, and n is an integer which is at least 1, preferably at least 2. The architecture of the polycarbonate will depend on the chain transfer agent (CTA) used in its production. For example, if the CTA is a group Z-(W)$_n$ where n is 1, the polycarbonate will be linear, terminated with a hydroxyl group at one end only. If the CTA is water or a group Z-(W)$_n$ where n is 2, the polycarbonate will be linear, terminated with a hydroxyl group at each end. If the CTA is a group Z-(W)$_n$ where n is 3 or more, the architecture of the polycarbonate may comprise a core moiety corresponding to the group Z of the CTA, with n polycarbonate chains, each terminated with a hydroxyl group extended therefrom (such as a "star-like" architecture). This means that these polycarbonates can be used as macro initiators for a second polymerisation to produce copolymers of formula B-(A)$_n$. Hydroxyl groups can be used to initiate various different types of polymerisations to form A. For example, ring opening polymerisation (ROP) of monomers such as lactides, lactones and other cyclic carbonates can be carried out in the presence of a metal alkoxide (for example, zinc, magnesium, yttrium, lanthanide, titanium, zirconium, aluminium, tin(IV), tin(II), iron(II), iron(III), cobalt(II), lithium, potassium, sodium, calcium, gallium, indium and scandium alkoxides) or a nucleophile (for example, carbenes, optionally substituted amines, phosphines, lipase enzymes, or combinations of alcohol(s) and thiourea, alcohol(s) and urea, and bronstead acid(s) and alcohol(s)) and hydroxyl terminated polycarbonates produced by the process of the first aspect to form copolymers of formula B-(A)$_n$. Ring opening of epoxides can also be initiated by the hydroxyl groups of hydroxyl terminated polycarbonates produced by the process of the first aspect to produce polymeric blocks of polyethers. If the ring opening of an epoxide by a hydroxyl group is carried out in the presence of an anhydride (for example, maleic anhydride) or a di- or polycarboxylic acid, the polymeric block produced is a polyester.

Polyesters can also be synthesised by adding polyols (i.e. monomers having two or more hydroxyl groups, such as diols, triols, tetraols and the like) to monomers having two or more ester, carboxylic acid, or acid chloride groups (for example, diesters, diacids and diacid chlorides). It will be appreciated that the polycarbonates produced from chain transfer agents having 2 or more W groups (i.e. when n is 2 or more) can be used as monomers in the production of polymers such as polyesters or polyurethanes.

In certain embodiments, B is a polycarbonate as produced by the process of the first aspect of the invention, and A is a polyester which is produced by adding either a) a polycarbonate as produced by the process of the first aspect of the invention wherein n is at least 2 (wherein A may be the same as, or different to, B) or b) a monomer comprising two or more OH groups, to a monomer comprising two or more ester, carboxylic acid or acid chloride groups. In other embodiments, B is a polycarbonate as produced by the process of the first aspect of the invention, and A is a polyurethane which is produced by adding either a) a polycarbonate as produced by the process of the first aspect of the invention wherein n is at least 2 (wherein A may be the same as, or different to, B) or b) a monomer comprising two or more OH groups, to a monomer comprising two or more isocyanate groups.

It will also be appreciated that the hydroxyl groups on the polycarbonates as produced by the process of the first aspect of the invention can be reacted (or "functionalised") to form different functional groups, such as esters, carboxylic acids, or amines prior to the polymeric block A being added. Reagents which are used to functionalise the hydroxyl groups are well known in the art.

In certain embodiments, the hydroxyl groups on B are reacted with reagents suitable to convert the hydroxyl groups to ester, carboxylic acid or amine groups. A is then formed by reacting the "functionalised" B with one or more monomers. It will be appreciated that when the hydroxyl group(s) on B are converted to carboxylic acid groups, A can be a polyester which is formed by adding a monomer having two or more hydroxyl groups (this may be a polycarbonate as produced by the process of the first aspect of the invention wherein n is at least 2) to a monomer having two or more carboxylic acid groups (this may be a polycarbonate as produced by the process of the first aspect of the invention wherein n is at least 2 and where the hydroxyl groups have been reacted to form carboxylate groups, and may be the same as, or different to, B).

The skilled person will also appreciate that A can be a polyamide if the hydroxyl groups on B are converted to carboxylic acid groups, and A is formed by adding a monomer having two or more amine groups (this may be a polycarbonate as produced by the process of the first aspect of the invention wherein n is at least 2 and where the hydroxyl groups have been reacted to form amine groups) to a monomer having two or more carboxylic acid groups (this may be a polycarbonate as produced by the process of the first aspect of the invention wherein n is at least 2 and where the hydroxyl groups have been reacted to form carboxylate groups, and may be the same as, or different to, B).

When the hydroxyl group(s) on B are converted to amine groups, A can be an epoxy resin which is formed by adding a monomer having at least two epoxide groups to a monomer having at least two amine groups (this may be a polycarbonate as produced by the process of the first aspect of the invention wherein n is at least 2 and where the hydroxyl groups have been reacted to form amine groups, and may be the same as B).

In certain embodiments, A is produced from a monomer selected from the group consisting of a lactide, a lactone, a cyclic carbonate such as propylene carbonate or trimethylene carbonate, an epoxide or combinations thereof, or is produced from a combination of a di-isocyanate and a compound comprising two or more hydroxyl groups; a compound comprising two or more amine groups, a compound comprising two or more acid chloride groups, a compound comprising two or more ester groups or a compound comprising two or more hydroxyl groups and a compound comprising two or more hydroxyl groups; an epoxide and an anhydride, a compound comprising two or more carboxylic acid groups, or a compound comprising two or more amine groups, or an epoxide which is preferably different to the epoxide used to produce B and carbon dioxide. Preferably the compound having two or more hydroxyl groups is a diol, triol, tetraol or polyol or a polycarbonate produced by the process of the first aspect, where n is at least 2. Preferably, the compound having two or more amine groups is a diamine, a triamine, a tetraamine or a polycarbonate produced by the process of the first aspect, where n is at least 2 and the hydroxyl groups have been functionalised to amine groups. Preferably, the compound comprising two or more carboxylic acid groups is a di or poly carboxylic acid, or a polycarbonate as produced by the process of the first aspect where n is at least 2 and the hydroxyl groups have been functionalised to carboxylic acid groups. Preferably, the compound having two or more ester groups is a diester, a triester, a tetraester or a polycarbonate produced by the process of the first aspect, where n is at least 2 and the hydroxyl groups have been functionalised to ester groups. Preferably, the compound having two or more acid chloride groups is a diacid chloride, a triacid chloride, a tetraacid chloride or a polycarbonate produced by the process of the first aspect, where n is at least 2 and the hydroxyl groups have been functionalised to acid chloride groups.

A may be, for example, a polyester, polyether, polycarbonate, polyamide, polyurethane or any copolymer combination thereof. In certain embodiments, $B-(A)_n$ is a tri-block copolymer of formula A-B-A, wherein A may be, for example, a poly(lactide) formed by the ring-opening of lactic acid from the terminal hydroxyl groups of the polycarbonate block "B".

Alternatively, the hydroxyl terminated polycarbonate produced by the process of the first aspect can be coupled with a preformed "A" polymeric unit to yield a copolymer of formula $B-(A)_n$. For example, the preformed "A" is terminated at one end with a group capable of reacting with a hydroxyl group, such as an acid chloride, an acid, an ester, an amide, an anhydride, a carboxylic acid, an isocyanurate or urea, and then reacted with the polycarbonate formed by the process of the first aspect to produce a copolymer of formula $B-(A)_n$. The identity of A may be as described above. For example, A may be a polycarbonate produced by the process of the first aspect where the hydroxyl group(s) has been functionalised to form an ester, a carboxylic acid or an amine group.

It will be appreciated that if a mixture of polycarbonate chains with different end groups (for example, a mixture of chains terminated by one hydroxyl end group and one acetate end group and chains terminated at both ends with hydroxyl groups), then a mixture of block copolymers with differing architectures would be produced. In the instance described above, this is avoided.

The process of the first aspect produces polycarbonates which are terminated at all ends with hydroxyl groups. It will be appreciated by the skilled person that the production of the copolymer of formula $B-(A)_n$ can be carried out immediately after the polycarbonate has been synthesised (i.e. without further purification steps to ensure both ends are terminated in hydroxyl groups).

All preferred features of the first aspect of the invention apply to the fourth aspect of the invention mutatis mutandis.

The fifth aspect of the invention provides a method of producing the block copolymer of the fourth aspect. The method comprises the steps of synthesising a polycarbonate according to the process of the first aspect and either reacting the polycarbonate with at least one further monomer, or reacting the polycarbonate with at least one further polymeric unit which differs in structure from the polycarbonate. In preferred embodiments, the step of reacting the polycarbonate with at least one further monomer, or the step of reacting the polycarbonate with at least one polymeric unit which differs in structure from the polycarbonate occurs directly after the step of synthesising a polycarbonate according to the process of the first aspect. The method of the fifth aspect may additionally comprise the step of reacting the hydroxyl group(s) on B with reagents suitable to convert the hydroxyl group(s) to ester, carboxylic acid or amine group(s) prior to the step of reacting the polycarbonate with at least one further monomer, or reacting the polycarbonate with at least one further polymeric unit which differs in structure from the polycarbonate. All preferred features of the first aspect and the fourth aspect of the invention apply to the fifth aspect mutatis mutandis. In particular, the identity of the further monomer or polymeric unit may correspond to the identity described for A in the fourth aspect.

A class of catalysts which fall within the scope of the catalysts which are useful for copolymerisation of at least one epoxide and $CO_2$ are known from International patent application no. WO2009/130470, the entire contents of which are incorporated herein by reference. A further class of catalysts has been developed.

Therefore, in a sixth aspect of the invention, a catalyst of formula (III) is provided:

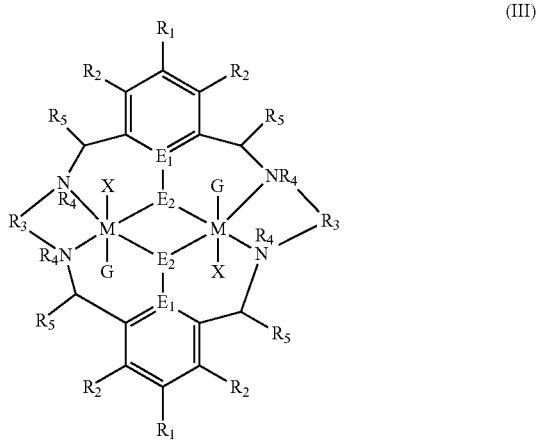

(III)

wherein $R_1$ and $R_2$ are independently hydrogen, halide, a nitro group, a nitrile group, an imine, an amine, an ether group, a silyl ether group or an acetylide group or optionally substituted alkyl, alkenyl, alkynyl, haloalkyl, aryl, heteroaryl, alicyclic or heteroalicyclic;

$R_3$ is optionally substituted alkylene, alkenylene, alkynylene, heteroalkylene, heteroalkenylene, heteroalkynylene, arylene, heteroarylene or cycloalkylene; wherein alkylene, alkenylene, alkynylene, heteroalkylene, heteroalkenylene and heteroalkynylene may optionally be interrupted by aryl, heteroaryl, alicyclic or heteroalicyclic;

$R_4$ is H, or optionally substituted aliphatic, heteroaliphatic, alicyclic, heteroalicyclic, aryl, heteroaryl, alkylheteroaryl or alkylaryl;

$R_5$ is H, or optionally substituted aliphatic, heteroaliphatic, alicyclic, heteroalicyclic, aryl, heteroaryl, alkylheteroaryl or alkylaryl;

$E_1$ is C, $E_2$ is O, S or NH or $E_1$ is N and $E_2$ is O;

each G is independently absent or a neutral or anionic donor ligand which is a Lewis base;

M is Zn(II), Co(II), Mn(II), Mg(II), Fe(II), Cr(II), Ti(II), Cr(III)-X, Co(III)-X, Mn(III)-X, Fe(III)-X, Ca(II), Ge(II), Al(III)-X, Ti(III)-X, V(III)-X, Ge(IV)-(X)$_2$ or Ti(IV)-(X)$_2$ (preferably Mg(II), Ca(II) or Ge(II));

wherein when both instances of G are absent and all instances of $R_5$ are hydrogen, X is OC(O)$R^Z$, OSO($R^Z$)$_2$, OSO$_2R^Y$, OSO$R^T$, O$R^V$, phosphinate, hydroxyl, carbonate, nitrate or optionally substituted aryl, heteroaryl, alicyclic or heteroalicyclic;

$R^Z$ is independently hydrogen or optionally substituted $C_{2-20}$aliphatic, $C_{2-20}$ haloaliphatic, heteroaliphatic, alicyclic, heteroalicyclic, aryl, alkylaryl or heteroaryl;

$R^Y$ is hydrogen or optionally substituted aliphatic, heteroaliphatic, alicyclic, heteroalicyclic, aryl, heteroaryl or alkylaryl with the proviso that $R^Y$ is not $C_7H_7$; and $R^V$ is optionally substituted aryl, haloaryl, heteroaryl, heteroaliphatic, alicyclic, alkylaryl or heteroaliyclic;

$R^T$ is hydrogen, or optionally substituted aliphatic, haloaliphatic, heteroaliphatic, alicyclic, heteroalicyclic, aryl, alkylaryl or heteroaryl;

and wherein when either one or both instances of G are not absent, or when one or more instances of $R^5$ are not hydrogen, X is OC(O)$R^x$, OSO$_2R^x$, OSO($R^x$)$_2$, OSO$R^x$, O$R^x$, phosphinate, halide, nitrate, hydroxyl, carbonate, amido or optionally substituted aliphatic, heteroaliphatic, alicyclic, heteroalicyclic, aryl or heteroaryl; and $R_x$ is independently hydrogen, or optionally substituted aliphatic, haloaliphatic, heteroaliphatic, alicyclic, heteroalicyclic, aryl, alkylaryl or heteroaryl.

In preferred embodiments, the catalyst of formula (III) has the following formula:

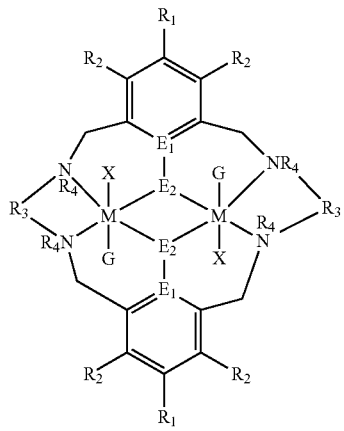

wherein $R_1$ and $R_2$ are independently hydrogen, halide, a nitro group, a nitrile group, an imine, an amine, an ether group, a silyl ether group or an acetylide group or optionally substituted alkyl, alkenyl, alkynyl, haloalkyl, aryl, heteroaryl, alicyclic or heteroalicyclic;

$R_3$ is optionally substituted alkylene, alkenylene, alkynylene, heteroalkylene, heteroalkenylene or heteroalkynylene, which may optionally be interrupted by aryl, heteroaryl, alicyclic or heteroalicyclic; arylene; heteroarylene or cycloalkylene;

$R_4$ is H, or optionally substituted aliphatic, heteroaliphatic, alicyclic, heteroalicyclic, aryl, heteroaryl, alkylheteroaryl or alkylaryl;

$E_1$ is C, $E_2$ is O, S or NH or $E_1$ is N and $E_2$ is O;

each G is independently absent or a neutral or anionic donor ligand which is a Lewis base;

M is Zn(II), Co(II), Mn(II), Mg (II), Fe(II), Cr(II), Cr(III)-X, Co(III)-X, Mn(III)-X, Fe(III)-X, Ca(II), Ge(II), Al(III)-X, Ti(III)-X or V(III)-X;

wherein when both instances of G are absent, X is OC(O)$R^Z$, OSO($R^Z$)$_2$, OSO$_2R^Y$, O$R^V$, hydroxyl, carbonate, nitrate or optionally substituted aryl, heteroaryl, alicyclic or heteroalicyclic;

$R^Z$ is independently hydrogen or optionally substituted $C_{2-20}$aliphatic, $C_{2-20}$ haloaliphatic, heteroaliphatic, alicyclic, heteroalicyclic, aryl, alkylaryl or heteroaryl;

$R^Y$ is hydrogen or optionally substituted aliphatic, heteroaliphatic, alicyclic, heteroalicyclic, aryl, heteroaryl or alkylaryl with the proviso that $R^Y$ is not $C_7H_7$; and $R^V$ is optionally substituted aryl, haloaryl, heteroaryl, heteroaliphatic, alicyclic, alkylaryl or heteroaliyclic;

and wherein when either one or both instances of G are not absent, X is OC(O)$R^x$, OSO$_2R^x$, OSO($R^x$)$_2$, O$R^x$, halide, nitrate, hydroxyl, carbonate, amido or optionally substituted aliphatic, heteroaliphatic, alicyclic, heteroalicyclic, aryl or heteroaryl; and $R_x$ is independently hydrogen, or optionally substituted aliphatic, haloaliphatic, heteroaliphatic, alicyclic, heteroalicyclic, aryl, alkylaryl or heteroaryl.

In preferred embodiments of the sixth aspect, $R_1$ and $R_2$ may be the same or different. In some embodiments, $R_1$ and $R_2$ are independently hydrogen, halide, a nitro group, a nitrile group, an imine, an amine, an ether group, a silyl ether group or an acetylide group or optionally substituted alkyl, alkenyl, alkynyl, haloalkyl, aryl, heteroaryl, alicyclic or heteroalicyclic. In other embodiments, $R_1$ and $R_2$ are independently selected from hydrogen, halide, a nitro group, a nitrile group, an imine, an ether group, a silyl ether group or an acetylide group or optionally substituted alkyl, alkenyl, alkynyl, haloalkyl, aryl or alicyclic. $R_1$ and $R_2$ are preferably independently selected from hydrogen, tBu, Me, $CF_3$, phenyl, F, Cl, Br, I, $NMe_2$, $NEt_2$, $NO_2$, OMe, $OSiEt_3$, CNMe, CN or CCPh, more preferably hydrogen, OMe, Me, $NO_2$, halogen or tBu (e.g. hydrogen or tBu). In certain embodiments, $R_2$ is hydrogen and $R_1$ is any one of the groups defined above, preferably $NO_2$, halogen, tBu, OMe or Me, more preferably tBu, OMe or Me.

In the sixth aspect, $R_3$ is a disubstituted alkyl, alkenyl, alkynyl, heteroalkyl, heteroalkenyl or heteroalkynyl group which may optionally be interrupted by an aryl, heteroaryl, alicyclic or heterolicyclic group, or may be a disubstituted aryl or cycloalkyl group which acts as a bridging group between two nitrogen centres in the catalyst of formula (III). Thus, where $R_3$ is a alkylene group, such as dimethylpropylene, the $R_3$ group has the structure $—CH_2—C(CH_3)_2—CH_2—$. The definitions of the alkyl, aryl, cycloalkyl etc groups set out above therefore also relate respectively to the alkylene, arylene, cycloalkylene etc groups set out for $R_3$. In certain embodiments, $R_3$ is optionally substituted alkylene, alkenylene, alkynylene, heteroalkylene, heteroalkenylene, heteroalkynylene, arylene, heteroarylene or cycloalkylene; wherein alkylene, alkenylene, alkynylene, heteroalkylene, heteroalkenylene and heteroalkynylene may optionally be interrupted by aryl, heteroaryl, alicyclic or heteroalicyclic. In other embodiments, $R_3$ is optionally substituted alkylene, alkenylene, alkynylene arylene, or cycloalkylene, wherein alkylene, alkenylene, alkynylene may optionally be interrupted by aryl or alicyclic. In preferred embodiments, $R_3$ is a propylene group which is optionally substituted by aliphatic (preferably $C_{1-6}$alkyl) or aryl groups. Preferably $R_3$ is ethylene, 2,2-dimethylpropylene, propylene, butylene, phenylene, cyclohexylene or biphenylene, more preferably 2,2-dimethylpropylene. When $R_3$ is cyclohexylene, it can be the racemic, RR- or SS-forms.

$R_4$ is H, or optionally substituted aliphatic, heteroaliphatic, alicyclic, heteroalicyclic, aryl, heteroaryl, alkylheteroaryl or alkylaryl. Preferably $R_4$ is independently selected from hydrogen, or optionally substituted alkyl, alkenyl, alkynyl, aryl or heteroaryl. In certain embodiments, $R_4$ is independently selected from hydrogen, or optionally substituted aliphatic, alicyclic, aryl or alkylaryl. More preferably, $R_4$ is hydrogen. Exemplary options for $R_4$ include H, Me, Et, Bn, iPr, tBu or Ph. $R_4$ is preferably hydrogen.

$R_5$ is H, or optionally substituted aliphatic, heteroaliphatic, alicyclic, heteroalicyclic, aryl, heteroaryl, alkylheteroaryl or alkylaryl. Preferably $R_5$ is independently selected from hydrogen, or optionally substituted aliphatic or aryl. More preferably, $R_5$ is selected from hydrogen, alkyl or aryl. Exemplary $R_5$ groups include hydrogen, methyl, trifluoromethyl, ethyl and phenyl (preferably hydrogen, trifluoromethyl and methyl). In particularly preferred embodiments, all instances of $R_5$ are hydrogen. In other particularly preferred embodiments, one or more instances of $R_5$ are not hydrogen.

In certain embodiments, $R_1$, $R_2$, $R_3$, $R_4$ and $R_5$ are each independently optionally substituted by halogen, hydroxyl, nitro, carbonate, alkoxy, aryloxy, heteroaryloxy, amino, alkylamino, imine, nitrile, acetylide, or unsubstituted aliphatic, heteroaliphatic, alicyclic, heteroalicyclic, aryl or heteroaryl. Preferably $R_1$, $R_2$, $R_3$, $R_4$ and $R_5$ are each independently optionally substituted by halogen, hydroxyl, nitro, carbonate, alkoxy, aryloxy, imine, nitrile, acetylide, unsubstituted aliphatic, unsubstituted alicyclic and unsubstituted aryl.

In certain embodiments, $E_1$ is C, $E_2$ is O, S or NH, and preferably $E_2$ is O. In other embodiments, $E_1$ is N and $E_2$ is O.

When both instances of G are absent, (preferably when both instances of G are absent and all instances of $R_5$ are hydrogen), each X is independently selected from $OC(O)R^Z$, $OSO(R^Z)_2$, $OSO_2R^Y$, $OSO_2R^T$, $OR^V$, phosphinate, hydroxyl, carbonate, nitrate or optionally substituted aryl, heteroaryl, alicyclic or heteroalicyclic. In certain embodiments, each X is independently selected from $OC(O)R^Z$, $OSO(R^Z)_2$, $OSO_2R^Y$, $OR^V$, hydroxyl, carbonate, nitrate or optionally substituted aryl, heteroaryl, alicyclic or heteroalicyclic. In other embodiments, each X is independently selected from $OC(O)R^Z$, $OSO(R^Z)_2$, $OSO_2R^Y$, $OSO_2R^T$, $OR^V$, phosphinate, hydroxyl, carbonate, nitrate or optionally substituted aryl or alicyclic. $R^Z$ is independently hydrogen or optionally substituted $C_{2-20}$aliphatic, $C_{2-20}$haloaliphatic, heteroaliphatic, alicyclic, heteroalicyclic, aryl, alkylaryl or heteroaryl. $R^Y$ is hydrogen or optionally substituted aliphatic, heteroaliphatic, alicyclic, heteroalicyclic, aryl, heteroaryl or alkylaryl, with the proviso that $R^Y$ is not $C_7H_7$. $R^V$ is optionally substituted aryl, haloaryl, heteroaryl, heteroaliphatic, alicyclic, alkylaryl or heteroalicyclic. Preferably, X is $OC(O)R^Z$ or $OR^V$. $R^T$ is hydrogen, or optionally substituted aliphatic, haloaliphatic, heteroaliphatic, alicyclic, heteroalicyclic, aryl, alkylaryl or heteroaryl. Exemplary X groups for when both instances of G are absent include benzoate, pentafluorobenzoate, pivalate, adamantyl carboxylate, diphenyl phosphinate, dioctyl phosphinate, bis(4-methoxyphenyl)phosphinate, hexanoate, octanoate, dodecanoate, stearate.

Preferably, $R^Z$ is optionally substituted aryl, heteroaryl, alicyclic, heteroalicyclic, alkylaryl, $C_{2-20}$aliphatic (preferably $C_{4-20}$aliphatic, more preferably $C_{8-20}$aliphatic), $C_{2-20}$haloaliphatic (preferably $C_{2-20}$haloaliphatic, more preferably $C_{2-20}$haloaliphatic) or $C_{4-20}$heteroaliphatic (preferably hetero$C_{8-20}$aliphatic). In certain embodiments, $R^Z$ is selected from optionally substituted $C_{2-20}$aliphatic, $C_{2-20}$haloaliphatic, alicyclic, aryl and alkylaryl. More preferably, $R^Z$ is an optionally substituted $C_{4-20}$aliphatic, $C_{4-20}$haloaliphatic, alicyclic or aryl group, even more preferably, an unsubstituted $C_{4-12}$aliphatic group, an unsubstituted alicyclic group or an aryl group which is optionally substituted by one or more halogen groups (preferably fluorine). Exemplary $R^Z$ groups include phenyl, pentafluorophenyl, n-pentane, n-heptane, n-undecane, n-heptadecane, tert-butyl and adamantane.

Preferably, $R^Y$ is optionally substituted aryl, heteroaryl, alicyclic, heteroalicyclic, alkylaryl, aliphatic (preferably $C_{4-20}$aliphatic, more preferably $C_{8-20}$aliphatic) or hetero$C_{4-20}$aliphatic (preferably hetero$C_{8-20}$aliphatic), with the proviso that $R^Y$ is not $C_7H_7$. In certain embodiments, $R^Y$ is hydrogen, optionally substituted aliphatic, alicyclic, aryl, or alkylaryl, with the proviso that $R^Y$ is not $C_7H_7$. More preferably, $R^Y$ is optionally substituted heteroaryl, alicyclic or heteroalicyclic. In certain embodiments, $R^V$ is optionally substituted aryl, haloaryl, alicyclic or alkylaryl.

Preferably, $R^V$ is optionally substituted aryl, heteroaryl, alicyclic, heteroalicyclic or hetero$C_{4-20}$aliphatic (preferably betero$C_{8-20}$aliphatic), more preferably optionally substituted aryl, heteroaryl, alicyclic or heteroalicyclic. In preferred embodiments, $R^V$ is optionally substituted aryl or alicyclic.

Preferably, $R^T$ is hydrogen, or optionally substituted aliphatic, haloaliphatic, alicyclic, aryl or alkylaryl. In preferred embodiments, $R^T$ is hydrogen, or optionally substituted aliphatic, aryl or alicyclic.

$R^Z$, $R^Y$, $R^V$ and $R^T$ are optionally substituted by halogen, hydroxyl, nitrile, nitro, amido, amino, imine or unsubstituted $C_{1-6}$alkyl, $C_{2-6}$alkenyl, $C_{2-6}$alkynyl, $C_{6-10}$aryl, heteroaryl, $C_{3-6}$ cycloalkyl, $C_{3-6}$cycloalkenyl, $C_{3-6}$cycloalkynyl, alkoxy or alkylthio. In certain embodiments, $R^Z$, $R^Y$, $R^T$ and $R^V$ are each independently optionally substituted by halogen, hydroxyl, nitro, carbonate, alkoxy, aryloxy, heteroaryloxy, amino, alkylamino, imine, nitrile, acetylide, or unsubstituted aliphatic, heteroaliphatic, alicyclic, heteroalicyclic, aryl or heteroaryl. In preferred embodiments, $R^Z$, $R^Y$, $R^V$ and $R^T$ are each independently optionally substituted by halogen, hydroxyl, nitro, carbonate, alkoxy, aryloxy, imine, nitrile, acetylide, unsubstituted aliphatic, unsubstituted alicyclic and unsubstituted aryl. Preferably, $R^Z$, $R^Y$, $R^V$ and $R^T$ are substituted by halogen, more preferably, fluorine.

As described in the first aspect, when X is a halogenated group, the amount of chain transfer agent required to ensure that both ends of the polycarbonate chains are terminated in hydroxyl groups is greatly reduced. Therefore, in a preferred embodiment of the sixth aspect, when both instances of G are absent (preferably when both instances of G are absent and all instances of $R_5$ are hydrogen), X is $OC(O)R^Z$, $OSO(R^Z)_2$, $OSO_2R^Y$, $OSOR^T$, $OR^V$, halophosphinate, haloaryl, haloheteroaryl, haloalicyclic, haloheteroalicyclic, haloheteroaliphatic or haloaliphatic wherein $R^Z$, $R^Y$, $R^V$ and $R^T$ are independently $C_{2-20}$ haloaliphatic, $C_{2-20}$haloheteroaliphatic, haloaryl, haloheteroaryl, haloheteroalicyclic or haloalicyclic, preferably $C_{2-20}$haloaliphatic, or haloalicyclic, more preferably $C_{2-20}$fluoroaliphatic. When X is $OSO(R^Z)_2$, either one or both $R^Z$ is $C_{2-20}$haloaliphatic, haloaryl or haloalicyclic more preferably $C_{2-20}$fluoroaliphatic. In certain other embodiments, when either one or both instances of G are not absent, X is preferably $OC(O)R^x$, $OSO_2R^x$, $OSOR^x$, $OSO(R^x)_2$, $OR^x$, halophosphinate, haloheteroaliphatic, haloaryl, haloheteroaryl, haloalicyclic, haloheteroalicyclic or haloaliphatic (more preferably, $OC(O)R^x$, $OSO_2R^x$, $OSOR^x$, $OSO(R^x)_2$, $OR^x$, halophosphinate or haloaliphatic), wherein at least one $R^x$ is haloaliphatic, haloheteroaliphatic, haloaryl haloheteroaryl, haloheteroalicyclic or haloalicyclic, more preferably haloaliphatic, haloaryl or haloalicyclic (such as fluoroaliphatic). For example, $R^x$ may be pentafluorophenyl or trifluoromethyl.

In certain other embodiments, when one or more instances of $R_5$ are not hydrogen, X is preferably $OC(O)R^x$, $OSO_2R^x$, $OSOR^x$, $OSO(R^x)_2$, $OR^x$, halophosphinate, haloheteroaliphatic, haloaryl, haloheteroaryl, haloalicyclic, haloheteroalicyclic or haloaliphatic (more preferably, $OC(O)R^x$, $OSO_2R^x$, $OSOR^x$, $OSO(R^x)_2$, $OR^x$, halophosphinate or haloaliphatic), wherein at least one $R^x$ is haloaliphatic, haloheteroaliphatic, haloaryl, haloheteroaryl, haloheteroalicyclic or haloalicyclic, more preferably haloaliphatic, haloaryl or haloalicyclic (such as fluoroaliphatic). For example, $R^x$ may be pentafluorophenyl or trifluoromethyl.

When G is not absent, it is a group which is capable of donating a lone pair of electrons (i.e. a Lewis base). In certain embodiments, G is a nitrogen containing Lewis base. Each G may independently be neutral or negatively charged. If G is negatively charged, then one or more positive counterions will be required to balance out the change of the complex. Suitable positive counterions include group 1 metal ions ($Na^+$, $K^+$, etc), group 2 metal ions ($Mg^{2+}$, $Ca^{2+}$, etc), imidazolium ions, positively charged optionally substituted heteroaryl, heteroalicyclic or heteroaliphatic groups, ammonium ions (i.e. $N(R^{12})_4^+$), iminium ions (i.e. $(R^{12})_2C=N(R^{12})_2^+$, such as bis(triphenylphosphine)iminium ions) or phosphonium ions ($P(R^{12})_4^+$), wherein each $R^{12}$ is independently selected from hydrogen or optionally substituted aliphatic, heteroaliphatic, alicyclic, heteroalicyclic, aryl or heteroaryl. Exemplary counterions include $[H-B]^+$ wherein B is selected from triethylamine, 1,8-diazabicyclo[5.4.0]undec-7-ene and 7-methyl-1,5,7-triazabicyclo[4.4.0]dec-5-ene.

G is preferably independently selected from an optionally substituted heteroaliphatic group, an optionally substituted heteroalicyclic group, an optionally substituted heteroaryl group, a halide, hydroxide, hydride, a carboxylate, an ether, a thioether, carbene, a phosphine, a phosphine oxide, an amine, an acetamide, acetonitrile, an ester, a sulfoxide, a sulfonate and water. More preferably, G is independently selected from water, an alcohol, a substituted or unsubstituted heteroaryl (imidazole, methyl imidazole, pyridine, 4-dimethylaminopyridine, pyrrole, pyrazole, etc), an ether (dimethyl ether, diethylether, cyclic ethers, etc), a thioether, carbene, a phosphine, a phosphine oxide, a substituted or unsubstituted heteroalicyclic (morpholine, piperidine, tetrahydrofuran, tetrahydrothiophene, etc), an amine, an alkyl amine (trimethylamine, triethylamine, etc), acetonitrile, an ester (ethyl acetate, etc), an acetamide (dimethylacetamide, etc), a sulfoxide (dimethylsulfoxide, etc), a carboxylate, a hydroxide, hydride, a halide, a nitrate, a sulfonate, etc. In some embodiments, one or both instances of G is independently selected from optionally substituted heteroaryl, optionally substituted heteroaliphatic, optionally substituted heteroalicyclic, halide, hydroxide, hydride, an ether, a thioether, carbene, a phosphine, a phosphine oxide, an amine, an alkyl amine, acetonitrile, an ester, an acetamide, a sulfoxide, a carboxylate, a nitrate or a sulfonate. In certain embodiments, G may be a halide; hydroxide; hydride; water; a heteroaryl, heteroalicyclic or carboxylate group which are optionally substituted by alkyl, alkenyl, alkynyl, alkoxy, halogen, hydroxyl, nitro or nitrile. In preferred embodiments, G is independently selected from halide; water; a heteroaryl optionally substituted by alkyl (e.g. methyl, ethyl etc), alkenyl, alkynyl, alkoxy (preferably methoxy), halogen, hydroxyl, nitro or nitrile. In some embodiments, one or both instances of G is negatively charged (for example, halide). In further embodiments, one or both instances of G is an optionally substituted heteroaryl. Exemplary G groups include chloride, bromide, pyridine, methylimidazole (for example N-methyl imidazole) and dimethylaminopyridine (for example, 4-methylaminopyridine). When either one or both instances of G are not absent, each X is independently selected from $OC(O)R^x$, $OSO_2R^x$, $OSOR^x$, $OSO(R^x)_2$, $OR^x$, phosphinate, halide, nitrate, hydroxyl, carbonate, amido or optionally substituted aliphatic, heteroaliphatic, alicyclic, heteroalicyclic, aryl or heteroaryl. Each $R_x$ is independently hydrogen, or optionally substituted aliphatic, haloaliphatic, heteroaliphatic, alicyclic, heteroalicyclic, aryl, alkylaryl or heteroaryl. Preferably, X is $OC(O)R^x$ or $OR^x$. Preferably, $R_x$ is hydrogen, optionally substituted aliphatic, alicyclic, haloaliphatic, alkylaryl, aryl or heteroaryl, more preferably $R_x$ is hydrogen, optionally substituted aliphatic, alicyclic, haloaliphatic, alkylaryl or aryl. $R_1$ and $R_2$ are independently hydrogen, halide, a nitro group, a nitrile group, an imine, an amine, an ether group, a silyl ether group, or an acetylide group or an optionally substituted alkyl, alkenyl, alkynyl, haloalkyl, aryl, heteroaryl, alicyclic or heteroalicyclic. $R_3$ is optionally substituted alkylene, alkenylene, alkynylene, heteroalkylene, heteroalkenylene, heteroalkynylene, arylene, heteroarylene or cycloalkylene, wherein alkylene, alkenylene, alkynylene, heteroalkylene, heteroalkenylene and heteroalkynylene may optionally be interrupted by aryl, heteroaryl, alicyclic or heteroalicyclic. $R_4$ is H, or optionally substituted aliphatic, heteroaliphatic, alicyclic, heteroalicyclic, aryl, heteroaryl, alkylheteroaryl or alkylaryl. Preferably, $R_1$, $R_2$, $R_3$, $R_4$, $R_5$ and $R^x$ are each independently optionally substituted by halogen, hydroxyl, nitro, carbonate, alkoxy, aryloxy, heteroaryloxy, amino, alkylamino, imine, nitrile, acetylide, or unsubstituted aliphatic, heteroaliphatic, alicyclic, heteroalicyclic, aryl or heteroaryl. Exemplary X groups for when at least one G is not absent include benzoate, pentafluorobenzoate, pivalate, adamantyl carbonate, diphenyl phosphinate, bis(4-methoxyphenyl) phosphinate, hexanoate, octanoate, dodecanoate, stearate, chloride, bromide, acetate and trifluroracetate (preferably chloride, bromide, acetate or trifluoroacetate). When one or more instances of $R_5$ are not hydrogen, each X is independently selected from $OC(O)R^x$, $OSO_2R^x$, $OSOR^x$, $OSO(R^x)_2$, $OR^x$, phosphinate, halide, nitrate, hydroxyl, carbonate, amido or optionally substituted aliphatic, heteroaliphatic, alicyclic, heteroalicyclic, aryl or heteroaryl. Each $R_x$ is independently hydrogen, or optionally substituted aliphatic, haloaliphatic, alicyclic, aryl or alkylaryl. Preferably, X is $OC(O)R^x$ or $OR^x$. $R_1$ and $R_2$ are independently hydrogen, halide, a nitro group, a nitrile group, an imine, an ether group, a silyl ether group or an acetylide group or optionally substituted alkyl, alkenyl, alkynyl, haloalkyl, aryl or alicyclic group. $R_3$ is independently selected from optionally substituted alkylene, alkenylene, alkynylene, arylene or cycloalkylene, wherein alkylene, alkenylene or alkynylene may optionally be interrupted by aryl or alicyclic. $R_4$ is independently selected from H, or optionally substituted aliphatic, alicyclic, aryl, or alkylaryl. $R_5$ is preferably optionally substituted aliphatic, alicyclic, aryl, or alkylaryl. $R_1$, $R_2$, $R_3$, $R_4$ and $R_5$ are each independently optionally substituted by halogen, hydroxyl, nitro, carbonate, alkoxy, aryloxy, imine, nitrile, acetylide, unsubstituted aliphatic, unsubstituted alicyclic and unsubstituted aryl. Exemplary X groups for when one or more instances of $R_5$ are not hydrogen include benzoate, pentafluorobenzoate, pivalate, adamantyl carbonate, diphenyl phosphinate, bis(4-methoxyphenyl)phosphinate, hexanoate, octanoate, dodecanoate, stearate, chloride, bromide, acetate and trifluroracetate (preferably chloride, bromide, acetate or trifluoroacetate).

It will be appreciated that when a G group is present, the G group may be associated with a single M metal centre as shown in formula (III), or the G group may be associated with both metal centres and form a bridge between the two metal centres, as shown below in formula (IIIb):

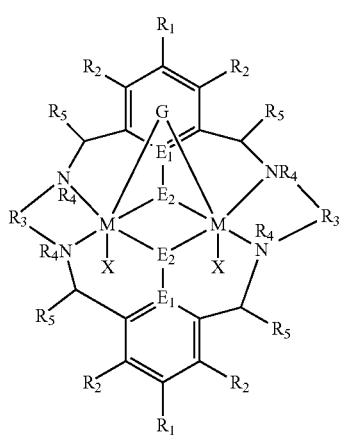
(IIIb)

Wherein $R_1$, $R_2$, $R_3$, $R_4$, $R_5$, M, G, X, $E_1$ and $E_2$ are as defined for formula (III).

Preferably M is Zn(II), Cr(III), Cr(II), Co(III), Co(II), Mn(III), Mn(II), Mg(II), Fe(II), Fe(III), Ca(II), Ge(II), Ti(II), Al(III), Ti(III), V(III), Ge(IV) or Ti(IV), more preferably Zn(II), Cr(III), Co(II), Mn(II), Mg(II), Fe(II) or Fe(III), and most preferably Zn(II) or Mg(II). It will be appreciated that when M is Cr(III), Co(III), Mn(III) or Fe(III), the catalyst of formula (III) will contain an additional X group co-ordinated to the metal centre, wherein X is as defined above. It will also be appreciated that when M is Ge(IV) or Ti(IV), the catalyst of formula (III) will contain two additional X group co-ordinated to the metal centre, wherein X is as defined above. In certain embodiments, when M is Ge(IV) or Ti(IV), both G may be absent.

The skilled person will also appreciate that each M may be the same (for example, both M may be Mg, Zn, Fe or Co) or each M may be different and can be present in any combination (for example, Fe and Zn, Co and Zn, Mg and Fe, Co and Fe, Mg and Co, Cr and Mg, Cr and Zn, Mn and Mg, Mn and Zn, Mn and Fe, Cr and Fe, Cr and Co, Al and Mg, Al and Zn etc). When M is the same metal, it will be appreciated that each M may be in the same oxidation state (for example both M may be Co(II), Fe(II) or Fe(III)), or in a different oxidation state (for example, one M may be Co(II) and the other M may be Co(III), one M may be Fe(II) and the other M may be Fe(III), or one M may be Cr(II) and the other M may be Cr(III)).

In certain embodiments, when M is Ge(II), Ge(IV)-$(X)_2$, Ca(II) or Mg(II):

$R_1$ and $R_2$ are independently hydrogen, halide, a nitro group, a nitrile group, an amine, an imine, an ether group, a silyl ether group or an acetylide group or optionally substituted alkyl, alkenyl, alkynyl, haloalkyl, aryl, heteroaryl, alicyclic or heteroalicyclic group;

$R_3$ is independently selected from optionally substituted alkylene, alkenylene, alkynylene, heteroalkylene, heteroalkenylene, heteroalkynylene, arylene, heteroarylene or cycloalkylene, wherein alkylene, alkenylene, alkynylene, heteroalkylene, heteroalkenylene, heteroalkynylene may optionally be interrupted by aryl, heteroaryl, alicyclic or heteroalicyclic;

$R_4$ is independently selected from H, or optionally substituted aliphatic, heteroaliphatic, alicyclic, heteroalicyclic, aryl, heteroaryl, alkylheteroaryl or alkylaryl;

$R_5$ is H, or optionally substituted aliphatic, heteroaliphatic, alicyclic, heteroalicyclic, aryl, heteroaryl, alkylheteroaryl or alkylaryl (preferably hydrogen);

$E_1$ is C, $E_2$ is O, S or NH or $E_1$ is N and $E_2$ is O;

G is absent or independently selected from a neutral or anionic donor ligand which is a Lewis base;

wherein when both instances of G are absent and all instances of $R_5$ are hydrogen, X is independently selected from $OC(O)R^Z$, $OSO(R^Z)_2$, $OSO_2R^Y$, $OSOR^T$, $OR^V$, phosphinate, hydroxyl, carbonate, nitrate or optionally substituted aryl, heteroaryl, alicyclic or heteroalicyclic; preferably when both instances of G are absent and all instances of $R_5$ are hydrogen, X is independently selected from $OC(O)R^Z$, $OSO(R^Z)_2$, $OSO_2R^Y$, $OR^V$, hydroxyl, carbonate, nitrate or optionally substituted aryl, heteroaryl, alicyclic or heteroalicyclic;

$R^Z$ is independently hydrogen or optionally substituted $C_{2-20}$aliphatic, $C_{2-20}$ haloaliphatic, heteroaliphatic, alicyclic, heteroalicyclic, aryl, alkylaryl or heteroaryl;

$R^Y$ is hydrogen or optionally substituted aliphatic, heteroaliphatic, alicyclic, heteroalicyclic, aryl, heteroaryl or alkylaryl with the proviso that $R^Y$ is not $C_7H_7$;

$R^V$ is optionally substituted aryl, haloaryl, heteroaryl, heteroaliphatic, alicyclic, alkylaryl or heteroaliyclic;

$R^T$ is hydrogen, or optionally substituted aliphatic, haloaliphatic, heteroaliphatic, alicyclic, heteroalicyclic, aryl, alkylaryl or heteroaryl;

and wherein when either one or both instances of G are not absent, or one or more instances of $R_5$ are not hydrogen, X is independently selected from $OC(O)R^x$, $OSO_2R^x$, $OSOR^x$, $OSO(R^x)_2$, $OR^x$, phosphinate, halide, nitrate, hydroxyl, carbonate, amido or optionally substituted aliphatic, heteroaliphatic, alicyclic, heteroalicyclic, aryl or heteroaryl; preferably when either one or both instances of G are not absent, or one or more instances of $R_5$ are not hydrogen, X is independently selected from $OC(O)R^x$, $OSO_2R^x$, $OSO(R^x)_2$, $OR^x$, halide, nitrate, hydroxyl, carbonate, amido or optionally substituted aliphatic, heteroaliphatic, alicyclic, heteroalicyclic, aryl or heteroaryl;

$R_x$ is independently hydrogen, or optionally substituted aliphatic, haloaliphatic, heteroaliphatic, alicyclic, heteroalicyclic, aryl, alkylaryl or heteroaryl.

Preferably, $R_1$, $R_2$, $R_3$, $R_4$, $R_5$, $R^x$, $R^V$, $R^Y$, $R^Z$ and $R^T$ are each independently optionally substituted by halogen, hydroxyl, nitro, carbonate, alkoxy, aryloxy, heteroaryloxy, amino, alkylamino, imine, nitrile, acetylide, or unsubstituted aliphatic, heteroaliphatic, alicyclic, heteroalicyclic, aryl or heteroaryl.

In certain embodiments, M is Zn(II), Cr(III)-X, Cr(II), Co(III)-X, Co(II), Mn(III)-X, Mn(II), Mg (II), Ti(II), Fe(II), Fe(III)-X, Al(III)-X, Ti(III)-X, V(III)-X or Ti(IV)-(X)$_2$ (preferably Zn(II), Fe(II), Fe(III)-X, Co(II) or Co(III)-X, more preferably Zn(II), Fe(II) or Fe(III)-X);

G is absent or independently selected from a neutral or anionic donor ligand which is a Lewis base;

$R_5$ is H, or optionally substituted aliphatic, alicyclic, aryl, or alkylaryl (preferably hydrogen);

$E_1$ is C, $E_2$ is O, S or NH or $E_1$ is N and $E_2$ is O; wherein i) when both instances of G are absent and all instances of $R_5$ are hydrogen, X is independently selected from $OC(O)R^Z$, $OSO(R^Z)_2$, $OSO_2R^Y$, $OSOR^T$, $OR^V$, phosphinate, hydroxyl, carbonate, nitrate or optionally substituted aryl, heteroaryl, alicyclic or heteroalicyclic; preferably when both instances of G are absent and all instances of $R_5$ are hydrogen, X is independently selected from $OC(O)R^Z$, $OSO(R^Z)_2$, $OSO_2R^Y$, $OR^V$, hydroxyl, carbonate, nitrate or optionally substituted aryl, heteroaryl, alicyclic or heteroalicyclic;

$R_1$ and $R_2$ are independently hydrogen, halide, a nitro group, a nitrile group, an imine, an ether group, a silyl ether group or an acetylide group or optionally substituted alkyl, alkenyl, alkynyl, haloalkyl, aryl or alicyclic group;

$R_3$ is independently selected from optionally substituted alkylene, alkenylene, alkynylene, arylene or cycloalkylene, wherein alkylene, alkenylene or alkynylene may optionally be interrupted by aryl or alicyclic;

$R_4$ is independently selected from H, or optionally substituted aliphatic, alicyclic, aryl, or alkylaryl;

$R^Z$ is independently hydrogen or optionally substituted $C_{2-20}$aliphatic, $C_{2-20}$haloaliphatic, heteroaliphatic, alicyclic, heteroalicyclic, aryl, alkylaryl or heteroaryl;

$R^Y$ is hydrogen or optionally substituted aliphatic, heteroaliphatic, alicyclic, heteroalicyclic, aryl, heteroaryl or alkylaryl with the proviso that $R^Y$ is not $C_7H_7$;

$R^V$ is optionally substituted aryl, haloaryl, heteroaryl, heteroaliphatic, alicyclic, alkylaryl or heteroaliyclic;

$R^T$ is hydrogen, or optionally substituted aliphatic, haloaliphatic, alicyclic, aryl or alkylaryl;

$R_1$, $R_2$, $R_3$ and $R_4$ are each independently optionally substituted by halogen, hydroxyl, nitro, carbonate, alkoxy, aryloxy, imine, nitrile, acetylide, unsubstituted aliphatic, unsubstituted alicyclic and unsubstituted aryl; and $R^V$, $R^Y$, $R^Z$ and $R^T$ are each independently optionally substituted by halogen, hydroxyl, nitro, carbonate, alkoxy, aryloxy, heteroaryloxy, amino, alkylamino, imine, nitrile, acetylide, or unsubstituted aliphatic, heteroaliphatic, alicyclic, heteroalicyclic, aryl or heteroaryl;

ii) when either one or both instances of G are not absent, X is independently selected from $OC(O)R^x$, $OSO_2R^x$, $OSOR^x$, $OSO(R^x)_2$, $OR^x$, phosphinate, halide, nitrate, hydroxyl, carbonate, amido or optionally substituted aliphatic, heteroaliphatic, alicyclic, heteroalicyclic, aryl or heteroaryl;

$R^x$ is independently hydrogen, or optionally substituted aliphatic, haloaliphatic, heteroaliphatic, alicyclic, heteroalicyclic, aryl, alkylaryl or heteroaryl;

$R_1$ and $R_2$ are independently hydrogen, halide, a nitro group, a nitrile group, an imine, an amine, an ether group, a silyl ether group, or an acetylide group or an optionally substituted alkyl, alkenyl, alkynyl, haloalkyl, aryl, heteroaryl, alicyclic or heteroalicyclic;

$R_3$ is optionally substituted alkylene, alkenylene, alkynylene, heteroalkylene, heteroalkenylene, heteroalkynylene, arylene, heteroarylene or cycloalkylene, wherein alkylene, alkenylene, alkynylene, heteroalkylene, heteroalkenylene and heteroalkynylene may optionally be interrupted by aryl, heteroaryl, alicyclic or heteroalicyclic;

$R_4$ is H, or optionally substituted aliphatic, heteroaliphatic, alicyclic, heteroalicyclic, aryl, heteroaryl, alkylheteroaryl or alkylaryl; and $R_1$, $R_2$, $R_3$, $R_4$, $R_5$ and $R^x$ are each independently optionally substituted by halogen, hydroxyl, nitro, carbonate, alkoxy, aryloxy, heteroaryloxy, amino, alkylamino, imine, nitrile, acetylide, or unsubstituted aliphatic, heteroaliphatic, alicyclic, heteroalicyclic, aryl or heteroaryl; or iii) when or one or more instances of $R_5$ are not hydrogen, X is independently selected from $OC(O)R^x$, $OSO_2R^x$, $OSOR^x$, $OSO(R^x)_2$, $OR^x$, phosphinate, halide, nitrate, hydroxyl, carbonate, amido or optionally substituted aliphatic, heteroaliphatic, alicyclic, heteroalicyclic, aryl or heteroaryl;

$R^x$ is independently hydrogen, or optionally substituted aliphatic, haloaliphatic, heteroaliphatic, alicyclic, heteroalicyclic, aryl, alkylaryl or heteroaryl;

$R_1$ and $R_2$ are independently hydrogen, halide, a nitro group, a nitrile group, an imine, an ether group, a silyl ether group or an acetylide group or optionally substituted alkyl, alkenyl, alkynyl, haloalkyl, aryl or alicyclic group;

$R_3$ is independently selected from optionally substituted alkylene, alkenylene, alkynylene, arylene or cycloalkylene, wherein alkylene, alkenylene or alkynylene may optionally be interrupted by aryl or alicyclic;

R$_4$ is independently selected from H, or optionally substituted aliphatic, alicyclic, aryl, or alkylaryl;

R$_1$, R$_2$, R$_3$, R$_4$ and R$_5$ are each independently optionally substituted by halogen, hydroxyl, nitro, carbonate, alkoxy, aryloxy, imine, nitrile, acetylide, unsubstituted aliphatic, unsubstituted alicyclic and unsubstituted aryl; and R$^x$ is independently optionally substituted by halogen, hydroxyl, nitro, carbonate, alkoxy, aryloxy, heteroaryloxy, amino, alkylamino, imine, nitrile, acetylide, or unsubstituted aliphatic, heteroaliphatic, alicyclic, heteroalicyclic, aryl or heteroaryl.

In certain embodiments, M is Ge(II), Ge(IV)-(X)$_2$, Ca(II) or Mg(II);

G is absent or independently selected from a neutral or anionic donor ligand which is a Lewis base;

R$_5$ is H, or optionally substituted aliphatic, alicyclic, aryl, or alkylaryl (preferably hydrogen);

E$_1$ is C, E$_2$ is O, S or NH or E$_1$ is N and E$_2$ is O; wherein i) when both instances of G are absent and all instances of R$_5$ are hydrogen, X is independently selected from OC(O)R$^Z$, OSO(R$^Z$)$_2$, OSO$_2$R$^Y$, OSOR$^T$, OR$^V$, phosphinate, hydroxyl, carbonate, nitrate or optionally substituted aryl, heteroaryl, alicyclic or heteroalicyclic; preferably when both instances of G are absent and all instances of R$_5$ are hydrogen, X is independently selected from OC(O)R$^Z$, OSO(R$^Z$)$_2$, OSO$_2$R$^V$, OR$^V$, hydroxyl, carbonate, nitrate or optionally substituted aryl, heteroaryl, alicyclic or heteroalicyclic;

R$_1$ and R$_2$ are independently hydrogen, halide, a nitro group, a nitrile group, an imine, an ether group, a silyl ether group or an acetylide group or optionally substituted alkyl, alkenyl, alkynyl, haloalkyl, aryl or alicyclic group;

R$_3$ is independently selected from optionally substituted alkylene, alkenylene, alkynylene, arylene or cycloalkylene, wherein alkylene, alkenylene or alkynylene may optionally be interrupted by aryl or alicyclic;

R$_4$ is independently selected from H, or optionally substituted aliphatic, alicyclic, aryl, or alkylaryl;

R$^Z$ is independently hydrogen or optionally substituted C$_{2-20}$aliphatic, C$_{2-20}$ haloaliphatic, heteroaliphatic, alicyclic, heteroalicyclic, aryl, alkylaryl or heteroaryl;

R$^Y$ is hydrogen or optionally substituted aliphatic, heteroaliphatic, alicyclic, heteroalicyclic, aryl, heteroaryl or alkylaryl with the proviso that R$^Y$ is not C$_7$H$_7$;

R$^V$ is optionally substituted aryl, haloaryl, heteroaryl, heteroaliphatic, alicyclic, alkylaryl or heteroaliyclic;

R$^T$ is hydrogen, or optionally substituted aliphatic, haloaliphatic, alicyclic, aryl or alkylaryl;

R$_1$, R$_2$, R$_3$ and R$_4$ are each independently optionally substituted by halogen, hydroxyl, nitro, carbonate, alkoxy, aryloxy, imine, nitrile, acetylide, unsubstituted aliphatic, unsubstituted alicyclic and unsubstituted aryl; and R$^V$, R$^Y$, R$^Z$ and R$^T$ are each independently optionally substituted by halogen, hydroxyl, nitro, carbonate, alkoxy, aryloxy, heteroaryloxy, amino, alkylamino, imine, nitrile, acetylide, or unsubstituted aliphatic, heteroaliphatic, alicyclic, heteroalicyclic, aryl or heteroaryl;

ii) when either one or both instances of G are not absent, X is independently selected from OC(O)R$^x$, OSO$_2$R$^x$, OSOR$^x$, OSO(R$^x$)$_2$, OR$^x$, phosphinate, halide, nitrate, hydroxyl, carbonate, amido or optionally substituted aliphatic, heteroaliphatic, alicyclic, heteroalicyclic, aryl or heteroaryl;

R$^x$ is independently hydrogen, or optionally substituted aliphatic, haloaliphatic, heteroaliphatic, alicyclic, heteroalicyclic, aryl, alkylaryl or heteroaryl;

R$_1$ and R$_2$ are independently hydrogen, halide, a nitro group, a nitrile group, an imine, an amine, an ether group, a silyl ether group, or an acetylide group or an optionally substituted alkyl, alkenyl, alkynyl, haloalkyl, aryl, heteroaryl, alicyclic or heteroalicyclic;

R$_3$ is optionally substituted alkylene, alkenylene, alkynylene, heteroalkylene, heteroalkenylene, heteroalkynylene, arylene, heteroarylene or cycloalkylene, wherein alkylene, alkenylene, alkynylene, heteroalkylene, heteroalkenylene and heteroalkynylene may optionally be interrupted by aryl, heteroaryl, alicyclic or heteroalicyclic;

R$_4$ is H, or optionally substituted aliphatic, heteroaliphatic, alicyclic, heteroalicyclic, aryl, heteroaryl, alkylheteroaryl or alkylaryl; and R$_1$, R$_2$, R$_3$, R$_4$, R$_5$ and R$^x$ are each independently optionally substituted by halogen, hydroxyl, nitro, carbonate, alkoxy, aryloxy, heteroaryloxy, amino, alkylamino, imine, nitrile, acetylide, or unsubstituted aliphatic, heteroaliphatic, alicyclic, heteroalicyclic, aryl or heteroaryl; or iii) when or one or more instances of R$_5$ are not hydrogen, X is independently selected from OC(O)R$^x$, OSO$_2$R$^x$, OSOR$^x$, OSO(R$^x$)$_2$, OR$^x$, phosphinate, halide, nitrate, hydroxyl, carbonate, amido or optionally substituted aliphatic, heteroaliphatic, alicyclic, heteroalicyclic, aryl or heteroaryl;

R$^x$ is independently hydrogen, or optionally substituted aliphatic, haloaliphatic, heteroaliphatic, alicyclic, heteroalicyclic, aryl, alkylaryl or heteroaryl;

R$_1$ and R$_2$ are independently hydrogen, halide, a nitro group, a nitrile group, an imine, an ether group, a silyl ether group or an acetylide group or optionally substituted alkyl, alkenyl, alkynyl, haloalkyl, aryl or alicyclic group;

R$_3$ is independently selected from optionally substituted alkylene, alkenylene, alkynylene, arylene or cycloalkylene, wherein alkylene, alkenylene or alkynylene may optionally be interrupted by aryl or alicyclic;

R$_4$ is independently selected from H, or optionally substituted aliphatic, alicyclic, aryl, or alkylaryl;

R$_1$, R$_2$, R$_3$, R$_4$ and R$_5$ are each independently optionally substituted by halogen, hydroxyl, nitro, carbonate, alkoxy, aryloxy, imine, nitrile, acetylide, unsubstituted aliphatic, unsubstituted alicyclic and unsubstituted aryl; and R$^x$ is independently optionally substituted by halogen, hydroxyl, nitro, carbonate, alkoxy, aryloxy, heteroaryloxy, amino, alkylamino, imine, nitrile, acetylide, or unsubstituted aliphatic, heteroaliphatic, alicyclic, heteroalicyclic, aryl or heteroaryl.

In certain embodiments, M is independently selected from Mg(II), Zn(II), Ca(II), Ge(II), Co(II), Mn(II), Ti(II), Fe(II), Cr(II), Cr(III)-X, Co(III)-X, Mn(III)-X, Fe(III)-X, Al(III)-X, Ti(III)-X, V(III)-X, Ge(IV)-(X)$_2$ or Ti(IV)-(X)$_2$, R$_1$ and R$_2$ are independently hydrogen, halide, a nitro group, a nitrile group, an imine, an ether group, a silyl ether group or an acetylide group or optionally substituted alkyl, alkenyl, alkynyl, haloalkyl, aryl or alicyclic group;

R$_3$ is independently selected from optionally substituted alkylene, alkenylene, alkynylene, arylene or cycloalkylene, wherein alkylene, alkenylene or alkynylene may optionally be interrupted by aryl or alicyclic;

R$_4$ is independently selected from H, or optionally substituted aliphatic, alicyclic, aryl, or alkylaryl;

R$_5$ is H, or optionally substituted aliphatic, alicyclic, aryl, or alkylaryl;

E$_1$ is C, E$_2$ is O, S or NH or E$_1$ is N and E$_2$ is O;

G is absent or independently selected from a neutral or anionic donor ligand which is a Lewis base;

X is independently selected from OC(O)R$^Z$, OSO(R$^Z$)$_2$, OSO$_2$R$^Y$, OSOR$^T$, OR$^V$, phosphinate, hydroxyl, carbonate, nitrate or optionally substituted aryl, heteroaryl, alicyclic or heteroalicyclic;

R$^Z$ is independently hydrogen or optionally substituted C$_{2\text{-}20}$aliphatic, C$_{2\text{-}20}$haloaliphatic, heteroaliphatic, alicyclic, heteroalicyclic, aryl, alkylaryl or heteroaryl;

R$^Y$ is hydrogen or optionally substituted aliphatic, heteroaliphatic, alicyclic, heteroalicyclic, aryl, heteroaryl or alkylaryl with the proviso that R$^Y$ is not C$_7$H$_7$;

R$^V$ is optionally substituted aryl, haloaryl, heteroaryl, heteroaliphatic, alicyclic, alkylaryl or heteroaliyclic;

R$^T$ is hydrogen, or optionally substituted aliphatic, haloaliphatic, alicyclic, aryl or alkylaryl;

R$_1$, R$_2$, R$_3$, R$_4$ and R$_5$ are each independently optionally substituted by halogen, hydroxyl, nitro, carbonate, alkoxy, aryloxy, imine, nitrile, acetylide, unsubstituted aliphatic, unsubstituted alicyclic and unsubstituted aryl; and R$^V$, R$^Y$, R$^Z$ and R$^T$ are each independently optionally substituted by halogen, hydroxyl, nitro, carbonate, alkoxy, aryloxy, heteroaryloxy, amino, alkylamino, imine, nitrile, acetylide, or unsubstituted aliphatic, heteroaliphatic, alicyclic, heteroalicyclic, aryl or heteroaryl.

In preferred embodiments, M is Mg(II), one or both G groups are present, or both G are absent and one or more instances of R$_5$ is not hydrogen, G is optionally substituted heteroaryl, X is halogen, phosphinate, or OC(O)R$^x$, R$^x$ is optionally substituted aryl, alicyclic or aliphatic (preferably C$_{1\text{-}6}$alkyl or C$_{1\text{-}6}$haloalkyl), R$_1$ is hydrogen or C$_{1\text{-}6}$alkyl, R$_2$ is hydrogen, R$_3$ is alkylene optionally substituted by C$_{1\text{-}6}$alkyl or aryl, R$_4$ is hydrogen, R$_5$ is independently hydrogen, or optionally substituted C$_{1\text{-}20}$aliphatic (preferably methyl or trifluoromethyl), E$_1$ is C and E$_2$ is O. Preferably, G is heteroaryl optionally substituted by amine (preferably dimethylamine) or C$_{1\text{-}6}$alkyl (preferably methyl), more preferably G is pyridine, N-methyl imidazole or 4-dimethylaminopyridine.

More preferably M is Mg(II), one or both G groups are present, or both G are absent and one or more instances of R$_5$ is not hydrogen, X is chlorine, bromine, iodine, phosphinate, or OC(O)R$^x$, R$^x$ is optionally substituted C$_{1\text{-}20}$aliphatic, C$_{1\text{-}20}$alicyclic or aryl, R$_1$ is hydrogen or tert-butyl, R$_2$ is hydrogen, R$_3$ is propylene or 2,2-dimethyl propylene, R$_5$ is hydrogen or methyl, E$_1$ is C and E$_2$ is O. In particularly preferred embodiments, X is acetate, trifluoroacetate, pivalate, benzoate, pentafluorobenzoate, chloride, bromide, hexanoate, octanoate, dodecanoate, adamantyl carboxylate, diphenyl phosphinate or bis(4-methoxy)phenyl phosphinate (preferably acetate).

In preferred embodiments, M is Zn(II), both G groups are absent, X is phosphinate or OC(O)R$^Z$, R$^Z$ is optionally substituted C$_{4\text{-}20}$ aliphatic, C$_{4\text{-}20}$ alicyclic or aryl, R$_1$ is hydrogen or C$_{1\text{-}6}$alkyl, R$_2$ is hydrogen, R$_3$ is alkylene optionally substituted by C$_{1\text{-}6}$alkyl or aryl, R$_4$ is hydrogen, R$_5$ is hydrogen, or optionally substituted C$_{1\text{-}20}$aliphatic (preferably trifluoromethyl or methyl), E$_1$ is C and E$_2$ is O. More preferably, M is Zn(II), both G groups are absent, X is benzoate, pentafluorobenzoate, hexanoate, octanoate, stearate, dodecanoate, adamantyl carboxylate, diphenyl phosphinate, bis(4-methoxy)phenyl phosphinate, dioctanyl phosphinate or pivalate, R$_1$ is hydrogen or tert-butyl, R$_2$ is hydrogen, R$_3$ is propylene or 2,2-dimethyl propylene, R$_4$ is hydrogen, R$_5$ is hydrogen, E$_1$ is C and E$_2$ is O.

In preferred embodiments, M is Zn(II), one or both G groups are present and are selected from optionally substituted heteroaryl, and halogen, X is chlorine, bromine, iodine, phosphinate, or OC(O)R$^x$, R$^x$ is optionally substituted C$_{1\text{-}20}$aliphatic, C$_{1\text{-}20}$alicyclic or aryl, R$_1$ is hydrogen or tert-butyl, R$_2$ is hydrogen, R$_3$ is propylene or 2,2-dimethyl propylene, R$_5$ is hydrogen or independently optionally substituted C$_{1\text{-}20}$aliphatic (preferably methyl or trifluoromethyl), E$_1$ is C and E$_2$ is O. In particularly preferred embodiments, X is acetate, trifluoroacetate, pivalate, benzoate, pentafluorobenzoate, chloride, bromide, hexanoate, octanoate, dodecanoate, adamantyl carboxylate, diphenyl phosphinate or bis(4-methoxy)phenyl phosphinate (preferably acetate). It will be appreciated that when G is a halogen, a counterion must be present. Preferably, the counterion is [H—B]$^+$, wherein B is preferably selected from NEt$_3$, 1,8-diazabicyclo[5.4.0]undec-7-ene (DBU) and 7-methyl-1,5,7-triazabicyclo[4.4.0]dec-5-ene (MTBD).

In preferred embodiments, when M is Co(II), one or both G groups are present and are selected from optionally substituted heteroaryl, and halogen, X is halogen or OC(O)R$^x$, R$^x$ is optionally substituted C$_{1\text{-}20}$aliphatic, C$_{1\text{-}20}$alicyclic or aryl, R$_1$ is hydrogen or C$_{1\text{-}6}$alkyl, R$_2$ is hydrogen, R$_3$ is alkylene optionally substituted by C$_{1\text{-}6}$alkyl or aryl, R$_4$ is hydrogen, R$_5$ is hydrogen or optionally substituted C$_{1\text{-}20}$aliphatic (preferably trifluoromethyl or methyl), E$_1$ is C and E$_2$ is O. In preferred embodiments, G is heteroaryl optionally substituted by C$_{1\text{-}6}$alkyl (preferably methyl) or amine (preferably dimethylamine). More preferably, M is Co(II), either one or both instances of G are present and are pyridine, dimethylaminopyridine (preferably 4-dimethylaminopyridine), methylimidazole (preferably N-methylimidazole), chlorine, bromine or iodine (preferably chlorine or bromine), X is chlorine, bromine or iodine (preferably chlorine or bromine), R$_1$ is hydrogen or tert-butyl, R$_3$ is propylene or 2,2-dimethyl propylene, R$_4$ is hydrogen, R$_5$ is hydrogen, trifluoromethyl or methyl, E$_1$ is C and E$_2$ is O. It will be appreciated that when G is a halogen, a counterion must be present. Preferably, the counterion is [H—B]$^+$, wherein B is preferably selected from NEt$_3$, 1,8-diazabicyclo[5.4.0]undec-7-ene (DBU) and 7-methyl-1,5,7-triazabicyclo[4.4.0]dec-5-ene (MTBD).

In preferred embodiments, M is Fe(II) or Fe(III)-X, one or both G groups are present and are selected from optionally substituted heteroaryl and halogen, X is halogen or OC(O)R$^x$, R$^x$ is optionally substituted C$_{1\text{-}20}$aliphatic, C$_{1\text{-}20}$alicyclic or aryl R$_1$ is hydrogen or C$_{1\text{-}6}$alkyl, R$_2$ is hydrogen, R$_3$ is alkylene optionally substituted by C$_{1\text{-}6}$alkyl or aryl, R$_4$ is hydrogen, R$_5$ is hydrogen or optionally substituted C$_{1\text{-}20}$aliphatic (preferably trifluoromethyl or methyl), E$_1$ is C and E$_2$ is O. In particularly preferred embodiments, G is a heteroaryl optionally substituted by C$_{1\text{-}6}$alkyl (preferably methyl) or amine (preferably dimethylamine). More preferably, when M is Fe(II) or Fe(III)-X, either one or both instances of G are present and are pyridine, dimethylaminopyridine (preferably 4-dimethylaminopyridine), methylimidazole (preferably N-methylimidazole), chlorine, bromine or iodine (preferably chlorine or bromine), X is chlorine, bromine or iodine (preferably chlorine or bromine), R$_1$ is hydrogen or tert-butyl, R$_3$ is propylene or 2,2-dimethyl propylene, R$_4$ is hydrogen, R$_5$ is hydrogen, E$_1$ is C and E$_2$ is O. It will be appreciated that when G is a halogen, a counterion must be present. Suitable counterions are described in the application above.

Exemplary catalysts according to the sixth aspect include:
[L$^1$Mg$_2$Cl$_2$(methylimidazole)],
[L$_1$Mg$_2$Cl$_2$(dimethylaminopyridine)],
[L$_1$Mg$_2$Br$_2$(dimethylaminopyridine)],
[L$^1$Zn$_2$(OOCC(CH$_3$)$_3$)$_2$],
[L$^1$Zn$_2$(OC$_6$H$_5$)$_2$],
[L$^1$Zn$_2$(pentafluorobenzoate)$_2$]
[L$^1$Zn$_2$(adamantyl carboxylate)$_2$]
[L$^1$Zn$_2$(diphenyl phosphinate)$_2$]
[L$^1$Zn$_2$(bis(4-methoxy)phenyl phosphinate)$_2$]
[L$^4$Mg$_2$(OAc)$_2$]
[L$^1$Zn$_2$(hexanoate)$_2$],
[L$^1$Zn$_2$(octanoate)$_2$],
[L$^1$Zn$_2$(dodecanoate)$_2$], and

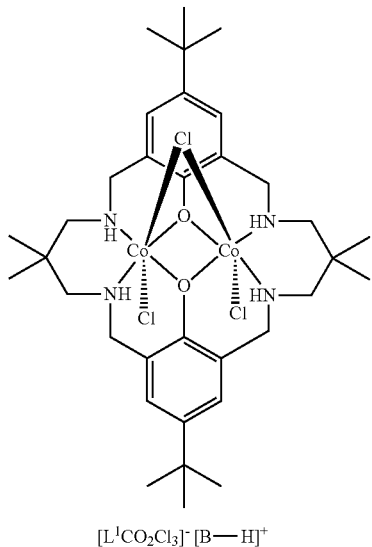

[L$^1$Co$_2$Cl$_3$]$^-$ [B—H]$^+$

[B—H]$^+$ represents any counterion, for example,
B may be NEt$_3$, 1,8-diazabicyclo[5.4.0]undec-7-ene (DBU),
7-methyl-1,5,7-triazabicyclo[4.4.0]dec-5-ene (MTBD), etc and

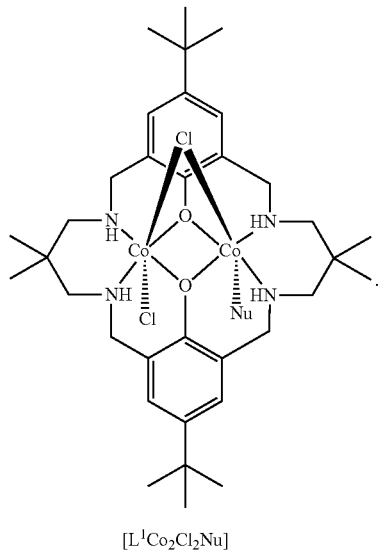

[L$^1$Co$_2$Cl$_2$Nu]

Nu = N-methylimidazole
 = pyridine
 = dimethylaminopyridine

A catalyst of the sixth aspect is preferably a catalyst of formula (III) as described above, with the proviso that the catalyst is not [Co$_2$L$^1$Cl$_2$(CH$_3$OH)$_2$].H$_2$O, [Co$_2$L$^1$Br$_2$(CH$_3$OH)$_2$].H$_2$O, [Mn$_2$Cl$_2$(CH$_3$OH)$_2$]. H$_2$O, [Mn$_2$L$^1$Br$_2$(CH$_3$OH)]. H$_2$O, [Co$^{II}$Co$^{III}$L$^1$Cl$_2$Br(CH$_3$OH)].0.5CH$_2$Cl$_2$, [Mn$^{II}$Mn$^{III}$L$^1$Cl$_2$Br(CH$_3$OH)], [Fe$^{III}$Zn$^{II}$L$^1$(µ-OAc)(OAc)(H$_2$O)](ClO$_4$) H$_2$O, [Fe$^{III}$Co$^{II}$L$^1$(µ-OAc)(OAc)(H$_2$O)]ClO$_4$.2H$_2$O, or [Fe$^{III}$Mn$^{II}$L$^1$(µ-OAc)(OAc)(H$_2$O)](ClO$_4$).2H$_2$O.

It will be appreciated that the various features described above for the catalyst of the sixth aspect may be present in combination mutatis mutandis. All preferred features of the sixth aspect of the invention apply to the first aspect of the invention mutatis mutandis.

In a further aspect of the invention, there is provided a process for the synthesis of a polycarbonate, the process comprising the step of reacting carbon dioxide with at least one epoxide in the presence of a catalyst of formula (III) as defined in respect of the sixth aspect of the invention and a chain transfer agent as defined in respect of the first aspect of the invention. Features of the process of the first aspect of the invention apply equally to this further aspect mutatis mutandis.

The invention may be put into practice in various ways and a number of specific embodiments will be described in the following non-limiting examples.

EXAMPLES

Example 1

Synthesis of Catalysts

Materials and Methods

The ligand H$_2$L$^1$, used in the following examples, has the following structure:

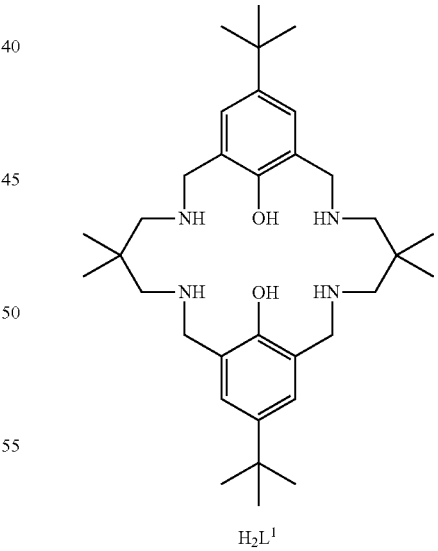

H$_2$L$^1$

The ligand H$_2$L$^1$ may be prepared as described in WO2009/130470, the entire contents of which are incorporated herein by reference.

General Procedure for the Synthesis of [L$^1$Mg$_2$X$_2$(G)]

H$_2$L$^1$ (0.20 g, 0.36 mmol) was dissolved in THF (10 mL) and transferred into a Schlenk tube containing KH (0.44 g, 1.1 mmol) and cooled to −78° C., under nitrogen. The suspension was allowed to warm to room temperature and left to stir for 1 hour. Any excess KH was filtered off, the nucleophile group G (0.36 mmol) was added to the solution and left to stir for 5 minutes, after which $MgX_2$ (0.72 mmol) was added, slowly. The reaction was stirred for 16 hours, before the solution was filtered by centrifugation and the solvent removed in vacuo.

Figure 2:
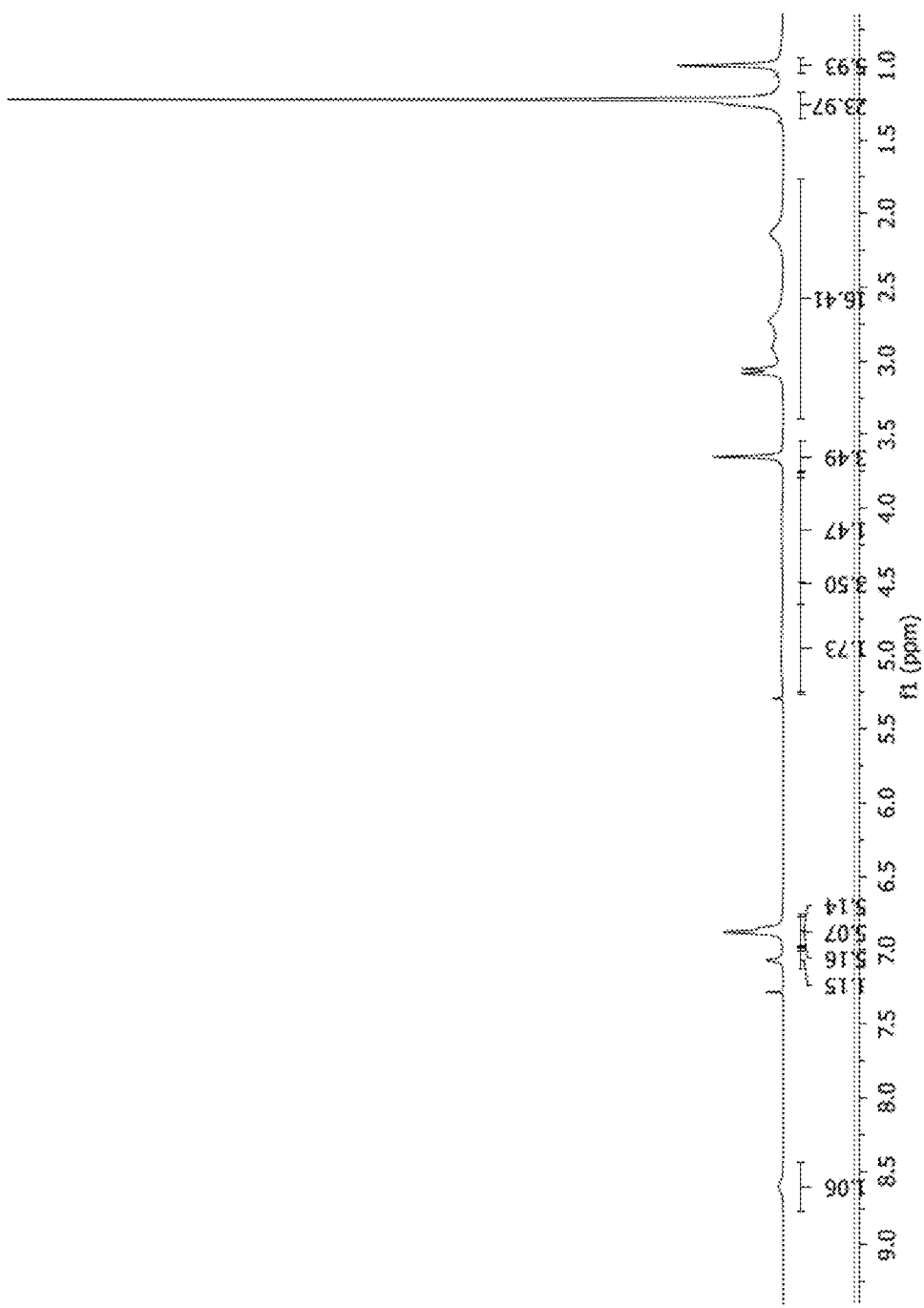
FIG. 2 shows the $^1H$ NMR spectrum of $[L^1Mg_2Cl_2(methylimidazole)]$

[$L^1Mg_2Cl_2$(methylimidazole)] (0.21 g, 0.28 mmol, 77%) Anal. Calc. for $C_{38}H_{60}Cl_2Mg_2N_6O_2$: C, 60.66; H, 8.04; N, 11.17. Found: C, 60.57; H, 8.12; N, 11.03. $^1$H NMR (FIG. 2) (400 MHz, $CDCl_3$) δ 8.60 (s, 1H, MeIm), 7.07 (s, 1H, MeIm), 6.88 (br s, 5H, Ar—H+MeIm), 5.03 (s, 2H, NH), 4.08 (s, 2H, NH), 3.65 (s, 3H, MeIm), 3.39-1.76 (m, 16H, $CH_2$), 1.22 (s, 24H, Ar—C—$CH_3$+N—C—$CH_3$), 0.99 (s, 6H, C—$CH_3$). $^{13}$C NMR (101 MHz, $CDCl_3$) δ: 159.1, 142.7, 137.3, 127.7, 126.3, 125.2, 120.3, 62.9, 55.6, 34.3, 34.1, 33.4, 31.6, 28.2, 21.0. m/z (LSIMS)=756 (100%, [M-Cl-methylimidazole]$^+$.

[$L_1Mg_2Cl_2$(dimethylaminopyridine)] (0.2 g, 0.26 mmol, 72%). $^1$H NMR (400 MHz, $CDCl_3$) δ 8.59 (d, J=6.7, 2H, DMAP), 6.85 (s, 4H, Ar—H), 6.55 (d, J=6.9, 2H, DMAP), 4.53 (br s, 4H, NH), 3.06 (d, J=12.0, 4H, N—$CH_2$), 2.94 (s, 10H, N—$CH_3$+N—$CH_2$), 2.74 (s, 4H, C—$CH_2$), 2.19 (s, 4H, C—$CH_2$), 1.27 (d, J=10.6, 6H, C—$CH_3$), 1.22 (s, 18H, Ar—C—$CH_3$), 1.00 (s, 6H, C—$CH_3$). $^{13}$C NMR (101 MHz, $CDCl_3$) δ: 159.0, 154.6, 149.9, 137.2, 127.7, 125.1, 107.1, 62.9, 55.6, 39.0, 34.5, 33.4, 31.6, 28.2, 21.2. m/z (LSIMS)= 756 (100%, [M-Cl-dimethylaminopyridine]$^+$).

Figure 3:
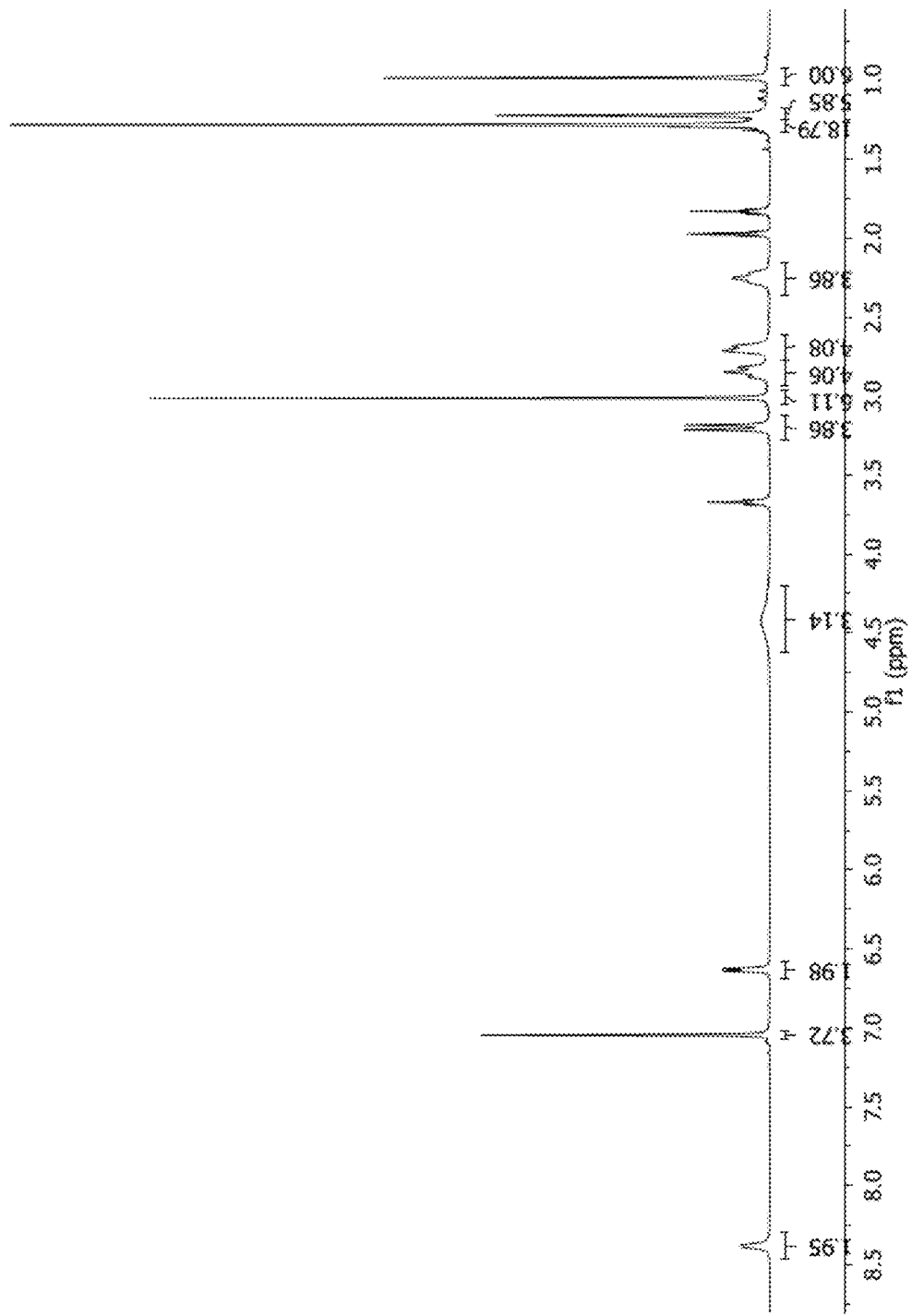
FIG. 3 shows the $^1H$ NMR spectrum of $[L^1Mg_2Br_2(dimethylaminopyridine)]$

[$L_1Mg_2Br_2$(dimethylaminopyridine)] (0.27 g, 0.3 mmol, 84%) Anal. Calc. for $C_{41}H_{64}Br_2Mg_2N_6O_2$: C, 55.87; H, 7.32; N, 9.53. Found: C, 55.78; H, 7.34; N, 9.48. $^1$H NMR (FIG. 3) (400 MHz, $CD_3CN$) δ 8.29 (s, 2H, DMAP), 7.05 (s, 4H, Ar—H), 6.61 (d, J=6.5, 2H, DMAP), 4.38 (s, 4H, NH), 3.20 (d, J=12.2, 4H, $CH_2$), 3.00 (s, 6H, N—$CH_3$), 2.94-2.55 (m, 8H, $CH_2$), 2.24 (s, 4H, C—$C_{H2}$), 1.28 (s, 18H, Ar—C—$CH_3$), 1.20 (s, 6H, C—$CH_3$), 0.98 (s, 6H, C—$CH_3$). $^{13}$C NMR (101 MHz, $CDCl_3$) δ: 158.9, 149.5, 137.6, 128.1, 124.9, 124.4, 106.7, 62.3, 55.0. 38.3, 33.9, 33.2, 30.9, 27.3, 20.9. m/z (LSIMS)=678 (100%, [M Br dimethylaminopyridine]$^+$).

Synthesis of [$L^1Zn_2(F_3CCOO)_2$]

$H_2L^1$ (0.25 g, 0.45 mmol) was dissolved in methanol (20 mL) and $Zn(CF_3COO)_2$ (0.26 g, 0.90 mmol) was added. The mixture was stirred for 18 hours and the methanol removed in vacuo. The product was taken up in dichloromethane, filtered, and the solvent removed in vacuo. The product, a white powder, was dried in a vacuum oven, in the presence of diphosphorus pentoxide, overnight.

Figure 4:
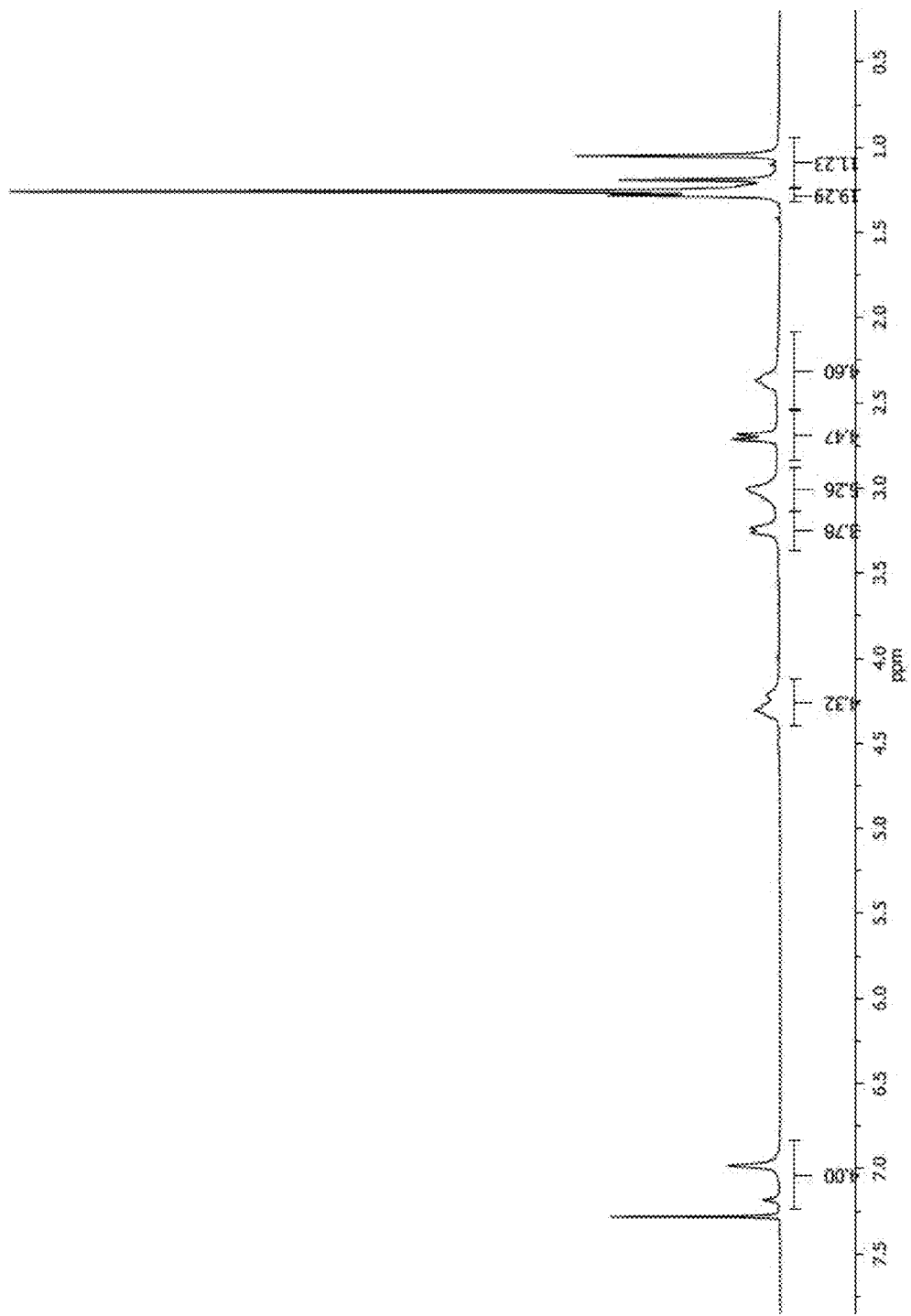
FIG. 4 shows the $^1H$ NMR spectrum of $[L^1Zn_2(O_2CCF_3)_2]$ in $CDCl_3$

[$L^1Zn_2(CF_3COO)_2$] (white powder; 0.30 g, 72%). Found: C, 50.2; H, 6.1; N, 6.1. Calc. for $C_{38}H_{54}F_6N_4O_6Zn_2$: C, 50.3; H, 6.0; N, 6.2. $ν_{max}/cm^{-1}$ 3204 (N—H), 1673 (C═O). (FIG. 4) $δ_H$ (400 MHz; $CDCl_3$) Major isomer: 6.98 (s, 4H, Ar—H), 4.15-4.37 (br s, 4H, N—H), 3.25 (d, J=11.2 Hz, 4H, N—$CH_2$—Ar), 3.00 (br s, 4H, N—$CH_2$—Ar), 2.71 (d, J=11.5 Hz, 4H, N—$CH_2$—C), 2.37 (br s, 4H, N—$CH_2$—C), 1.26 (s, 18H, Ar—$CH_3$) 1.19 (s, 6H N—C—$CH_3$), 1.05 (s, 6H N—C—$CH_3$) $δ_C$ (400 MHz; $CDCl_3$) 161.69, 136.91, 127.79, 122.81, 114.69, 62.93, 55.84, 33.86, 33.52, 31.54, 28.36, 20.72. $δ_F$ (400 MHz; $d^4$-methanol) −78.13 (s). m/z (FAB) 793 ([M-OAc]$^+$, 100%).

Synthesis of [$L^1Zn_2(OOCC(CH3)_3)_2$]

In a vial in the glovebox, KH (58 mg, 1.45 mmol) was added by small portions to a solution of ligand $H_2L^1$ (200 mg, 0.36 mmol) in cold THF (10 mL). After 4 h of stirring, the reaction mixture was centrifuged then [$Zn(OOCC(CH3)_3)_2$] (194 mg, 0.72 mmol) was added to the colourless solution, instantly producing a cloudy white mixture, which was left to stir at room temperature for 20 h. THF was removed in vacuo, then 10 mL of DCM added. Potassium carboxylate salts were eliminated by centrifugation, and the white solid residue was finally washed with hexane (3×5 mL), then dried under vacuum for 20 h.

Figure 5:
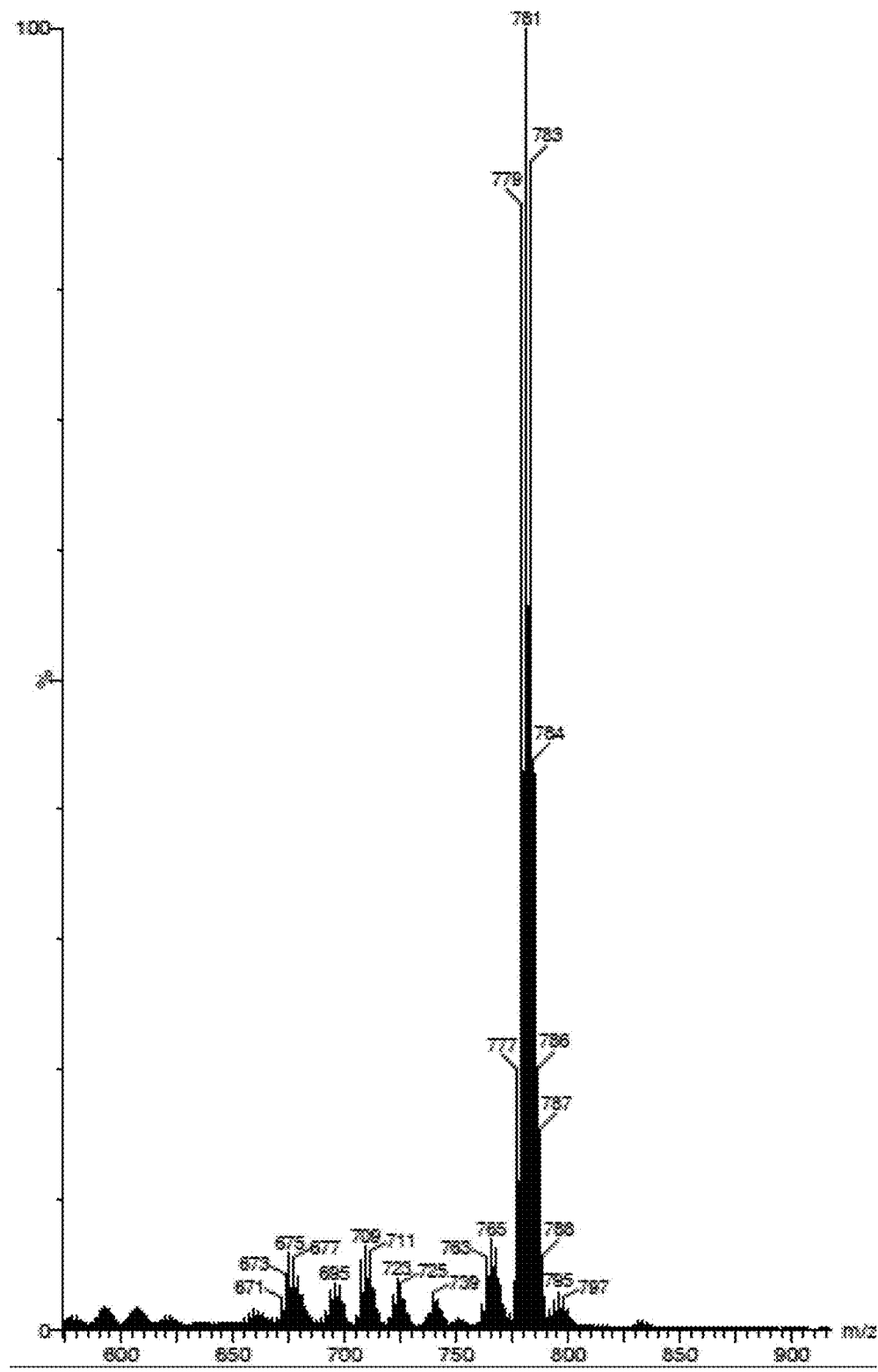
FIG. 5 shows the LSIMS spectrum of $[L^1Zn_2(OOCC(CH3)_3)_2]$

[$L^1Zn_2(OOCC(CH3)_3)_2$] (white powder, 300 mg, 0.46 mmol, 94%). m/z (LSIMS) (FIG. 5): 781 ([M-OOCC(CH3)_3]$^+$, 100%).). $δ_H$ (400 MHz; $CDCl_3$) 6.88-6.97 (m, 4H, Ar—H), 2.46-4.59 (m, 20H, N—$CH_2$—Ar and N—H), 0.53-1.37 (m, 48H, Ar—$CH_3$) ppm. Anal. Calcd for $C_{44}H_{72}Zn_2N_4O_6$: C, 59.79; H, 8.21; N, 6.34. Found: C, 59.68; H, 8.15; N, 6.35.

Synthesis of [$L^1Zn_2(OC_6H_5)_2$]

In a vial in the glovebox, [$Zn(OC_6H_5)(C_2H_5)$] (136 mg, 0.72 mmol) was added by small portions to a solution of ligand $H_2L^1$ (200 mg, 0.36 mmol) in cold THF (10 mL), instantly producing a white precipitate, and the reaction mixture was left to stir at room temperature for 20 h. The precipitate was separated by centrifugation and diluted with 10 mL of DCM. The cloudy solution was centrifuged and the DCM dried in vacuo. The white solid residue was finally washed with hexane (3×5 mL), then dried under vacuum for 20 h.

[$L^1Zn_2(OC_6H_5)_2$] (white powder, 273 mg, 0.31 mmol, 87%). $δ_H$ (400 MHz; $CDCl_3$) 6.88-6.97 (m, 4H, Ar—H), 2.46-4.59 (m, 20H, N—$CH_2$—Ar and N—H), 0.53-1.37 (m, 48H, Ar—$CH_3$) ppm. Anal. Calcd for $C_{46}H_{64}Zn_2N_4O_4$: C, 63.66; H, 7.43; N, 6.46. Found: C, 63.59; H, 7.38; N, 6.45.

General Procedure for the Synthesis of [$L^1Co_2Cl_3$]$^-$[B—H]$^+$ $H_2L^1$ (0.25 g, 0.45 mmol) was dissolved in THF (10 mL) in a Schlenk tube. The base (0.9 mmol) was added to the solution and left to stir for 1 hour. $CoCl_2$ (0.12 g, 0.9 mmol) was added to the solution, slowly, to prevent formation of [$L^1Co_3Cl_4$], and the solution was left stirring overnight, after which a purple solution was found, with a white precipitate. The precipitate was filtered and the solvent removed, in vacuo, to yield a pink powder which was dried, under vacuum, for several hours.

Figure 6:
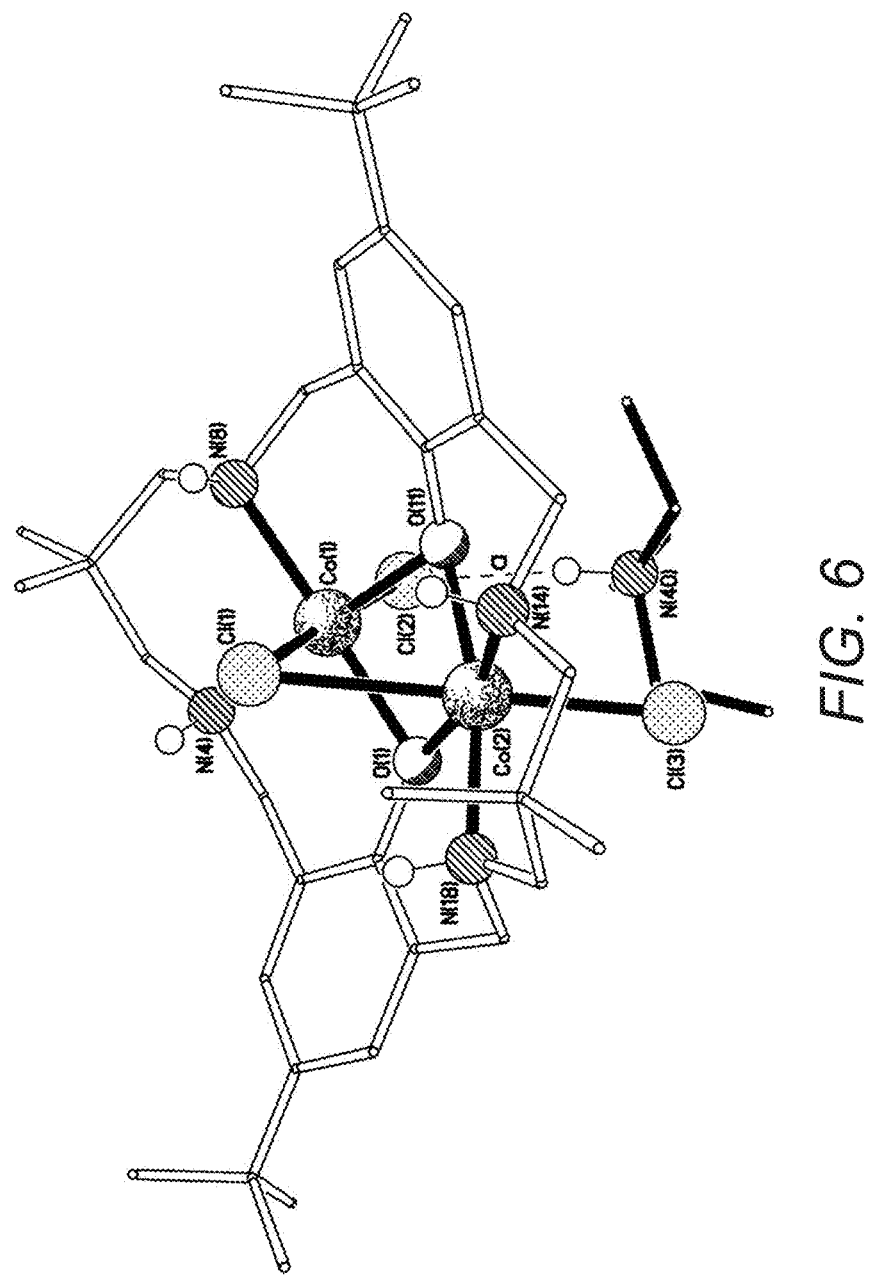
FIG. 6 shows the molecular structure of $[L^1Co_2Cl_3][HNEt_3]$

[$L^1Co_2Cl_3$][$HNEt_3$] (FIG. 6) (0.33 g, 0.38 mmol, 84%): m/z (LSI$^+$): 102 (100%, [$HNEt_3$]$^+$), (ESI$^-$): 803 (100%, [$L^1Co_2(HCO_2)_3$]$^-$, 793 (20%, [$L^1Co_2Cl(HCO_2)_2$]$^-$). Anal. Calc. for $C_{40}H_{70}Cl_3Co_2N_5O_2$: C, 54.77; H, 8.04; N, 7.98. Found: C, 54.84; H, 7.98; N, 8.02. UV-Vis $λ_{max}$/nm ($ε$/$dm^3$ $mol^{-1}cm^{-1}$): 473 (67.9), 541 (61.8), 565 (52.3).

[$L^1Co_2Cl_3$][HDBU] (0.33 g, 0.0.36 mmol, 79%): m/z: (LSI$^+$): 153 (100%, [H-DBU]$^+$), (ESI$^-$): 803 (100%, [$L^1Co_2(HCO_2)_3$]$^-$), 793 (25%, [$L^1Co_2Cl(HCO_2)_2$]$^-$). Anal. Calc. for $C_{43}H_{71}Cl_3Co_2N_6O_2$: C, 55.64; H, 7.71; N, 9.05. Found: C, 55.69; H, 7.79; N, 9.08.

[$L^1Co_2Cl_3$][HMTBD] (0.31 g, 0.33 mmol, 74%): m/z: (LSI$^+$): 154 (100%, [H-MTBD]$^+$), m/z (ESI$^-$) 803 (100%, [$L^1Co_2(HCO_2)_3$]$^-$, 793 (20%, [$L^1Co_2Cl(HCO_2)_2$]$^-$). Anal. Calc. for $C_{42}H_{70}Cl_3Co_2N_7O_2$: C, 54.28; H, 7.59; N, 10.55%. Found: C, 54.16; H, 7.65; N, 10.41%.

General Procedure for the Synthesis of [L$^1$Co$_2$Cl$_2$(G)]

H$_2$L$^1$ (0.40 g, 0.72 mmol) was dissolved in THF (10 mL) and transferred into a Schlenk tube containing KH (0.87 g, 2.20 mmol) and cooled to −78° C., under nitrogen. The suspension was allowed to warm to room temperature and left to stir for 1 hour. Any excess KH was filtered, the nucleophile group G (0.72 mmol) was added to the solution and left to stir for 5 minutes, after which CoCl$_2$ was added, slowly. The solution initially turned dark blue on addition, but after being left to stir overnight, a dark red solution evolved. The solution was filtered, and the solvent removed in vacuo.

Figure 7:
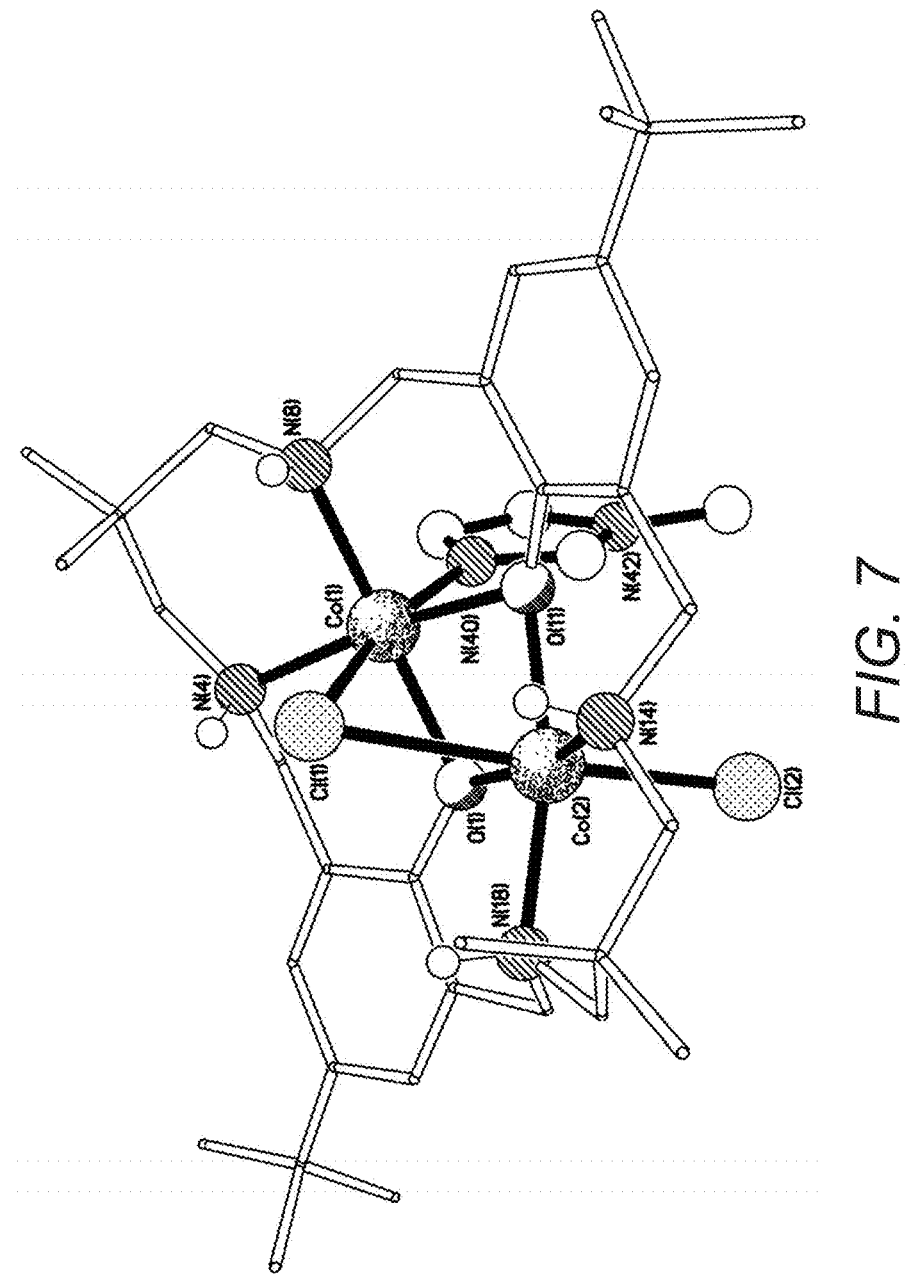
FIG. 7 shows the molecular structure of $[L^1Co_2Cl_2(methylimidazole)]$

[L$^1$Co$_2$Cl$_2$(pyridine)] (FIG. 7) (0.32 g, 0.39 mmol, 54%): m/z (LSI$^+$): 703 (100%, [L$^1$Co$_2$Cl]$^+$). Anal. Calc. for C$_{38}$H$_{60}$Cl$_2$Co$_2$N$_6$O$_2$: C, 55.54; H, 7.36; N, 10.23. Found: C, 55.68; H, 7.50; N, 10.05.

[L$^1$Co$_2$Cl$_2$(methylimidazole)] (0.47 g, 0.54 mmol, 75%): m/z (LSI$^+$): 703 (100%, [L$^1$Co$_2$Cl]$^+$). Anal. Calc. for C$_{41}$H$_{64}$Cl$_2$Co$_2$N$_6$O$_2$: C, 57.15; H, 7.49; N, 9.75. Found: C, 57.19; H, 7.59; N, 9.63. UV-Vis $\lambda_{max}$/nm ($\epsilon$/dm$^3$ mol$^{-1}$cm$^{-1}$): 473 (95.7), 538 (82.4).

[L$^1$Co$_2$Cl$_2$(dimethylaminopyridine)] (0.42 g, 0.53 mmol, 70%): m/z (LSI$^+$): 703 (100%, [L$^1$Co$_2$Cl]$^+$). Anal. Calc. for C$_{39}$H$_{59}$Cl$_2$Co$_2$N$_5$O$_2$: C, 57.22; H, 7.26; N, 8.55. Found: C, 57.12; H, 7.26; N, 8.46. UV-Vis $\lambda_{max}$/nm ($\epsilon$/dm$^3$ mol$^{-1}$cm$^{-1}$): 474 (95.9), 509 (78.9), 535 (76.3).

Example 2

Copolymerisation of CO$_2$ and an Epoxide

General CO$_2$/Cyclohexene Oxide Copolymerisation Procedure

All low pressure catalytic reactions were carried out in magnetically stirred Schlenk tubes, using standard Schlenk techniques. The Schlenk tubes were dried, in an oven at 140° C., for 20 h before any use. In a typical reaction cyclohexene oxide (2.5 mL, 24.7 mmol), and the catalyst were added to a Schlenk tube. The cyclohexene oxide was rapidly de-gassed, before being left stirring under 1 atm CO$_2$ (continuously fed using a reserve cylinder), at 80° C., for 24 h. At the end of the reaction the crude reaction mixture was then taken up in CH$_2$Cl$_2$ and a 0.2 mL of a 5% solution of HCl/MeOH was added. The solution was evaporated in air, after which the product was dried, in vacuo, overnight. No further purification of the product was undertaken as the vacuum was sufficient to remove unreacted cyclohexene oxide. Selectivity was determined by normalisation of the integrals of the methylene protons resonances in the $^1$H NMR spectra, including the copolymer carbonate linkages (broad signal δ=4.65 ppm), copolymer ether linkages (broad signal δ=3.45 ppm), and cyclic carbonate (multiplets: δ=3.9 ppm (trans-CHC) or 4.63 ppm (cis-CHC)). Conversion was calculated as [(mass of the isolated product weight of the catalyst)/142.1]/moles of starting CHO. Turn-over-number (TON) was calculated as conversion/moles catalyst. Turn-over-frequency (TOF) was calculated as TON/time of reaction (in h).

TABLE 1

Catalytic activities of complexes synthesized in Example 1

| Catalyst | Time (h) | TON | TOF (h$^{-1}$) | % carbonate | % polymer | Mn | PDI |
| --- | --- | --- | --- | --- | --- | --- | --- |
| L$^1$Mg$_2$Cl$_2$(MeIm) | 24 | 144 | 6 | >99 | 92 | 10600/4800 | 1.01/1.05 |
| L$^1$Mg$_2$Cl$_2$(DMAP) | 24 | 216 | 9 | >99 | 96 | 14900/6800 | 1.04/1.08 |
| L$^1$Mg$_2$Br$_2$(DMAP) | 24 | 312 | 13 | >99 | 94 | 11000/3000 | 1.03/1.10 |
| L$^1$Zn$_2$(O$_2$CC(F)$_3$)$_2$ | 24 | 477 | 20 | 98 | 95 | 9200 | 1.38 |
| L$^1$Zn$_2$(O$_2$CC(CH$_3$)$_3$)$_2$ | 8 | 316 | 40 | >99 | 98.5 | — | — |
| L$^1$Zn$_2$(O$_2$CC(CH$_3$)$_3$)$_2$ | 24 | 611 | 26 | >99 | 95 | 11000/4200 | 1.03/1.22 |
| L$^1$Zn$_2$(OC$_6$H$_5$)$_2$ | 20 | 520 | 26 | >99 | 91 | 5900 | 1.48 |
| K[(L$^1$Co$_2$Cl$_2$)Cl] | 6 | 93 | 15.5 | >99 | >99 | 5900 | 1.32 |
| [L$^1$Co$_2$Cl$_3$][HNEt$_3$] | 3.5 | 363 | 104 | >99 | >99 | 6500 | 1.28 |
| [L$^1$Co$_2$Cl$_3$][DBU-H] | 5 | 350 | 70 | 98 | 98 | 7900 | 1.34 |
| [L$^1$Co$_2$Cl$_3$][MTBD-H] | 3.5 | 371 | 106 | >99 | >99 | 8800/3900 | 1.03/1.12 |
| L$^1$Co$_2$Cl$_2$(MeIm) | 3 | 313 | 104 | >99 | >99 | 7100/1400 | 1.02/1.16 |
| L$^1$Co$_2$Cl$_2$(DMAP) | 6 | 100 | 20 | — | — | oligomers | — |
| L$^1$Co$_2$Cl$_2$(py) | 2.5 | 404 | 161 | >99 | >99 | 33100/14300/6400 | 1.03/1.04/1.19 |
| L$^1$Co$_2$Cl$_2$(py)[a] | 5 | 803 | 160 | >99 | >99 | 24600/9600/3900 | 1.06/1.03/1.18 |
| L$^1$Co$_2$Cl$_2$(py)[b] | 6 | 1205 | 201 | >99 | >99 | 9600/3500 | 1.05/1.20 |

Copolymerisation conditions: Cat (0.1 mol % - 1:1000), 80° C., 1 atm CO$_2$.

[a]Catalyst loading 0.05 mol % (1:2000).

[b]Catalyst loading 0.025 mol % (1:4000).

Example 3

Polymerisation of $CO_2$ and an Epoxide in the Presence of a Chain Transfer Agent (CTA) and Subsequent Reactions with Further Monomers Experimental Details for CTA Experiments with [$L^1Zn_2$ $(OAc)_2$] (Complex 1)

An oven-dried Schlenk tube was charged with catalyst (x mmol), CHO (2.5 mL, 25 mmol) and a CTA (x mmol) under nitrogen. The Schlenk tube was evacuated and backfilled with $CO_2$ (1 atm) three times, before being left under a constant flow of $CO_2$. The reaction was heated to temperature and stirred under a constant flow of $CO_2$ for the desired time.

Figure 8:
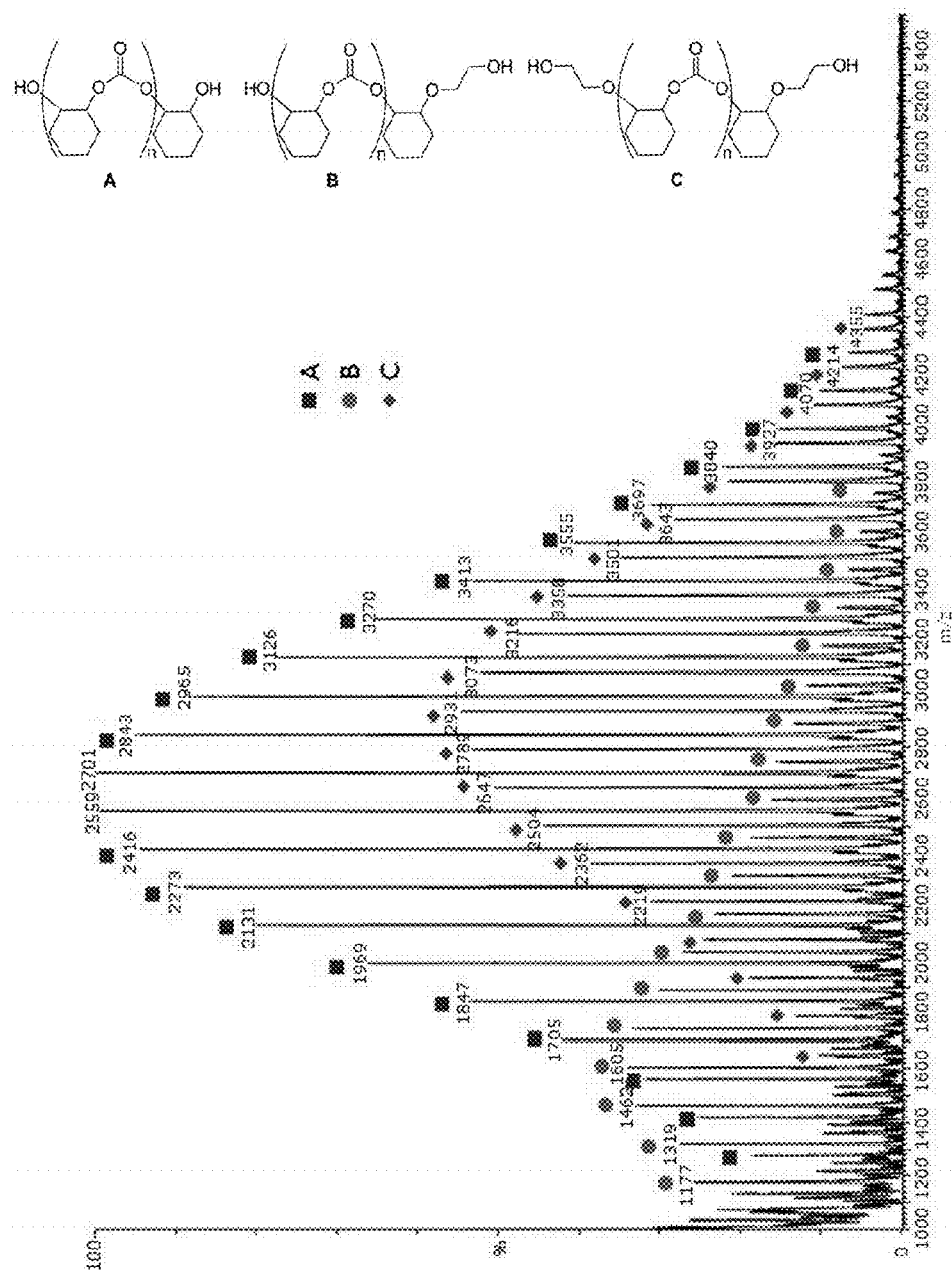
FIG. 8 shows the MALDI-TOF MS spectrum of the polycarbonate produced by $[L^1Co_2(OAc)_3]$ and 10 equivalents of ethylene glycol as CTA.

Cyclohexene oxide (5 mL, 25 mmol), [$L^1Co_2(OAc)_3$] (0.042 g, 0.049 mmol) and ethylene glycol (1-20 equivalents) were added to a Schlenk tube. The cyclohexene oxide was degassed, before being left stirring under 1 atm $CO_2$, at set temperature, for 4 hours. The crude product was taken up in $CH_2Cl_2$ and the solution was left to evaporate in air, after which the product was dried in vacuo overnight. No further purification of the polymer was undertaken as the vacuum was sufficient to remove unreacted cyclohexene oxide. FIG. 8 shows a MALDI-TOF spectra of the polycarbonate produced by the above method. It can be seen that all polymers produced by this method are terminated with hydroxyl groups at both ends of the polymer chains.

TABLE 2

Copolymerization of CHO and $CO_2$ using Complex 1, with various species added as chain transfer agents (CTA). Copolymerization conditions: neat CHO, 80° C., 24 h, 1 bar $CO_2$.

| Entry | Catalyst (mol %) | $TON^a$ (—) | $TOF^b$ ($h^{-1}$) | CHO Conversion (%) | $S_{carbonates}^c$ (%) | $S_{PCHC}^d$ (%) | $M_n^e$ (gmol$^{-1}$) | PDI $(M_w/M_n)^e$ |
|---|---|---|---|---|---|---|---|---|
| 1 | 0.1% complex [$L^1Zn_2(OAc)_2$] | 530 | 22 | 53 | 99 | 92 | 10949 5022 | 1.02 1.02 |
| 2 | 0.1% complex [$L^1Zn_2(OAc)_2$] + 0.1% CHD$^f$ | 580 | 24 | 58 | 99 | 93 | 8516 3588 | 1.04 1.09 |
| 3 | 0.1% complex [$L^1Zn_2(OAc)_2$] + 2% $H_2O$ | 610 | 25 | 61 | 99 | 93 | 3428 1280 | 1.06 1.01 |

$^a$TON = (mol$_{CHO\ converted}$) × (mol$_{complex\ 1}$)$^{-1}$.
$^b$TOF = TON per hour.
$^c S_{carbonate}$ = Percentage selectivity for carbonate linkages (PCHC + CHC), as determined from the normalized integrals in the $^1$H NMR spectra using the methylene resonances, including PCHC (δ: 4.65 ppm), ether linkages (δ: 3.45 ppm) and CHC (δ: 3.9 ppm).
$^d$Selectivity for PCHC within carbonate products/
$^e$Determined by GPC, in THF, using narrow Mn polystyrene standards, for calibration.
$^f$CHD = cyclohexane-1,2-diol.

Experimental Details for CTA Experiments with [$L^1Co_2$ $(OAc)_3$]/Ethylene Glycol and Subsequent Block Copolymerisation with (Rac/L)-Lactide Scheme 1: Copolymerisation of CHO and $CO_2$ using ethylene glycol as a chain transfer agent. i) [$L^1Co_2(OAc)_3$] (0.1 mol %), 1 atm $CO_2$, 80° C.

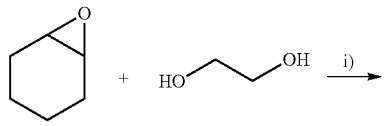

Figure 9:
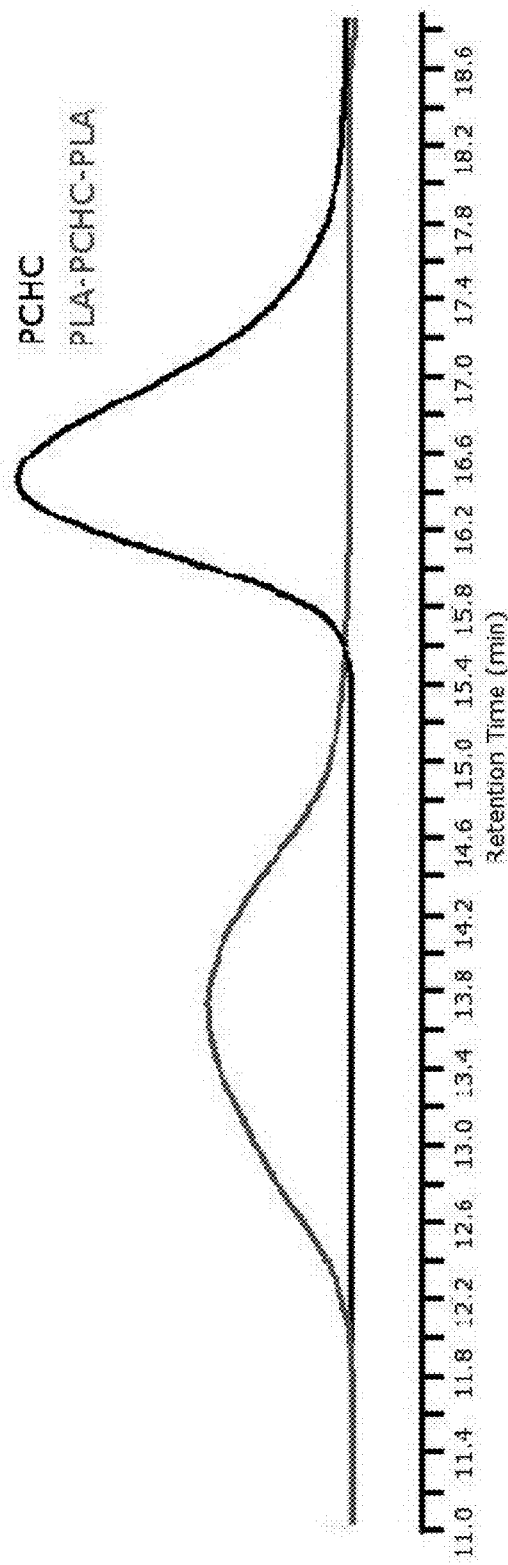
FIG. 9 shows the Overlaid GPC traces of HO—PCHC—OH from ethylene glycol ($M_n$=2000) and PLA-PCHC-PLA ($M_n$=30400)

Low Pressure Copolymerisation of CHO and $CO_2$ with [$L^1Co_2(OAc)_3$] and Ethylene Glycol Block Copolymerisation of HO—PCHC—OH with (Rac/L)-Lactide Under a nitrogen atmosphere in a glovebox, (rac/L)-lactide (0.5, 1 or 2 mmol) was placed in a vial with a stirrer bar and dissolved in THF (1.5 mL). Separately, PCHC (0.005 mmol) was placed in a vial with Y (5.4 mg, 0.1 mmol) and dissolved in THF (0.5 mL). This solution was then added to the lactide solution, and stirred for approximately 5 minutes, until the viscosity increased such that stirring could no longer continue. The reaction was terminated and the polymer precipitated by the addition of hexane (~2 mL). The polymer was filtered off and dried under vacuum. (FIG. 9)

Scheme 2: Block copolymerisation of PCHC with lactide.
1) 1 (2 equiv.), lactide (200 or 400 equiv.), THF, 25° C., 5 mins.

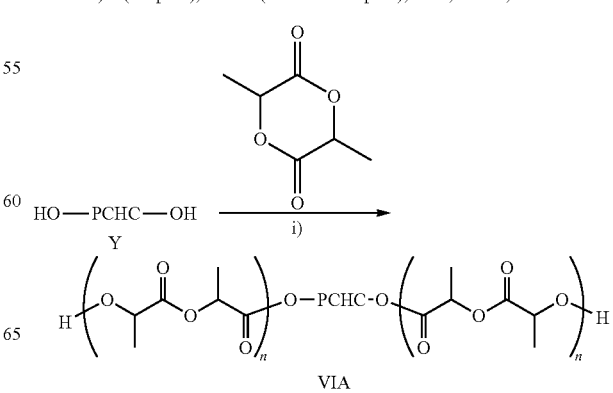

47
-continued
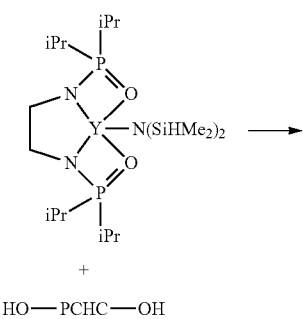
+
HO—PCHC—OH
48
-continued
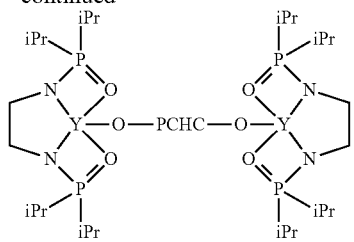
Copolymerisation of CHO with [L$^1$Zn$_2$(O$_2$CCF$_3$)$_2$] Producing HO—PCHC—OH and Subsequent Block Copolymerisation with (Rac/L)-Lactide
Scheme 3: Copolymerisation of CHO and subsequent block copolymerisation with lactide. i) [L$^1$Zn$_2$(O$_2$CCF$_3$)$_2$] (0.1 mol %), 80° C., 1 atm CO$_2$, 24 hrs. ii) Y (2 equiv.), THF, 25° C., 5 mins.
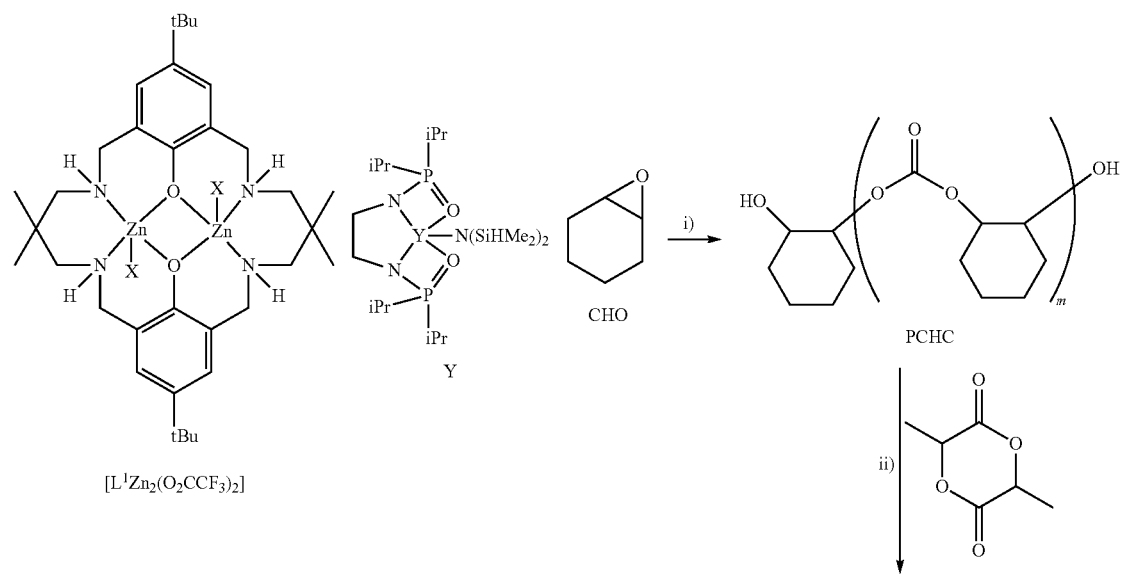
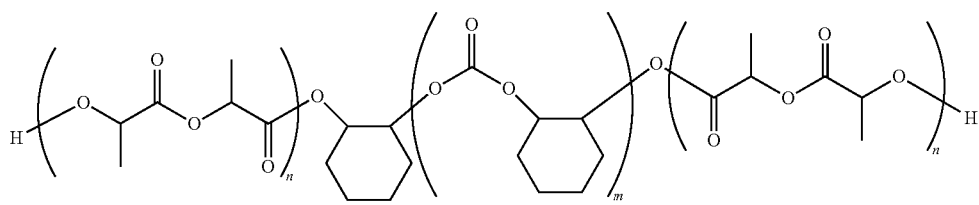
PLA-PCHC-PLA

Copolymerisation Conditions

Figure 10:
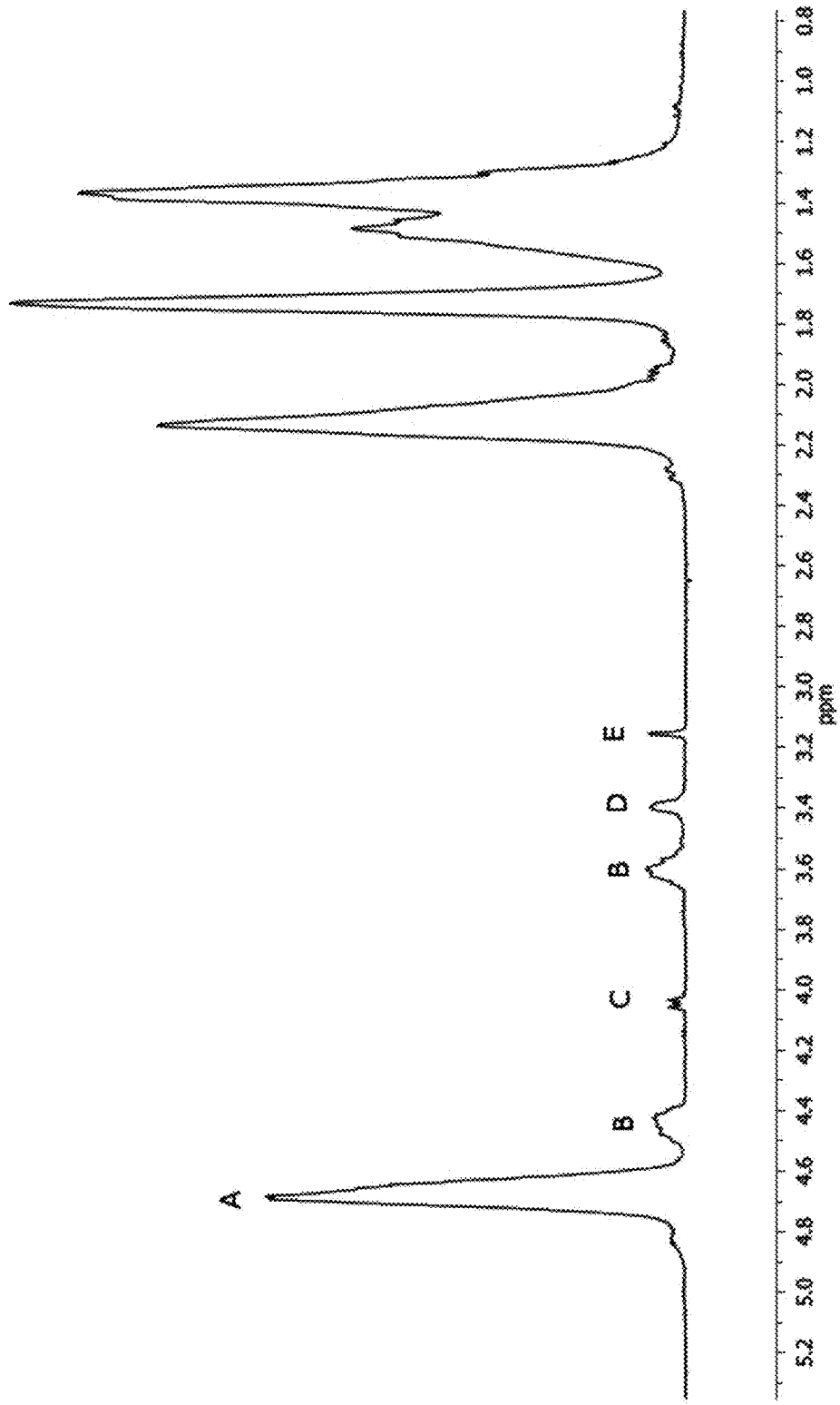
FIG. 10 shows the $^1H$ NMR spectrum of PCHC produced by $[L^1Zn_2(O_2CCF_3)_2]$. Peak A assigned to methyne protons of polycarbonate linkages. Peaks B are assigned to the methyne protons of the terminal hydroxyl end group. Peak C is assigned to the cyclic carbonate by-product CHC. Peak D is assigned to the methyne protons of ether linkages. Peak E is assigned to unreacted CHO.
Figure 11:
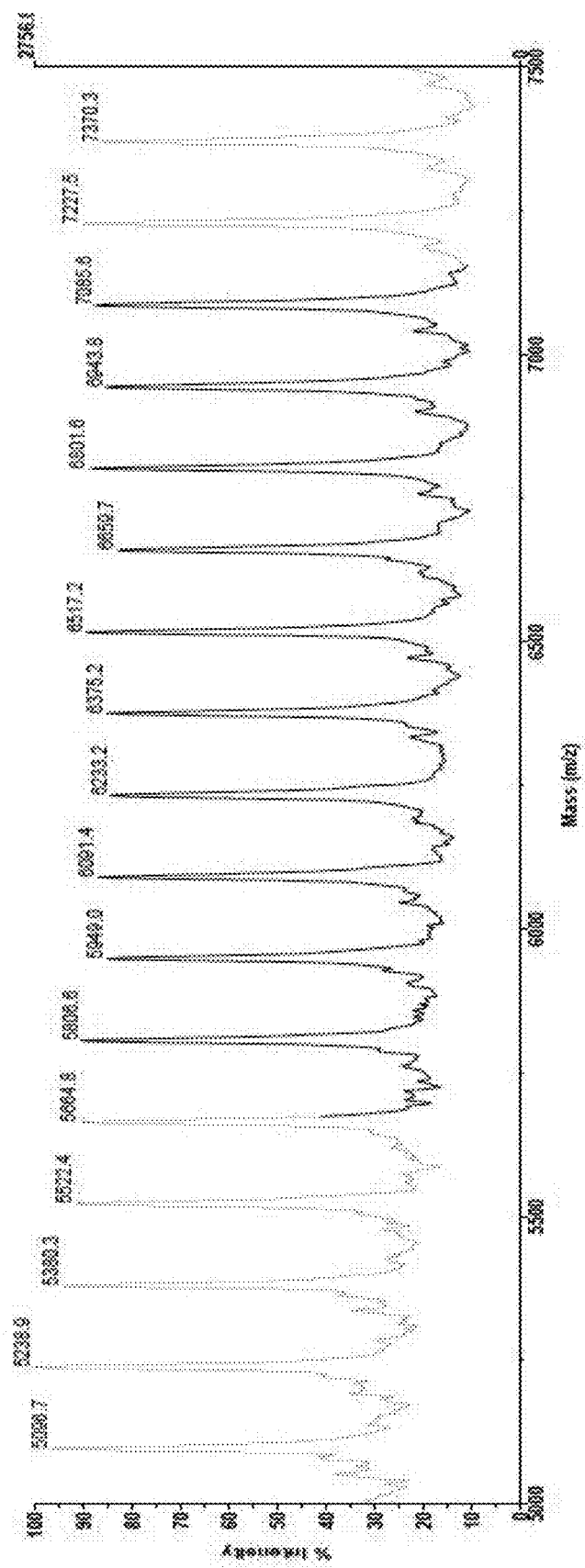
FIG. 11 shows the MALDI-TOF MS spectrum of PCHC produced by $[L^1Zn_2(O_2CCF_3)_2]$, showing the polymer series $[HO(C_7H_{10}O_3)_1C_6H_{11}O_2]Li^+$. [17.01+(142.15)n+99.15+6.9].
Figure 12:
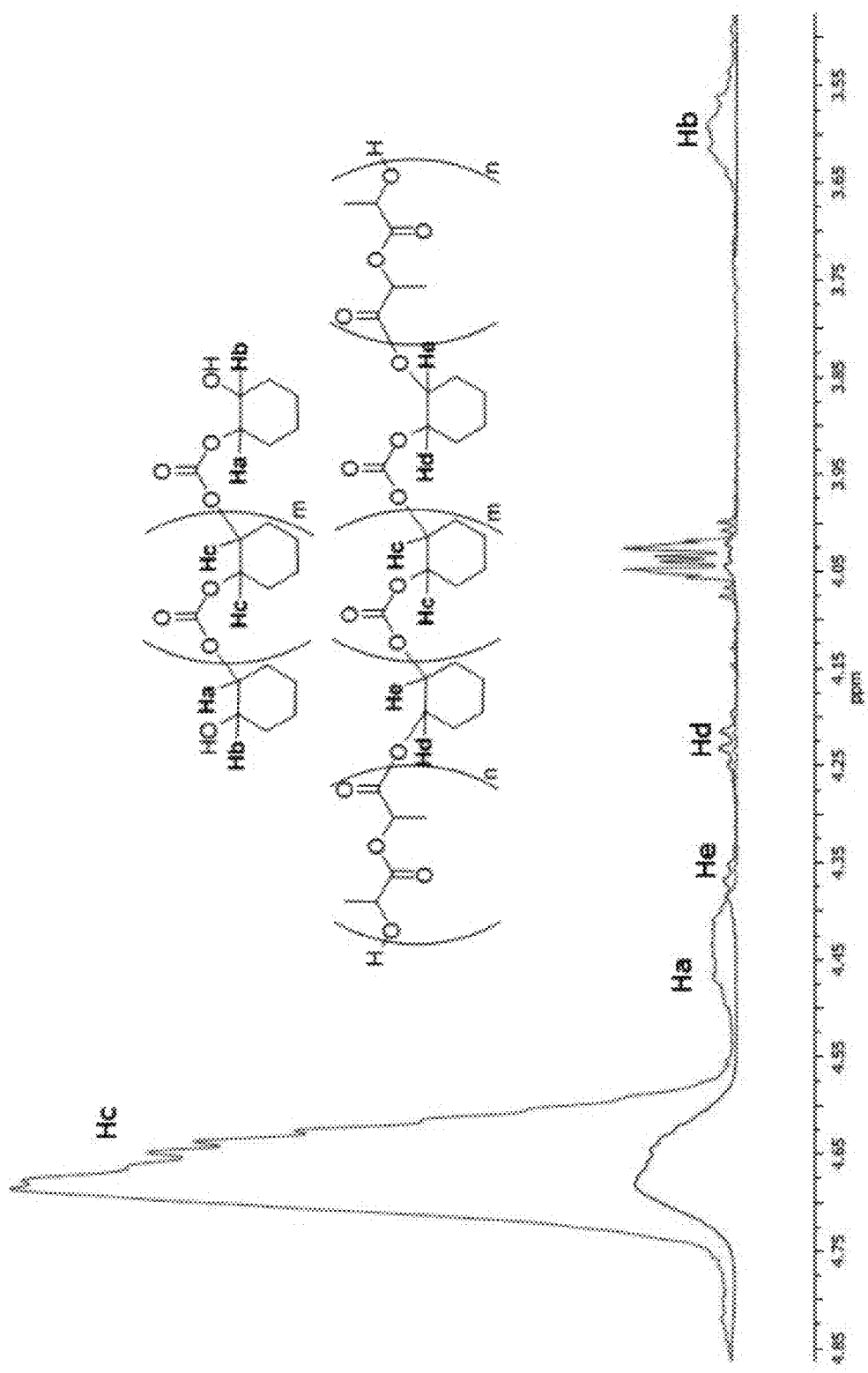
FIG. 12 shows the overlaid $^1H$ NMR spectrum of PCHC (blue) and PLA-PCHC-PLA (red), showing terminal and linkage methyne cyclohexane protons
Figure 13:
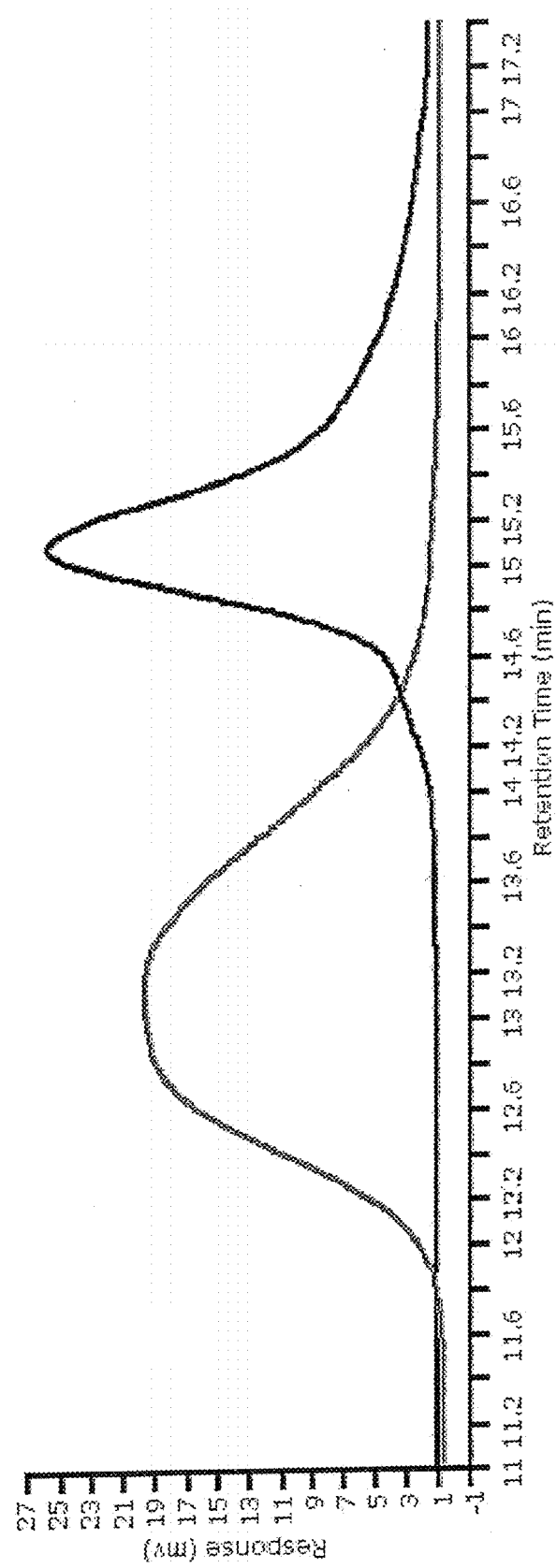
FIG. 13 shows the overlaid GPC traces of PCHC ($M_n$=9100) and PLA-PCHC-PLA ($M_n$=51000) vs narrow polystyrene standards in THF.
Figure 14:
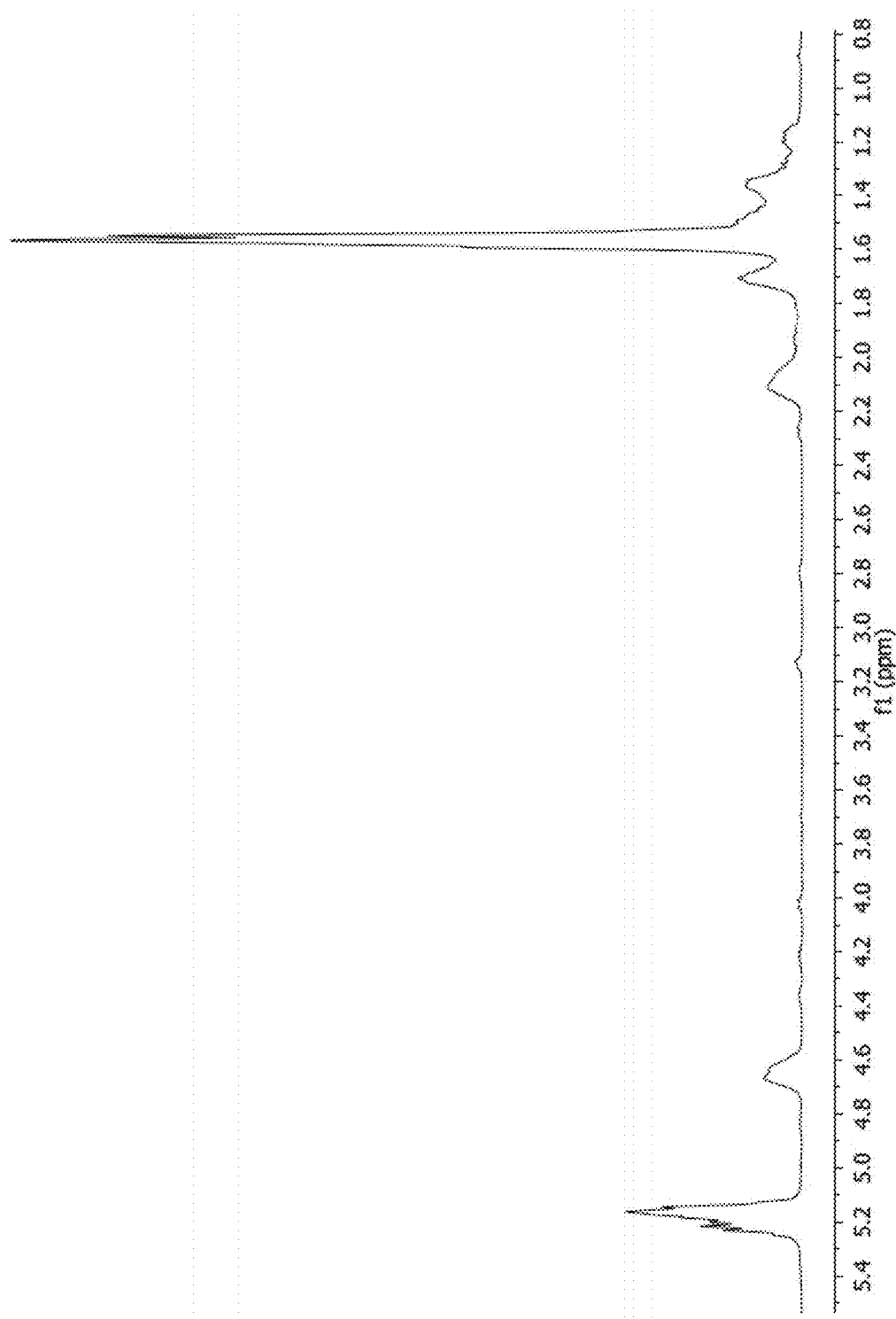
FIG. 14 shows the $^1H$ NMR spectrum of precipitated PLA-PCHC-PLA (PCHC Mn=9000, 400 equiv. PLA, PLA-PCHC-PLA Mn=51000).

Cyclohexene oxide (2.5 mL, 25 mmol) and [L¹Zn₂(F₃CCOO)₂] (0.022 g, 0.025 mmol) were added to a Schlenk tube. The vessel was evacuated, and charged with 1 atm $CO_2$ after which it was left stirring at 80° C. for 24 hours. The crude reaction mixture was then taken up in $CH_2Cl_2$ (10 mL) and evaporated in air. The product was then dried in vacuo overnight. This proved sufficient to remove unreacted monomer, no further purification was necessary. (FIGS. 10 and 11)

Block Copolymerization Conditions

Under a nitrogen atmosphere in a glovebox, (rac/L)-Lactide ( ) was placed in a vial with a stirrer bar and dissolved in THF (1.5 mL). Separately, Poly(cyclohexene carbonate) (0.05 mmol) was placed in a vial with Y (5.4 mg, 0.1 mmol) and dissolved in THF (0.5 mL). This solution was then added to the lactide solution, and stirred for approximately 5 minutes, until the viscosity increased such that stirring could no longer continue. The reaction was terminated and the polymer precipitated by the addition of hexane (~2 mL). The polymer was filtered off and dried under vacuum. (FIG. 11)

TABLE 3

Block copolymerisation of PCHC and PLA

| $M_n$ PCHC[a] GPC | Mn PCHC NMR[b] | Lactide per chain end | $M_n$[a] (GPC) | PDI[a] | $M_n$[c] (NMR) | $M_n$[d] (Predicted) |
|---|---|---|---|---|---|---|
| 9000 | 6000 | 200(rac) | 51000 | 1.30 | 54400 | 64300 |
| 9000 | 6000 | 100(rac) | 23500 | 1.33 | 23100 | 36800 |
| 9000 | 6000 | 50(rac) | 17300 | 1.34 | 14800 | 22500 |
| 9000 | 6000 | 50(L) | 20100 | 1.38 | 15300 | 22600 |
| 6000 | 4000 | 100(rac) | 37700 | 1.28 | 28700 | 34000 |
| 2500 | 2600 | 100(rac) | 44900 | 1.30 | 20600 | 29500 |
| 2500 | 2600 | 100(L) | 40800 | 1.37 | 19700 | 30300 |

[a]Determined by Gel permeation chromatography using THF as an eluent, agains narrow polystyrene standards.
[b]Determined by relative integrals of Hb and Hc in ¹H NMR spectrum
[c]Determined by relative integrals of PCHC proton Hd vs PCHC carbonate protons Hc vs lactide plus known weight of PCHC.
[d]Determined by relative integrals of PLA and unreacted lactide in ¹H NMR spectrum.

Example 3

Copolymerisation of Carbon Dioxide and Cyclohexene Oxide (CHO) in the Presence of Various Chain Transfer Agents (CTAs)

Zinc catalysts 1 ([L¹Zn₂(OAc)₂]) and 2 ([L¹Zn₂(CF₃COO)₂]) were used, in a 0.1 mol % stoichiometry, to copolymerise cyclohexene oxide (CHO) and carbon dioxide, with the addition of 0.4 mol % chain transfer agents A through Q or water, to produce polycyclohexene oxide carbonate polyols and diols.

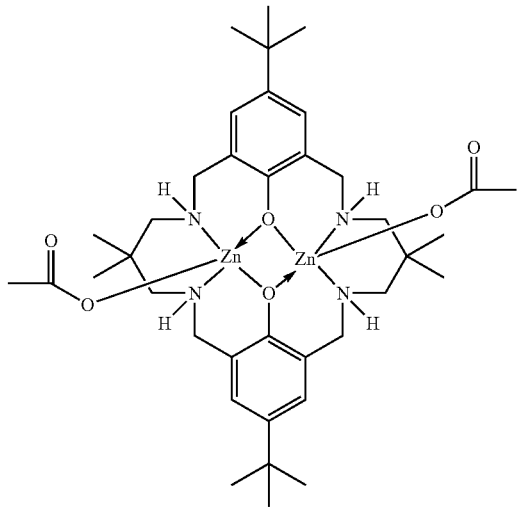

1: [L¹Zn₂(OAc)₂]

1: [L¹Zn₂(CF₃COO)₂]

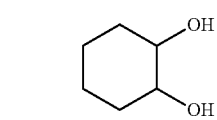

A

Cyclohexenediol
Chemical Formula: $C_6H_{12}O_2$
Molecular Weight: 116.16

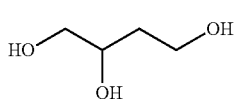

B 1,2,4-butanetriol
Chemical Formula: $C_4H_{10}O_3$
Molecular Weight: 106.12

-continued

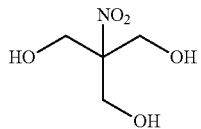

tris(methylalcohol)nitropropane
Chemical Formula: C$_4$H$_9$NO$_5$
Molecular Weight: 151.12

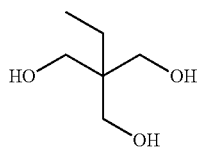

tris(methylalcohol)propane
Chemical Formula: C$_6$H$_{14}$O$_3$
Molecular Weight: 134.17

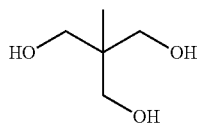

tris(methylalcohol)ethane
Chemical Formula: C$_5$H$_{12}$O$_3$
Molecular Weight: 120.15

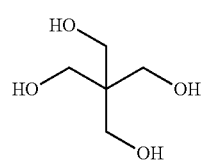

2,2-bis(methylalcohol)-1,3-propanediol
Chemical Formula: C$_5$H$_{12}$O$_4$
Molecular Weight: 136.15

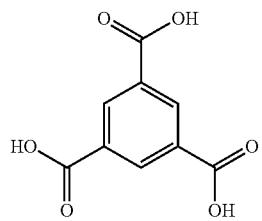

1,3,5-benzenetricarboxylic acid
Chemical Formula: C$_9$H$_6$O$_6$
Molecular Weight: 210.14

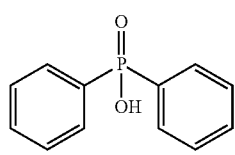

Diphenylphosphinic acid
Chemical Formula: C$_{12}$H$_{11}$OP
Molecular Weight: 202.19

-continued

C

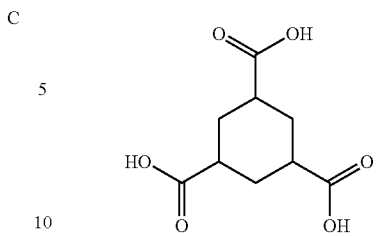

D 1,3,5-cyclohexanetricarboxylic acid
Chemical Formula: C$_9$H$_{12}$O$_6$
Molecular Weight: 216.19

E

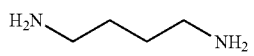

1,4-butanediamine
Chemical Formula: C$_4$H$_{12}$N$_2$
Molecular Weight: 88.15

F

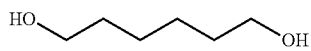

1,6-hexanediol
Chemical Formula: C$_6$H$_{14}$O$_2$
Molecular Weight: 118.17

G

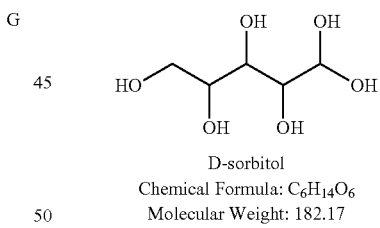

D-sorbitol
Chemical Formula: C$_6$H$_{14}$O$_6$
Molecular Weight: 182.17

H

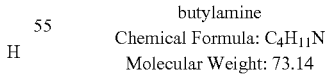

butylamine
Chemical Formula: C$_4$H$_{11}$N
Molecular Weight: 73.14

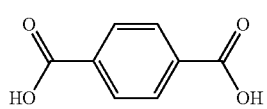

terephthalic acid
Chemical Formula: C$_8$H$_6$O$_4$
Molecular Weight: 166.13

-continued

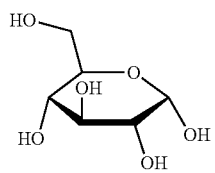

D-(+)-glucose
Chemical Formula: $C_6H_{12}O_6$
Molecular Weight: 180.16

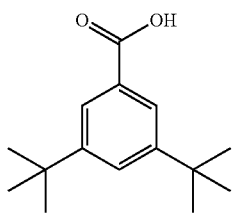

3,5-di-tert-butylbenzoic acid
Chemical Formula: $C_{15}H_{22}O_2$
Molecular Weight: 234.33

-continued

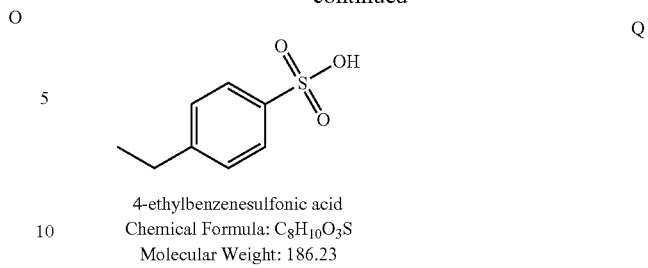

4-ethylbenzenesulfonic acid
Chemical Formula: $C_8H_{10}O_3S$
Molecular Weight: 186.23

P

Each of the reactions was carried out using the following reaction conditions: 0.1 mol % catalyst loading, 80° C., 700 rpm stirring speed, 0.4 mol % chain transfer agent (CTA), 5 ml CHO.

Tables 4 and 5 show the catalyst activities and percentage conversions for each reaction.

TABLE 4

Zinc catalyst 1 ($[L^1Zn_2(OAc)_2]$)

| CTA | Time (h) | Polymer % | Cyclic % | total conv % | TON | TON (gPOLY/gCAT) | TOF | TOF (from gPOLY/gCAT) | Polymer vs. cyclic % |
|---|---|---|---|---|---|---|---|---|---|
| A | 15 | 49.5 | 1.3 | 50.8 | 508 | 90 | 33.9 | 6.0 | 97.4 |
| B | 15 | 45.4 | 0.1 | 45.5 | 455 | 81 | 30.3 | 5.4 | 99.8 |
| C | 15 | 1.6 | 0.4 | 2 | 20 | 4 | 1.3 | 0.2 | 80.0 |
| D | 15 | 37.1 | 1.1 | 38.2 | 382 | 68 | 25.5 | 4.5 | 97.1 |
| E | 15 | 42.3 | 1.3 | 43.6 | 436 | 78 | 29.1 | 5.2 | 97.0 |
| F | 15 | 27.4 | 1.5 | 28.9 | 289 | 51 | 19.3 | 3.4 | 94.8 |
| G | 16 | 23.3 | 0.2 | 23.5 | 235 | 42 | 14.7 | 2.6 | 99.1 |
| H | 17.5 | 50 | 3.2 | 53.2 | 532 | 95 | 30.4 | 5.4 | 94.0 |
| I | 17.5 | 51.4 | 3.8 | 55.2 | 552 | 98 | 31.5 | 5.6 | 93.1 |
| J | 17.5 | 47.5 | 3.5 | 51 | 510 | 91 | 29.1 | 5.2 | 93.1 |
| K | 17.5 | 49.6 | 2.4 | 52 | 520 | 92 | 29.7 | 5.3 | 95.4 |
| L | 16 | 9.2 | 1 | 10.2 | 102 | 18 | 6.4 | 1.1 | 90.2 |
| M | 16 | 55.2 | 2.2 | 57.4 | 574 | 102 | 35.9 | 6.4 | 96.2 |
| N | 16 | 49.3 | 1.3 | 50.6 | 506 | 90 | 31.6 | 5.6 | 97.4 |
| O | 16 | 6.6 | 0.3 | 6.9 | 69 | 12 | 4.3 | 0.8 | 95.7 |
| P | 16 | 52.7 | 1.6 | 54.3 | 543 | 97 | 33.9 | 6.0 | 97.1 |
| Q | 16 | 18.2 | 0.3 | 18.5 | 185 | 33 | 11.6 | 2.1 | 98.4 |
| Water | 24 | 53.7 | 1.1 | 54.8 | 548 | 97 | 22.8 | 4.1 | 98.0 |

TABLE 5

Zinc catalyst 2 ($[L^1Zn_2(CF_3COO)_2]$)

| CTA | Time (h) | Polymer % | Cyclic % | total conv % | TON | TON (gPOLY/gCAT) | TOF | TOF (from gPOLY/gCAT) | Polymer vs. cyclic % |
|---|---|---|---|---|---|---|---|---|---|
| A | 15 | 24 | 0.3 | 24.3 | 243 | 38 | 16.2 | 2.5 | 98.8 |
| B | 15 | 27.3 | 0.5 | 27.8 | 278 | 44 | 18.5 | 2.9 | 98.2 |
| D | 15 | 30 | 1.5 | 31.5 | 315 | 49 | 21.0 | 3.3 | 95.2 |
| E | 15 | 33.7 | 1.7 | 35.4 | 354 | 55 | 23.6 | 3.7 | 95.2 |
| F | 15 | 17.7 | 1.5 | 19.2 | 192 | 30 | 12.8 | 2.0 | 92.2 |
| G | 16 | 26.3 | 0.3 | 26.6 | 266 | 42 | 16.6 | 2.6 | 98.9 |
| H | 16 | 49.5 | 0.8 | 50.3 | 503 | 79 | 31.4 | 4.9 | 98.4 |
| I | 16 | 32.8 | 0.5 | 33.3 | 333 | 52 | 20.8 | 3.3 | 98.5 |
| J | 16 | 50.1 | 1.7 | 51.8 | 518 | 81 | 32.4 | 5.1 | 96.7 |
| L | 16 | 57.9 | 2 | 59.9 | 599 | 94 | 37.4 | 5.9 | 96.7 |
| M | 16 | 48.2 | 1.2 | 49.4 | 494 | 77 | 30.9 | 4.8 | 97.6 |
| N | 16 | 42.3 | 0.9 | 43.2 | 432 | 68 | 27.0 | 4.2 | 97.6 |

TABLE 5-continued

| | | | | total | | TON | | TOF (from | Polymer |
| | Time | Polymer | Cyclic | conv | | (gPOLY/ | | gPOLY/ | vs. |
| CTA | (h) | % | % | % | TON | gCAT) | TOF | gCAT) | cyclic % |
| --- | --- | --- | --- | --- | --- | --- | --- | --- | --- |
| | | | | Zinc catalyst 2 ([L$^1$Zn$_2$(CF$_3$COO)$_2$]) | | | | | |
| O | 16 | 15.1 | 1 | 16.1 | 161 | 25 | 10.1 | 1.6 | 93.8 |
| P | 16 | 47.1 | 0.7 | 47.8 | 478 | 75 | 29.9 | 4.7 | 98.5 |
| Q | 16 | 8.7 | 0.7 | 9.4 | 94 | 15 | 5.9 | 0.9 | 92.6 |
| Water | 20 | 43.1 | 0.5 | 43.6 | 436 | 68 | 21.8 | 3.4 | 98.9 |

The above results show that the catalysts of the invention are compatible with a wide range of chain transfer agents.

In a further set of experiments, zinc catalysts 1 ([L$^1$Zn$_2$(OAc)$_2$]) and 2 ([L$^1$Zn$_2$(CF$_3$COO)$_2$]) were used, in a 0.1 mol % stoichiometry, to copolymerise cyclohexene oxide (CHO) and carbon dioxide, with the addition of 0.1 mol % to 10 mol % water as a chain transfer agent, to produce polycyclohexene oxide carbonate diols.

Tables 6 and 7 show the catalyst activities and percentage conversions for each reaction.

TABLE 6

Zinc catalyst 1 ([L$^1$Zn$_2$(OAc)$_2$])

| H2O eq. | Time (h) | Polymer % | Cyclic % | total conv % | TON | TON (gPOLY/ gCAT) | TOF | TOF (from gPOLY/ gCAT) | Polymer vs. cyclic % |
| --- | --- | --- | --- | --- | --- | --- | --- | --- | --- |
| 0 | 24 | 63 | 3.2 | 66.2 | 662 | 118 | 27.6 | 4.9 | 95.2 |
| 1 | 24 | 51.8 | 1.3 | 53.1 | 531 | 94 | 22.1 | 3.9 | 97.6 |
| 2 | 24 | 50 | 3.7 | 53.7 | 537 | 95 | 22.4 | 4.0 | 93.1 |
| 4 | 24 | 53.7 | 1.1 | 54.8 | 548 | 97 | 22.8 | 4.1 | 98.0 |
| 8 | 24 | 48.1 | 0.6 | 48.7 | 487 | 87 | 20.3 | 3.6 | 98.8 |
| 16 | 24 | 42.8 | 0.6 | 43.4 | 434 | 77 | 18.1 | 3.2 | 98.6 |
| 32 | 24 | 14 | 0.5 | 14.5 | 145 | 26 | 6.0 | 1.1 | 96.6 |
| 64 | 48 | 0.3 | 0 | 0.3 | 3 | 1 | 0.1 | 0.0 | 100.0 |

TABLE 7

Zinc catalyst 2 ([L$^1$Zn$_2$(CF$_3$COO)$_2$])

| H2O eq. | Time (h) | Polymer % | Cyclic % | total conv % | TON | TON (gPOLY/ gCAT) | TOF | TOF (from gPOLY/ gCAT) | Polymer vs. cyclic % |
| --- | --- | --- | --- | --- | --- | --- | --- | --- | --- |
| 0 | 22 | 51.3 | 0.8 | 52.1 | 521 | 8125 | 23.7 | 369 | 98.5 |
| 1 | 20 | 43 | 0.4 | 43.4 | 434 | 6768 | 21.7 | 338 | 99.1 |
| 2 | 20 | 45 | 0.5 | 45.5 | 455 | 7095 | 22.8 | 355 | 98.9 |
| 4 | 20 | 43.1 | 0.5 | 43.6 | 436 | 6799 | 21.8 | 340 | 98.9 |
| 8 | 20 | 47 | 1 | 48 | 480 | 7485 | 24.0 | 374 | 97.9 |
| 16 | 20 | 42.8 | 1 | 43.8 | 438 | 6830 | 21.9 | 342 | 97.7 |
| 32 | 20 | 19.8 | 0.8 | 20.6 | 206 | 3212 | 10.3 | 161 | 96.1 |
| 64 | 20 | 9.8 | 1.2 | 11 | 110 | 1715 | 5.5 | 86 | 89.1 |
| 128 | 23 | 0.9 | 0.2 | 1.1 | 11 | 172 | 0.5 | 7 | 81.8 |

Example 4

Copolymerisation of Carbon Dioxide and Cyclohexene Oxide (CHO) in the Presence of Water as a Chain Transfer Agent Three magnesium catalysts 2a, 2b and 2c were used to copolymerise CHO and carbon dioxide both with and without exogenous water as a chain transfer agent.

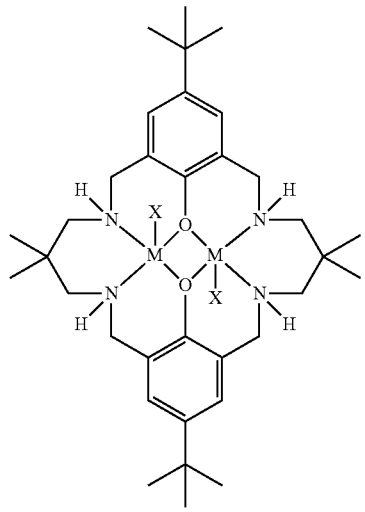

2a M = Mg, X = OAc
2b M = Mg, X = Br
2c M = Mg, X = $O_2CCF_3$

Catalysts 2a and 2b were prepared by deprotonation of the macrocyclic ligand $H_2L^1$, using KH, followed by a salt metathesis reaction with two equivalents of the appropriate Mg precursor ($Mg(OAc)_2$, $MgBr_2$. Catalyst 2c was prepared by reacting 2b with 2 equivalents of $K(O_2CCF_3)$ in THF at room temperature.

Each reaction was carried out in neat CHO at 1 atm $CO_2$ pressure and 1:1000 catalyst loading for 3-18 hours. Table 8 shows the results of the polymerisation reactions.

TABLE 8 copolymerisation data for catalysts 2a-2c

| Cat | T (° C.) | Cat: $H_2O$ | TON[b] | TOF[c] | $M_n$[d] | PDI |
|---|---|---|---|---|---|---|
| 2a | 80 | 1:0 | 522 | 35 | 13,300/6800 | 1.03/1.05 |
| 2b | 80 | 1:0 | 426 | 24 | 5500 | 1.21 |
| 2c | 80 | 1:0 | 497 | 31 | 6500 | 1.21 |
| 2c[a] | 100 | 1:0 | 3000 | 750 | 24,500/5300 | 1.03/1.10 |
| 2c | 100 | 1:10 | 360 | 103 | 3600 | 1.16 |
| 2c | 100 | 1:30 | 350 | 80 | 1700 | 1.12 |

[a] copolymerisation run at 12 atm $CO_2$ and 1:10000 loading;
[b] mole CHO consumed/mole cat.;
[c] TON/time (h);
[d] by size exclusion chromatography (SEC) in gmol$^{-1}$.

The copolymers formed with 2c were analyzed by MALDI-ToF mass spectrometry (not shown) and SEC (FIG. 15), which showed terminal groups from both chain transfer and initiation reactions (Y=OH and $O_2CCF_3$; respectively). In the case of 2c, a significant reduction in the HO—PCHC—$O_2CCF_3$, i.e. mono-hydroxyl peak was observed by SEC analysis compared the copolymer produced by 2a (see FIG. 15). This indicated that 2c might show enhanced selectivity for polyol formation. In order promote selective polyol formation, the copolymerization was run using water, 10 and 30 equivalents versus 2c, as a chain transfer agent. These experiments show that water is an effective chain transfer agent, reducing molecular weight and producing narrower weight distributions.

Figure 15:
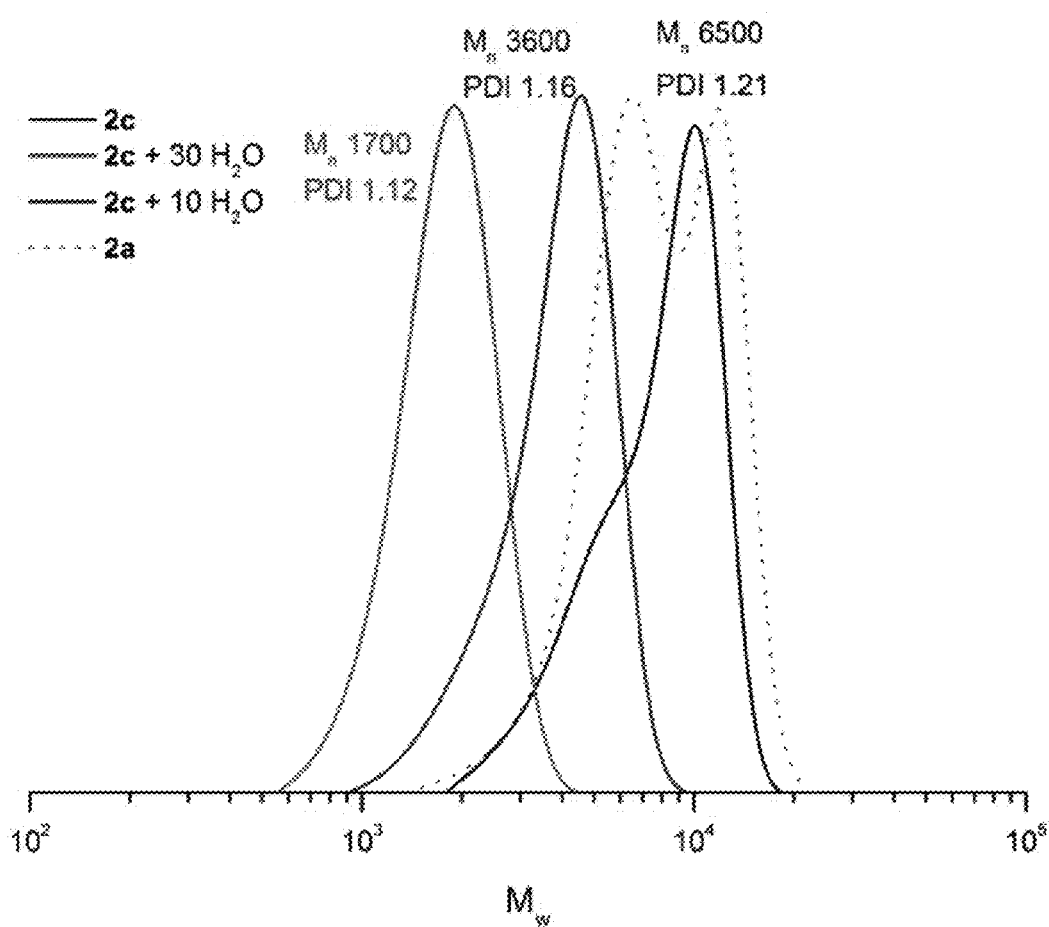
FIG. 15 shows the distributions of molecular weights, determined using SEC, for PCHC produced by catalysts $[L^1Mg_2(OAc)_2]$ and $[L^1Mg_2(OCOCF_3)_2]$ (catalysts 2a and 2c, respectively) in the presence of water.

Almost complete suppression of trifluoroacetate end groups was observed when 30 equivalents of water were added (FIG. 15). By analysing the $^1$H NMR spectrum of the copolymer, it was estimated that 2c produces approximately 50% polyol in the absence of additional water. Upon addition of 30 equivalents of water, the selectivity for polyol increases to 85%. Even using excess water, 2c still shows good catalytic activity (c.f. 2a under same conditions without water, table 8, entry 4).

Furthermore, even in the presence of excess water, 2c maintains a high selectivity for copolymer formation (>99% carbonate linkages, >99% selectivity for copolymer by $^1$H NMR). This is particularly remarkable as other catalysts which are used to copolymerize $CO_2$ and epoxides are deactivated by water, leading to complete suppression of catalytic activity (Seong, J. E. et al; Macromolecules 2010, 43, 903-908; Lu, X.-B.; Darensbourg, D. J. Chem. Soc. Rev. 2012, 41, 1462-1484; Na, S. J et al; Inorg. Chem. 2009, 48, 10455-10465). Such high tolerance to excess water is especially relevant for the integration of this process with carbon capture because water is a common contaminant of captured carbon dioxide, including typical concentrations of 2% in carbon dioxide captured from flue gases from coal combustion.

Example 5

Copolymerisation of Cyclohexene Oxide and $CO_2$ in the Presence of Various Catalysts The activity of novel catalysts [$L^1Zn_2$(hexanoate)$_2$], [$L^1Zn_2$(octanoate)$_2$] and [$L^1Zn_2$(dodecanoate)$_2$] were tested and compared to catalyst [$L^1Zn_2$(OAc)$_2$].

Each of the reactions were carried out at 80° C., 1 atm $CO_2$ and 0.1% catalyst loading. The results of these tests are set out in table 9.

TABLE 9 activity of novel catalysts and catalyst [L¹Zn₂(OAc)2].

| Catalyst | Time (hrs) | TON | TOF (h⁻¹) | % copolymer | % conversion | $M_n$ (g/mol) | PDI |
|---|---|---|---|---|---|---|---|
| L¹Zn₂(OAc)₂ | 24 | 439 | 18 | 99 | 45 | 6200 | 1.19 |
| L¹Zn₂(hexanoate)₂ | 23 | 557 | 24 | 98 | 56 | 4205 | 1.13 |
| L¹Zn₂(octanoate)₂ | 23.5 | 466 | 20 | 99 | 47 | 4683 | 1.14 |
| L¹Zn₂(dodecanoate)₂ | 22 | 548 | 25 | 98 | 55 | 5746 | 1.13/1.01 |

Example 6

Copolymerisation of Cyclohexene Oxide and $CO_2$ in the Presence of Various Catalysts The activity of novel catalysts having the formula [L¹Zn₂X₂] was tested and the results of these tests are set out in table 10 below.

TABLE 10 activity of novel catalysts

| Entry | X group | Time (h) | TON | TOF (h⁻¹) | Mn (g/mol) | PDI |
|---|---|---|---|---|---|---|
| 1 | benzoate | 18 | 450 | 25 | 5256 | 1.13 |
| 2 | pentafluorobenzoate | 18 | 428 | 23.7 | 4502 | 1.09 |
| 3 | pivalate | 18 | 569 | 31.6 | 5058 | 1.12 |
| 5 | Adamantyl carboxylate | 18 | 554 | 30.7 | 4997 | 1.12 |
| 6 | Diphenyl phosphinate (OP(O)Ph₂ | 18 | 490 | 27.2 | 4362 | 1.11 |
| 7 | Bis(4-methoxy)phenyl-phosphinate (OP(O)(OMeC₆H₄)₂ | 18 | 527 | 29 | 4091 | 1.12 |

Example 7

Synthesis of L⁴Mg₂(OAc)₂

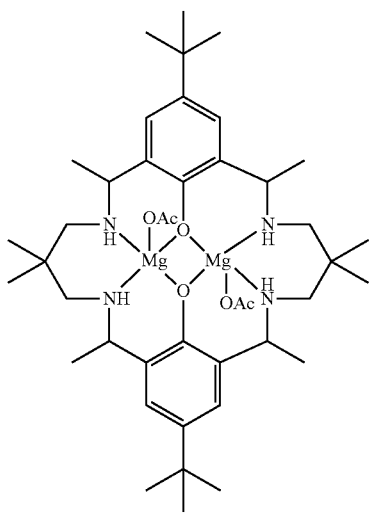

[L⁴Mg₂(OAc)₂]

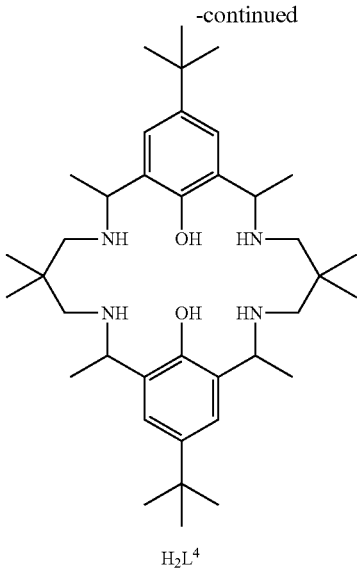

H₂L⁴

The synthesis of 2,6-diacetyl-4-tert-butylphenol was carried out using a literature procedure (Aromi et al, Synth. Comm. 2003, 33, 11-18.). The synthesis of L⁴ was carried out using the procedure described in WO2009/130470 for the synthesis of L¹, in 66% overall yield, by replacing 2,6-diformyl-4-tert-butylphenol with 2,6-diacetyl-4-tert-butylphenol.

L⁴: Anal. Calc. for $C_{38}H_{64}N_4O_2$: C, 74.95; H, 10.59; N, 9.20. Found: C, 74.84; H, 10.54; N, 9.27. ¹H NMR (400 MHz, $CDCl_3$) δ: 7.10-6.80 (m, 4H, Ar—H), 4.10-3.70 (m, 4H, N—H), 2.60-2.10 (m, 8H, C—CH₂—N), 1.50-1.40 (m, 12H), 1.30 (m, 18H), 1.10-0.90 (m, 12H). m/z (ESI)=609 (100%, [M+H]⁺).

H₂L⁴ (0.12 g, 0.20 mmol) was dissolved in THF (10 mL) and transferred into a Schlenk tube containing KH (0.020 g, 0.49 mmol) and cooled to −78° C., under nitrogen. The suspension was allowed to warm to room temperature and left to stir for 1 hour. Any excess KH was filtered off, after which MgOAc₂ (0.056 g, 0.39 mmol) was added, slowly. The reaction was stirred for 16 hours, before the solution was filtered by centrifugation and the solvent removed in vacuo.

L⁴Mg₂(OAc)₂: Anal. Calc. for $C_{42}H_{68}Mg_2N_4O_6$: C, 65.21; H, 8.86; N, 7.24. Found: C, 65.11; H, 8.70; N, 7.18. ¹H NMR (400 MHz, d₂-TCE, 373K) δ: 7.05-6.70 (br m, 4H), 4.40-1.80 (br m, 14H), 1.60-0.80 (br m, 42H). m/z (LSIMS)=713.5 (100%, [M OAc]⁺).

The invention claimed is:
1. A process for the synthesis of a polycarbonate, the process comprising the step of reacting carbon dioxide with at least one epoxide in the presence of a catalyst of formula (I):

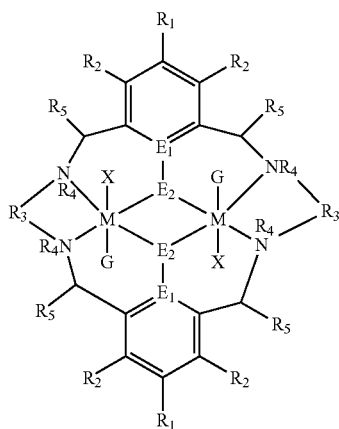

wherein:
- $R_1$ and $R_2$ are independently hydrogen, halide, a nitro group, a nitrile group, an imine, an amine, an ether group, a silyl ether group, or an acetylide group or an optionally substituted alkyl, alkenyl, alkynyl, haloalkyl, aryl, heteroaryl, alicyclic or heteroalicyclic group;
- $R_3$ is independently optionally substituted alkylene, alkenylene, alkynylene, heteroalkylene, heteroalkenylene, heteroalkynylene, arylene, heteroarylene or cycloalkylene, wherein alkylene, alkenylene, alkynylene, heteroalkylene, heteroalkenylene and heteroalkynylene, may optionally be interrupted by aryl, heteroaryl, alicyclic or heteroalicyclic;
- $R_4$ is independently H, or optionally substituted aliphatic, heteroaliphatic, alicyclic, heteroalicyclic, aryl, heteroaryl, alkylheteroaryl or alkylaryl;
- $R_5$ is H, or optionally substituted aliphatic, heteroaliphatic, alicyclic, heteroalicyclic, aryl, heteroaryl, alkylheteroaryl or alkylaryl;
- $E_1$ is C and $E_2$ is O, S or NH; or $E_1$ is N and $E_2$ is O;
- X is independently $OC(O)R^x$, $OSO_2R^x$, $OSOR^x$, $OSO(R^x)_2$, $OR^x$, phosphinate, halide, nitrate, hydroxyl, carbonate, amido or optionally substituted aliphatic, heteroaliphatic, alicyclic, heteroalicyclic, aryl or heteroaryl;
- $R_x$ is independently hydrogen, or optionally substituted aliphatic, haloaliphatic, heteroaliphatic, alicyclic, heteroalicyclic, aryl, alkylaryl or heteroaryl;
- G is absent or independently a neutral or anionic donor ligand which is a Lewis base; and
- M is independently Zn(II), Cr(II), Co(II), Mn(II), Ti(II), Mg(II), Fe(II), Cr(III)-X, Co(III)-X, Mn(III)-X, Fe(III)-X, Ca(II), Ge(II), Al(III)-X, Ti(III)-X, V(III)-X, Ge(IV)-(X)$_2$ or Ti(IV)-(X)$_2$;

and a chain transfer agent, wherein the chain transfer agent is water or a compound of formula (II):

  (II)

wherein:
- Z is an optionally substituted moiety selected from the group consisting of aliphatic, heteroaliphatic, alicyclic, heteroalicyclic, aryl, heteroaryl, polyolefin, polyester, polyether, polycarbonate and combinations thereof;
- each W is independently a hydroxyl, amine, thiol or carboxylic acid; and
- n is an integer which is at least 1;
- wherein the chain transfer agent is present in a molar ratio of at least 1:1 relative to the catalyst of formula (I).

2. The process of claim 1, wherein G is independently an optionally substituted heteroaliphatic group, an optionally substituted heteroalicyclic group, an optionally substituted heteroaryl group, a halide, hydroxide, hydride, a carboxylate, an ether, a thioether, carbene, a phosphine, a phosphine oxide, an amine, an acetamide, acetonitrile, an ester, a sulfoxide, a sulfonate or water.

3. The process of claim 1, wherein the chain transfer agent is water, a mono-alcohol, a diol, a triol, a tetraol, a polyol, a mono-amine, a polyamine, a mono-thiol, a polythiol, a mono-carboxylic acid or a polycarboxylic acid.

4. The process of claim 1, wherein the chain transfer agent is selected from the group consisting of water, diphenylphosphinic acid, 4-ethylbenzenesulfonic acid, methanol, ethanol, propanol, butanol, pentanol, hexanol, phenol, cyclohexanol, 1,2-ethanediol, 1-2-propanediol, 1,3-propanediol, 1,2-butanediol, 1-3-butanediol, 1,4-butanediol, 1,5-pentanediol, 1,6-hexanediol, 1,2-diphenol, 1,3-diphenol, 1,4-diphenol, catechol, cyclohexanediol, glycerol, benzenetriol, 1,2,4-butanetriol, tris(methylalcohol)propane, tris(methylalcohol)ethane, tris(methylalcohol)nitropropane, D-(+)-glucose, D-sorbitol, calix[4]arene, 2,2-bis(methylalcohol)-1,3-propanediol, polylactic acid, poly(ethylene glycol), starch, lignin, methylamine, dimethylamine, ethylamine, diethylamine, propylamine, dipropylamine, butylamine, dibutylamine, pentylamine, dipentylamine, hexylamine, dihexylamine, 1,4-butanediamine, 3,5-di-tert-butylbenzoic acid, maleic acid, malonic acid, succinic acid, glutaric acid, terephthalic acid, citric acid, 1,3,5-benzenetricarboxylic acid, 1,3,5-cyclohexanetricarboxylic acid, lactic acid, glycolic acid and 3-hydroxypropionic acid.

5. The process of claim 1, wherein the chain transfer agent is present in a molar ratio of between about 1:1 and about 100:1 relative to the metal complex.

6. The process of claim 1, wherein $R_5$ is hydrogen.

7. The process of claim 1, wherein X is independently $OC(O)R^x$, $OSO_2R^x$, $OSO(R^x)_2$, $OR^x$, halide, nitrate, hydroxyl, carbonate, amido or optionally substituted aliphatic, heteroaliphatic, alicyclic, heteroalicyclic, aryl or heteroaryl.

8. A polymerisation system for the copolymerisation of carbon dioxide and at least one epoxide comprising:
   a) a catalyst of formula (I) as defined in claim 1, and
   b) a chain transfer agent of formula (II) as defined in claim 1.

9. A method of producing the copolymer of formula B $-(A)_n$, wherein B is a polycarbonate as produced by the process as defined in claim 1, and each A is a further polymeric unit, the method comprising the steps of:
   a) synthesising a polycarbonate by the process as defined in claim 1, and
   b) ii)—reacting the polycarbonate with at least one further monomer, or
      iii)—reacting the polycarbonate with at least one further polymeric unit.

10. The method of claim 9, wherein step b) ii) or iii) occurs in situ, directly after step a).

11. A catalyst of formula (III):

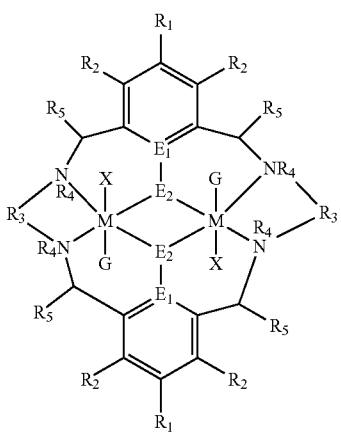

wherein
a) M is independently Mg(II), Ca(II), Ge(II) or Ge(IV)-(X)$_2$, $R_1$ and $R_2$ are independently hydrogen, halide, a nitro group, a nitrile group, an amine, an imine, an ether group, a silyl ether group or an acetylide group or optionally substituted alkyl, alkenyl, alkynyl, haloalkyl, aryl, heteroaryl, alicyclic or heteroalicyclic group;

$R_3$ is independently optionally substituted alkylene, alkenylene, alkynylene, heteroalkylene, heteroalkenylene, heteroalkynylene, arylene, heteroarylene or cycloalkylene, wherein alkylene, alkenylene, alkynylene, heteroalkylene, heteroalkenylene and heteroalkynylene may optionally be interrupted by aryl, heteroaryl, alicyclic or heteroalicyclic;

$R_4$ is independently H, or optionally substituted aliphatic, heteroaliphatic, alicyclic, heteroalicyclic, aryl, heteroaryl, alkylheteroaryl or alkylaryl;

$R_5$ is H, or optionally substituted aliphatic, heteroaliphatic, alicyclic, heteroalicyclic, aryl, heteroaryl, alkylheteroaryl or alkylaryl;

$E_1$ is C and $E_2$ is O, S or NH; or $E_1$ is N and $E_2$ is O;

G is absent or independently a neutral or anionic donor ligand which is a Lewis base;

wherein when both instances of G are absent and all instances of $R_5$ are hydrogen, X is independently OC(O)$R^Z$, OSO($R^Z$)$_2$, OSO$_2R^Y$, OSO$R^T$, O$R^V$, phosphinate, hydroxyl, carbonate, nitrate or optionally substituted aryl, heteroaryl, alicyclic or heteroalicyclic, $R^Z$ is independently hydrogen or optionally substituted C$_{2-20}$aliphatic, C$_{2-20}$haloaliphatic, heteroaliphatic, alicyclic, heteroalicyclic, aryl, alkylaryl or heteroaryl;

$R^Y$ is hydrogen or optionally substituted aliphatic, heteroaliphatic, alicyclic, heteroalicyclic, aryl, heteroaryl or alkylaryl with the proviso that $R^Y$ is not C$_7$H$_7$;

$R^V$ is optionally substituted aryl, haloaryl, heteroaryl, heteroaliphatic, alicyclic, alkylaryl or heteroaliyclic;

$R^T$ is hydrogen, or optionally substituted aliphatic, haloaliphatic, heteroaliphatic, alicyclic, heteroalicyclic, aryl, alkylaryl or heteroaryl;

and wherein when either one or both instances of G are not absent, or one or more instances of $R_5$ is not hydrogen, X is independently OC(O)$R^x$, OSO$_2R^x$, OSO$R^x$, OSO($R^x$)$_2$, O$R^x$, phosphinate, halide, nitrate, hydroxyl, carbonate, amido or optionally substituted aliphatic, heteroaliphatic, alicyclic, heteroalicyclic, aryl or heteroaryl;

$R_x$ is independently hydrogen, or optionally substituted aliphatic, haloaliphatic, heteroaliphatic, alicyclic, heteroalicyclic, aryl, alkylaryl or heteroaryl;

$R_1$, $R_2$, $R_3$, $R_4$, $R_5$, $R^x$, $R^V$, $R^Y$, $R^Z$ and $R^T$ are each independently optionally substituted by halogen, hydroxyl, nitro, carbonate, alkoxy, aryloxy, heteroaryloxy, amino, alkylamino, imine, nitrile, acetylide, or unsubstituted aliphatic, heteroaliphatic, alicyclic, heteroalicyclic, aryl or heteroaryl; or b) M is independently Zn(II), Co(II), Mn(II), Ti(II), Fe(II), Cr(II), Cr(III)-X, Co(III)-X, Mn(III)-X, Fe(III)-X, Al(III)-X, Ti(III)-X, V(III)-X or Ti(IV)-(X)$_2$, G is absent or independently a neutral or anionic donor ligand which is a Lewis base;

$R_5$ is H, or optionally substituted aliphatic, alicyclic, aryl, or alkylaryl;

$E_1$ is C and $E_2$ is O, S or NH; or $E_1$ is N and $E_2$ is O; wherein i) when both instances of G are absent and all instances of $R_5$ are hydrogen, X is independently OC(O)$R^Z$, OSO($R^Z$)$_2$, OSO$_2R^Y$, OSO$R^T$, O$R^V$, phosphinate, hydroxyl, carbonate, nitrate or optionally substituted aryl, heteroaryl, alicyclic or heteroalicyclic;

$R_1$ and $R_2$ are independently hydrogen, halide, a nitro group, a nitrile group, an imine, an ether group, a silyl ether group or an acetylide group or optionally substituted alkyl, alkenyl, alkynyl, haloalkyl, aryl or alicyclic group;

$R_3$ is independently optionally substituted alkylene, alkenylene, alkynylene, arylene or cycloalkylene, wherein alkylene, alkenylene or alkynylene may optionally be interrupted by aryl or alicyclic;

$R_4$ is independently H, or optionally substituted aliphatic, alicyclic, aryl, or alkylaryl;

$R^Z$ is independently hydrogen or optionally substituted C$_{2-20}$aliphatic, C$_{2-20}$haloaliphatic, heteroaliphatic, alicyclic, heteroalicyclic, aryl, alkylaryl or heteroaryl;

$R^Y$ is hydrogen or optionally substituted aliphatic, heteroaliphatic, alicyclic, heteroalicyclic, aryl, heteroaryl or alkylaryl with the proviso that $R^Y$ is not C$_7$H$_7$;

$R^V$ is optionally substituted aryl, haloaryl, heteroaryl, heteroaliphatic, alicyclic, alkylaryl or heteroaliyclic;

$R^T$ is hydrogen, or optionally substituted aliphatic, haloaliphatic, alicyclic, aryl or alkylaryl;

$R_1$, $R_2$, $R_3$ and $R_4$ are each independently optionally substituted by halogen, hydroxyl, nitro, carbonate, alkoxy, aryloxy, imine, nitrile, acetylide, unsubstituted aliphatic, unsubstituted alicyclic or unsubstituted aryl; and $R^V$, $R^Y$, $R^Z$ and $R^T$ are each independently optionally substituted by halogen, hydroxyl, nitro, carbonate, alkoxy, aryloxy, heteroaryloxy, amino, alkylamino, imine, nitrile, acetylide, or unsubstituted aliphatic, heteroaliphatic, alicyclic, heteroalicyclic, aryl or heteroaryl;

ii) when either one or both instances of G are not absent, X is independently OC(O)$R^x$, OSO$_2R^x$, OSO$R^x$, OSO($R^x$)$_2$, O$R^x$, phosphinate, halide, nitrate, hydroxyl, carbonate, amido or optionally substituted aliphatic, heteroaliphatic, alicyclic, heteroalicyclic, aryl or heteroaryl;

$R^x$ is independently hydrogen, or optionally substituted aliphatic, haloaliphatic, heteroaliphatic, alicyclic, heteroalicyclic, aryl, alkylaryl or heteroaryl;

$R_1$ and $R_2$ are independently hydrogen, halide, a nitro group, a nitrile group, an imine, an amine, an ether group, a silyl ether group, or an acetylide group or an optionally substituted alkyl, alkenyl, alkynyl, haloalkyl, aryl, heteroaryl, alicyclic or heteroalicyclic;

$R_3$ is optionally substituted alkylene, alkenylene, alkynylene, heteroalkylene, heteroalkenylene, heteroalkynylene, arylene, heteroarylene or cycloalkylene, wherein alkylene, alkenylene, alkynylene, heteroalkylene, heteroalkenylene and heteroalkynylene may optionally be interrupted by aryl, heteroaryl, alicyclic or heteroalicyclic;

$R_4$ is H, or optionally substituted aliphatic, heteroaliphatic, alicyclic, heteroalicyclic, aryl, heteroaryl, alkylheteroaryl or alkylaryl; and $R_1, R_2, R_3, R_4, R_5$ and $R^x$ are each independently optionally substituted by halogen, hydroxyl, nitro, carbonate, alkoxy, aryloxy, heteroaryloxy, amino, alkylamino, imine, nitrile, acetylide, or unsubstituted aliphatic, heteroaliphatic, alicyclic, heteroalicyclic, aryl or heteroaryl; or iii) when or one or more instances of $R_5$ are not hydrogen, X is independently $OC(O)R^x$, $OSO_2R^x$, $OSOR^x$, $OSO(R^x)_2$, $OR^x$, phosphinate, halide, nitrate, hydroxyl, carbonate, amido or optionally substituted aliphatic, heteroaliphatic, alicyclic, heteroalicyclic, aryl or heteroaryl;

$R^x$ is independently hydrogen, or optionally substituted aliphatic, haloaliphatic, heteroaliphatic, alicyclic, heteroalicyclic, aryl, alkylaryl or heteroaryl;

$R_1$ and $R_2$ are independently hydrogen, halide, a nitro group, a nitrile group, an imine, an ether group, a silyl ether group or an acetylide group or optionally substituted alkyl, alkenyl, alkynyl, haloalkyl, aryl or alicyclic group;

$R_3$ is independently optionally substituted alkylene, alkenylene, alkynylene, arylene or cycloalkylene, wherein alkylene, alkenylene or alkynylene may optionally be interrupted by aryl or alicyclic;

$R_4$ is independently H, or optionally substituted aliphatic, alicyclic, aryl, or alkylaryl;

$R_1, R_2, R_3, R_4$ and $R_5$ are each independently optionally substituted by halogen, hydroxyl, nitro, carbonate, alkoxy, aryloxy, imine, nitrile, acetylide, unsubstituted aliphatic, unsubstituted alicyclic or unsubstituted aryl; and $R^x$ is independently optionally substituted by halogen, hydroxyl, nitro, carbonate, alkoxy, aryloxy, heteroaryloxy, amino, alkylamino, imine, nitrile, acetylide, or unsubstituted aliphatic, heteroaliphatic, alicyclic, heteroalicyclic, aryl or heteroaryl;

with the proviso that the catalyst is not:
  $[Co_2LCl_2(CH_3OH)_2]\cdot H_2O$,
  $[Co_2LBr_2(CH_3OH)_2]\cdot H_2O$,
  $[Mn_2LCl_2(CH_3OH)_2]\cdot H_2O$,
  $[Mn_2LBr_2(CH_3OH)_2]\cdot H_2O$,
  $[Co^{II}Co^{III}LCl_2Br(CH_3OH)]\cdot 0.5CH_2Cl_2$,
  $[Mn^{II}Mn^{III}LCl_2Br(CH_3OH)]$, or
  $[Fe^{II}Co^{II}L(\mu\text{-}OAc)(OAc)(H_2O)]$, wherein L is

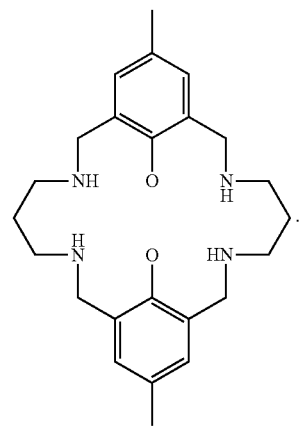

12. The catalyst according to claim 11, wherein M is independently Mg(II), Zn(II), Ca(II), Ge(II), Co(II), Mn(II), Ti(II), Fe(II), Cr(II), Cr(III)-X, Co(III)-X, Mn(III)-X, Fe(III)-X, Al(III)-X, Ti(III)-X, V(III)-X, Ge(IV)-(X)$_2$ or Ti(IV)-(X)$_2$, G is absent or independently a neutral or anionic donor ligand which is a Lewis base;

$R_5$ is H, or optionally substituted aliphatic, alicyclic, aryl, or alkylaryl;

$E_1$ is C and $E_2$ is O, S or NH; or $E_1$ is N and $E_2$ is O; wherein i) when both instances of G are absent and all instances of $R_5$ are hydrogen, X is independently $OC(O)R^Z$, $OSO(R^Z)_2$, $OSO_2R^Y$, $OSOR^T$, $OR^V$, phosphinate, hydroxyl, carbonate, nitrate or optionally substituted aryl, heteroaryl, alicyclic or heteroalicyclic;

$R_1$ and $R_2$ are independently hydrogen, halide, a nitro group, a nitrile group, an imine, an ether group, a silyl ether group or an acetylide group or optionally substituted alkyl, alkenyl, alkynyl, haloalkyl, aryl or alicyclic group;

$R_3$ is independently optionally substituted alkylene, alkenylene, alkynylene, arylene or cycloalkylene, wherein alkylene, alkenylene or alkynylene may optionally be interrupted by aryl or alicyclic;

$R_4$ is independently H, or optionally substituted aliphatic, alicyclic, aryl, or alkylaryl;

$R^Z$ is independently hydrogen or optionally substituted $C_{2\text{-}20}$aliphatic, $C_{2\text{-}20}$haloaliphatic, heteroaliphatic, alicyclic, heteroalicyclic, aryl, alkylaryl or heteroaryl;

$R^Y$ is hydrogen or optionally substituted aliphatic, heteroaliphatic, alicyclic, heteroalicyclic, aryl, heteroaryl or alkylaryl with the proviso that $R^Y$ is not $C_7H_7$;

$R^V$ is optionally substituted aryl, haloaryl, heteroaryl, heteroaliphatic, alicyclic, alkylaryl or heteroaliyclic;

$R^T$ is hydrogen, or optionally substituted aliphatic, haloaliphatic, alicyclic, aryl or alkylaryl;

$R_1, R_2, R_3$ and $R_4$ are each independently optionally substituted by halogen, hydroxyl, nitro, carbonate, alkoxy, aryloxy, imine, nitrile, acetylide, unsubstituted aliphatic, unsubstituted alicyclic and unsubstituted aryl; and $R^V, R^Y, R^Z$ and $R^T$ are each independently optionally substituted by halogen, hydroxyl, nitro, carbonate, alkoxy, aryloxy, heteroaryloxy, amino, alkylamino, imine, nitrile, acetylide, or unsubstituted aliphatic, heteroaliphatic, alicyclic, heteroalicyclic, aryl or heteroaryl;

ii) when either one or both instances of G are not absent, X is independently $OC(O)R^x$, $OSO_2R^x$, $OSOR^x$, $OSO(R^x)_2$, $OR^x$, phosphinate, halide, nitrate, hydroxyl, carbonate, amido or optionally substituted aliphatic, heteroaliphatic, alicyclic, heteroalicyclic, aryl or heteroaryl;

$R^x$ is independently hydrogen, or optionally substituted aliphatic, haloaliphatic, heteroaliphatic, alicyclic, heteroalicyclic, aryl, alkylaryl or heteroaryl;

$R_1$ and $R_2$ are independently hydrogen, halide, a nitro group, a nitrile group, an imine, an amine, an ether group, a silyl ether group, or an acetylide group or an optionally substituted alkyl, alkenyl, alkynyl, haloalkyl, aryl, heteroaryl, alicyclic or heteroalicyclic;

$R_3$ is optionally substituted alkylene, alkenylene, alkynylene, heteroalkylene, heteroalkenylene, heteroalkynylene, arylene, heteroarylene or cycloalkylene, wherein alkylene, alkenylene, alkynylene, heteroalkylene, heteroalkenylene and heteroalkynylene may optionally be interrupted by aryl, heteroaryl, alicyclic or heteroalicyclic;

$R_4$ is H, or optionally substituted aliphatic, heteroaliphatic, alicyclic, heteroalicyclic, aryl, heteroaryl, alkylheteroaryl or alkylaryl; and $R_1$, $R_2$, $R_3$, $R_4$, $R_5$ and $R^x$ are each independently optionally substituted by halogen, hydroxyl, nitro, carbonate, alkoxy, aryloxy, heteroaryloxy, amino, alkylamino, imine, nitrile, acetylide, or unsubstituted aliphatic, heteroaliphatic, alicyclic, heteroalicyclic, aryl or heteroaryl; or iii) when or one or more instances of $R_5$ are not hydrogen, X is independently $OC(O)R^x$, $OSO_2R^x$, $OSOR^x$, $OSO(R^x)_2$, $OR^x$, phosphinate, halide, nitrate, hydroxyl, carbonate, amido or optionally substituted aliphatic, heteroaliphatic, alicyclic, heteroalicyclic, aryl or heteroaryl;

$R^x$ is independently hydrogen, or optionally substituted aliphatic, haloaliphatic, heteroaliphatic, alicyclic, heteroalicyclic, aryl, alkylaryl or heteroaryl;

$R_1$ and $R_2$ are independently hydrogen, halide, a nitro group, a nitrile group, an imine, an ether group, a silyl ether group or an acetylide group or optionally substituted alkyl, alkenyl, alkynyl, haloalkyl, aryl or alicyclic group;

$R_3$ is independently optionally substituted alkylene, alkenylene, alkynylene, arylene or cycloalkylene, wherein alkylene, alkenylene or alkynylene may optionally be interrupted by aryl or alicyclic;

$R_4$ is independently H, or optionally substituted aliphatic, alicyclic, aryl, or alkylaryl;

$R_1$, $R_2$, $R_3$, $R_4$ and $R_5$ are each independently optionally substituted by halogen, hydroxyl, nitro, carbonate, alkoxy, aryloxy, imine, nitrile, acetylide, unsubstituted aliphatic, unsubstituted alicyclic or unsubstituted aryl; and $R^x$ is independently optionally substituted by halogen, hydroxyl, nitro, carbonate, alkoxy, aryloxy, heteroaryloxy, amino, alkylamino, imine, nitrile, acetylide, or unsubstituted aliphatic, heteroaliphatic, alicyclic, heteroalicyclic, aryl or heteroaryl.

13. The catalyst according to claim 11, wherein M is independently Mg(II), Zn(II), Ca(II), Ge(II), Co(II), Mn(II), Ti(II), Fe(II), Cr(II), Cr(III)-X, Co(III)-X, Mn(III)-X, Fe(III)-X, Al(III)-X, Ti(III)-X, V(III)-X, Ge(IV)-(X)$_2$ or Ti(IV)-(X)$_2$, $R_1$ and $R_2$ are independently hydrogen, halide, a nitro group, a nitrile group, an imine, an ether group, a silyl ether group or an acetylide group or optionally substituted alkyl, alkenyl, alkynyl, haloalkyl, aryl or alicyclic group;

$R_3$ is independently optionally substituted alkylene, alkenylene, alkynylene, arylene or cycloalkylene, wherein alkylene, alkenylene or alkynylene may optionally be interrupted by aryl or alicyclic;

$R_4$ is independently H, or optionally substituted aliphatic, alicyclic, aryl, or alkylaryl;

$R_5$ is H, or optionally substituted aliphatic, alicyclic, aryl, or alkylaryl;

$E_1$ is C and $E_2$ is O, S or NH; or $E_1$ is N and $E_2$ is O;

G is absent or independently a neutral or anionic donor ligand which is a Lewis base;

X is independently $OC(O)R^Z$, $OSO(R^Z)_2$, $OSO_2R^Y$, $OSOR^T$, $OR^V$, phosphinate, hydroxyl, carbonate, nitrate or optionally substituted aryl, heteroaryl, alicyclic or heteroalicyclic;

$R^Z$ is independently hydrogen or optionally substituted $C_{2-20}$aliphatic, $C_{2-20}$haloaliphatic, heteroaliphatic, alicyclic, heteroalicyclic, aryl, alkylaryl or heteroaryl;

$R^Y$ is hydrogen or optionally substituted aliphatic, heteroaliphatic, alicyclic, heteroalicyclic, aryl, heteroaryl or alkylaryl with the proviso that $R^Y$ is not $C_7H_7$;

$R^V$ is optionally substituted aryl, haloaryl, heteroaryl, heteroaliphatic, alicyclic, alkylaryl or heteroaliyclic;

$R^T$ is hydrogen, or optionally substituted aliphatic, haloaliphatic, alicyclic, aryl or alkylaryl;

$R_1$, $R_2$, $R_3$, $R_4$ and $R_5$ are each independently optionally substituted by halogen, hydroxyl, nitro, carbonate, alkoxy, aryloxy, imine, nitrile, acetylide, unsubstituted aliphatic, unsubstituted alicyclic or unsubstituted aryl; and $R^V$, $R^Y$, $R^Z$ and $R^T$ are each independently optionally substituted by halogen, hydroxyl, nitro, carbonate, alkoxy, aryloxy, heteroaryloxy, amino, alkylamino, imine, nitrile, acetylide, or unsubstituted aliphatic, heteroaliphatic, alicyclic, heteroalicyclic, aryl or heteroaryl.

14. The catalyst according to claim 11, wherein the catalyst is:

[L$^1$Mg$_2$Cl$_2$(methylimidazole)],

[L$^1$Mg$_2$Cl$_2$(dimethylaminopyridine)],

[L$^1$Mg$_2$Br$_2$(dimethylaminopyridine)],

[L$^1$Zn$_2$(OOCC(CH$_3$)$_3$)$_2$],

[L$^1$Zn$_2$(pentafluorobenzoate)$_2$],

[L$^1$Zn$_2$(adamantyl carboxylate)$_2$],

[L$^1$Zn$_2$(diphenyl phosphinate)$_2$],

[L$^1$Zn$_2$(bis(4-methoxy)phenyl phosphinate)$_2$],

[L⁴Mg₂(OCOCH₃)₂],

[L¹Zn₂(OC₆H₅)₂],

[L¹Zn₂(hexanoate)₂],

[L¹Zn₂(octanoate)₂],

[L¹Zn₂(dodecanoate)₂],

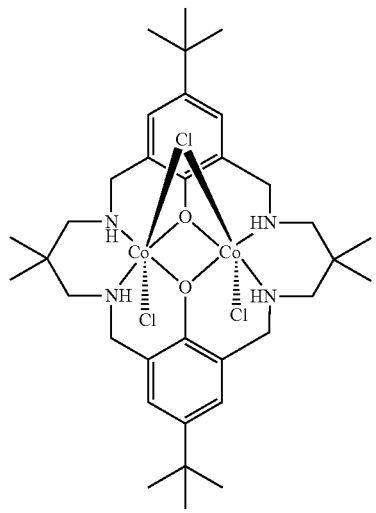

[L¹Co₂Cl₃]⁻ [B—H]⁺ wherein [B—H]⁺ represents any counterion, or

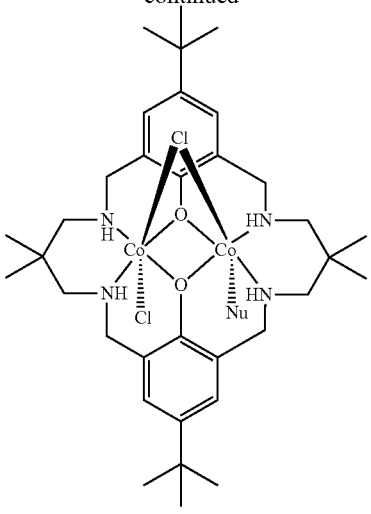

[L¹Co₂Cl₂Nu]

wherein Nu is N-methylimidazole, pyridine, or dimethylaminopyridine.

15. The method of claim 9, wherein A is a polymer formed from at least one monomer which is initiated by hydroxyl groups.

16. The method of claim 9, wherein A is a polymer formed from lactide, lactone, epoxide, cyclic carbonate, epoxide monomers or combinations thereof, or a combination of an epoxide and an anhydride and/or carbon dioxide and/or a di- or poly-carboxylic acid, or a combination of a di-isocyanate and a compound comprising two or more hydroxyl groups, or wherein A is a polyester, polyether, polycarbonate, polyamide, polyurethane or any copolymer combination thereof.

17. The process of claim 1, wherein the chain transfer agent is present in a molar ratio of at least about 2:1 relative to the catalyst of formula (I).

18. The process of claim 1, wherein the chain transfer agent is present in a molar ratio of at least about 4:1 relative to the catalyst of formula (I).

19. The process of claim 1, wherein the chain transfer agent is present in a molar ratio of at least about 8:1 relative to the catalyst of formula (I).

* * * * *